United States Patent
Fan et al.

(10) Patent No.: US 9,895,160 B2
(45) Date of Patent: Feb. 20, 2018

(54) SURGICAL OPERATING APPARATUS WITH TEMPERATURE CONTROL

(71) Applicant: GYRUS ACMI, INC., Southborough, MA (US)

(72) Inventors: Tailin Fan, Nashua, NH (US); Kester J Batchelor, Mound, MN (US); Jeff Nelson, Maple Grove, MN (US)

(73) Assignee: GYRUS ACMI INC., Southborough, MA (US)

(*) Notice: Subject to any disclaimer, the term of this patent is extended or adjusted under 35 U.S.C. 154(b) by 169 days.

(21) Appl. No.: 14/254,412

(22) Filed: Apr. 16, 2014

(65) Prior Publication Data

US 2015/0297255 A1 Oct. 22, 2015

(51) Int. Cl.
*A61B 18/12* (2006.01)
*A61B 17/32* (2006.01)
(Continued)

(52) U.S. Cl.
CPC ........ *A61B 17/320068* (2013.01); *A61B 17/320092* (2013.01); *A61B 18/1445* (2013.01);
(Continued)

(58) Field of Classification Search
CPC ........ A61B 17/320068; A61B 18/1482; A61B 18/1492; A61B 2018/0019;
(Continued)

(56) References Cited

U.S. PATENT DOCUMENTS 4,867,141 A * 9/1989 Nakada ............ A61B 17/22012
601/4
5,222,937 A * 6/1993 Kagawa ......... A61B 17/320068
604/22
(Continued)

FOREIGN PATENT DOCUMENTS

EP 1633236 B1 4/2013
EP 2 679 188 A1 1/2014
(Continued)

OTHER PUBLICATIONS

International Search Report and the Written Opinion dated Jul. 16, 2015 from related International PCT Application No. PCT/US2015/025862.

*Primary Examiner* — Daniel Fowler
(74) *Attorney, Agent, or Firm* — Scully, Scott, Murphy & Presser, P.C.

(57) ABSTRACT

A probe includes a probe distal end body, a vibration transmission body and a heat dissipation unit. The probe distal end body includes a first electrode. The vibration transmission body is arranged to a proximal end of the probe distal end body. The vibration transmission body transmits ultrasonic vibration generated by an ultrasonic transducer to the probe distal end body, and transmits current to the first electrode. An interior surface of the probe distal end body and an interior surface of the vibration transmission body define an interior space. The heat dissipation unit dissipates heat generated at the probe distal end body, wherein at least a portion of the heat dissipation unit is arranged in the interior space defined by the probe distal end body and the vibration transmission body. A treatment instrument includes the probe and an end effector including a second electrode.

31 Claims, 43 Drawing Sheets

(51) Int. Cl.
*A61B 18/14* (2006.01)
*A61B 18/00* (2006.01)
*A61B 17/28* (2006.01)

(52) U.S. Cl.
CPC ............... *A61B 2017/2825* (2013.01); *A61B 2018/00023* (2013.01); *A61B 2018/00095* (2013.01); *A61B 2018/00994* (2013.01); *A61B 2018/1467* (2013.01)

(58) Field of Classification Search
CPC .. A61B 2018/00994; A61B 2018/1467; A61N 2007/0047
See application file for complete search history.

(56) References Cited

U.S. PATENT DOCUMENTS

| | | | |
|---|---|---|---|
| 5,255,669 A | 10/1993 | Kubota et al. | |
| 5,304,115 A | 4/1994 | Pflueger et al. | |
| 5,460,629 A * | 10/1995 | Shlain | A61B 18/1482 606/46 |
| 5,827,203 A | 10/1998 | Nita | |
| 5,830,214 A * | 11/1998 | Flom | A61B 18/1482 604/33 |
| 5,893,835 A * | 4/1999 | Witt | A61B 17/320092 601/2 |
| 5,906,628 A * | 5/1999 | Miyawaki | A61B 17/320092 606/169 |
| 6,056,735 A * | 5/2000 | Okada | A61B 17/320092 606/1 |
| 6,280,441 B1 * | 8/2001 | Ryan | A61B 18/148 600/373 |
| 6,551,309 B1 * | 4/2003 | LePivert | A61B 18/02 606/20 |
| 6,783,524 B2 | 8/2004 | Anderson et al. | |
| 7,004,940 B2 | 2/2006 | Ryan et al. | |
| 8,480,593 B2 | 7/2013 | Magnin et al. | |
| 2002/0165469 A1 | 11/2002 | Murakami | |
| 2003/0139789 A1 * | 7/2003 | Tvinnereim | A61B 18/1485 607/99 |
| 2004/0097911 A1 | 5/2004 | Murakami et al. | |
| 2004/0199161 A1 * | 10/2004 | Truckai | A61B 18/1442 606/48 |
| 2004/0267167 A1 * | 12/2004 | Podany | A61B 17/22004 601/2 |

FOREIGN PATENT DOCUMENTS

| | | |
|---|---|---|
| JP | 2007050187 A2 | 3/2007 |
| JP | 4801220 B1 | 8/2011 |
| WO | 2005099605 A1 | 10/2005 |
| WO | 2012166476 A1 | 12/2012 |
| WO | 2013102830 A1 | 7/2013 |

* cited by examiner

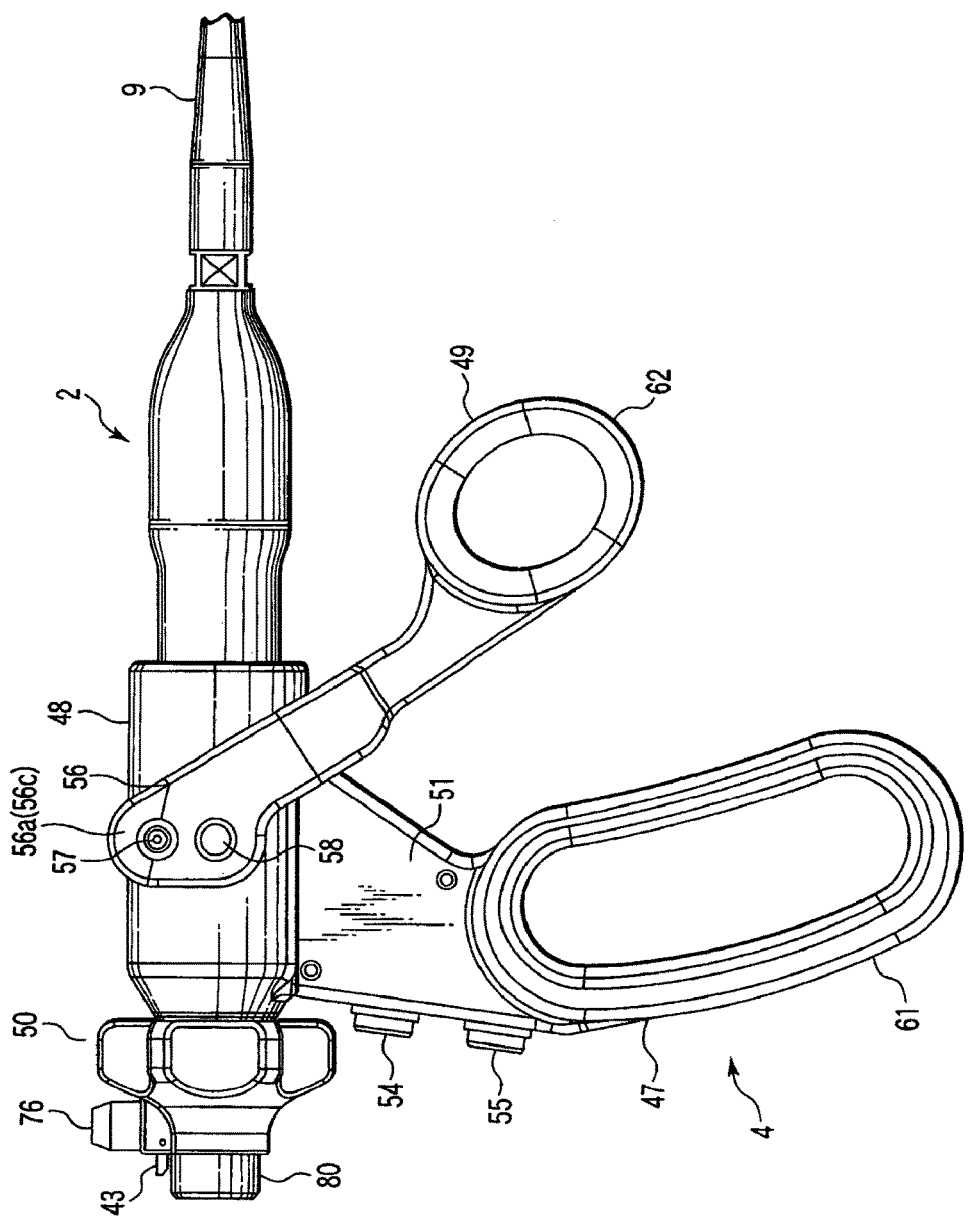
F I G. 3

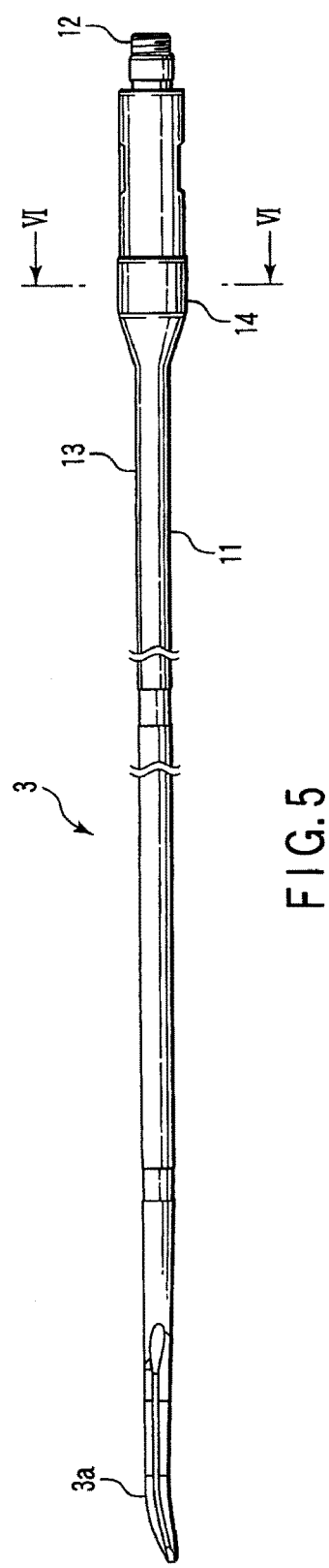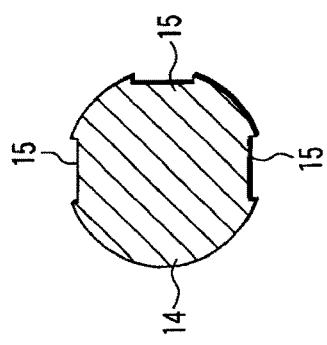
FIG. 5
FIG. 6

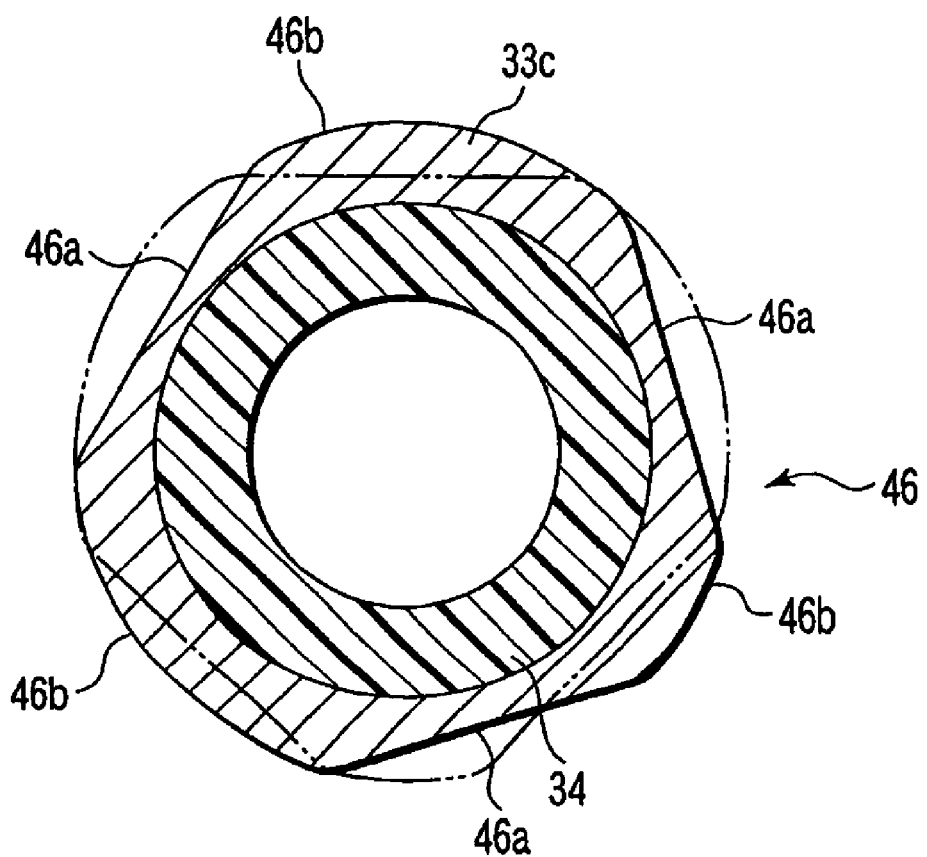
F I G. 9B

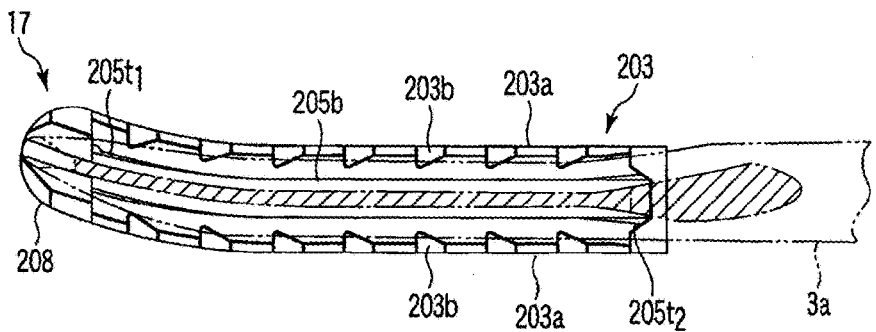
F I G. 17
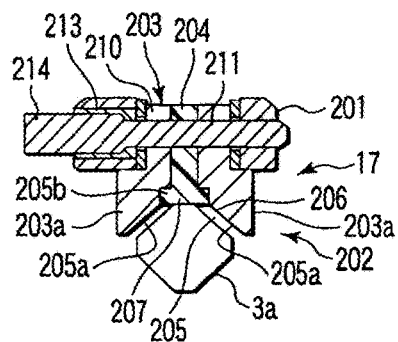
F I G. 18
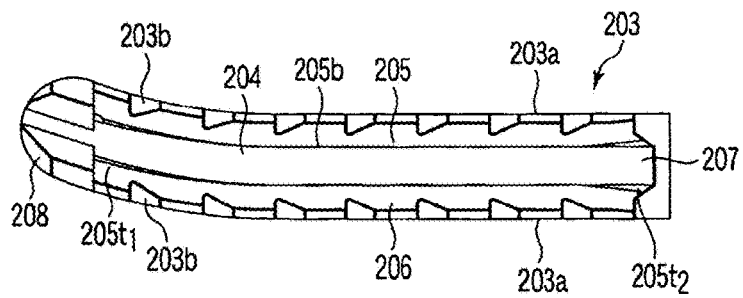
F I G. 19
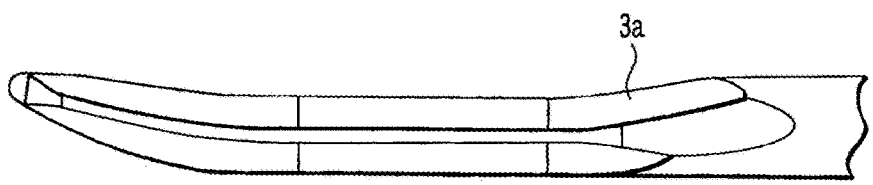
F I G. 20

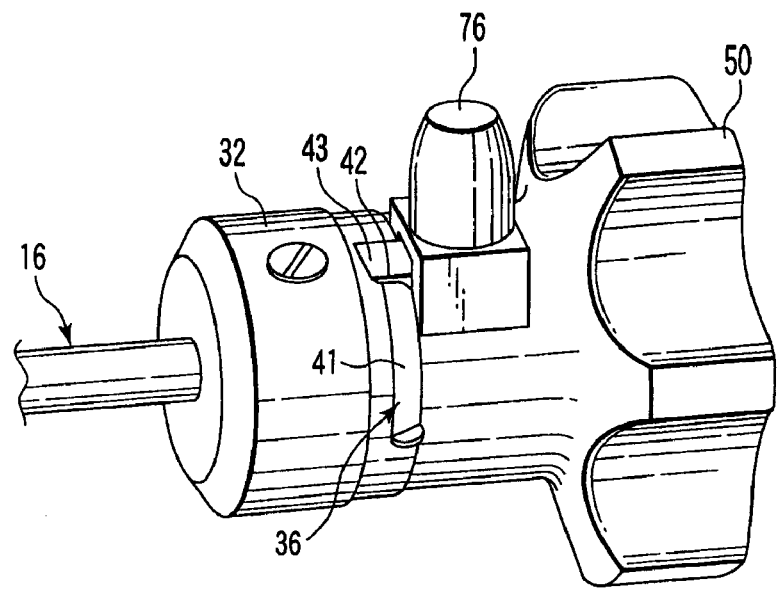
F I G. 31
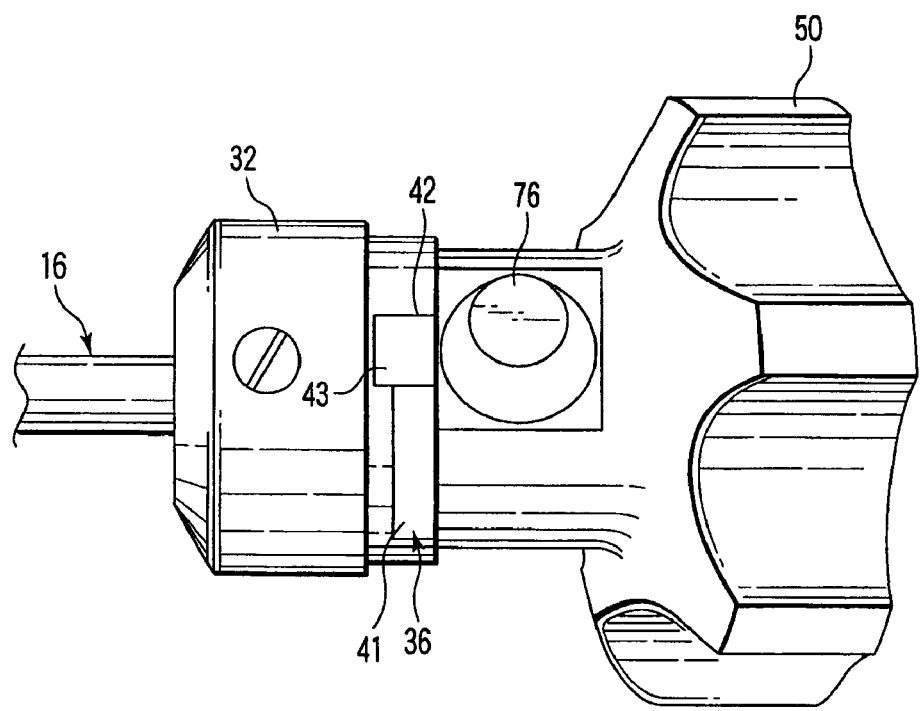
F I G. 32

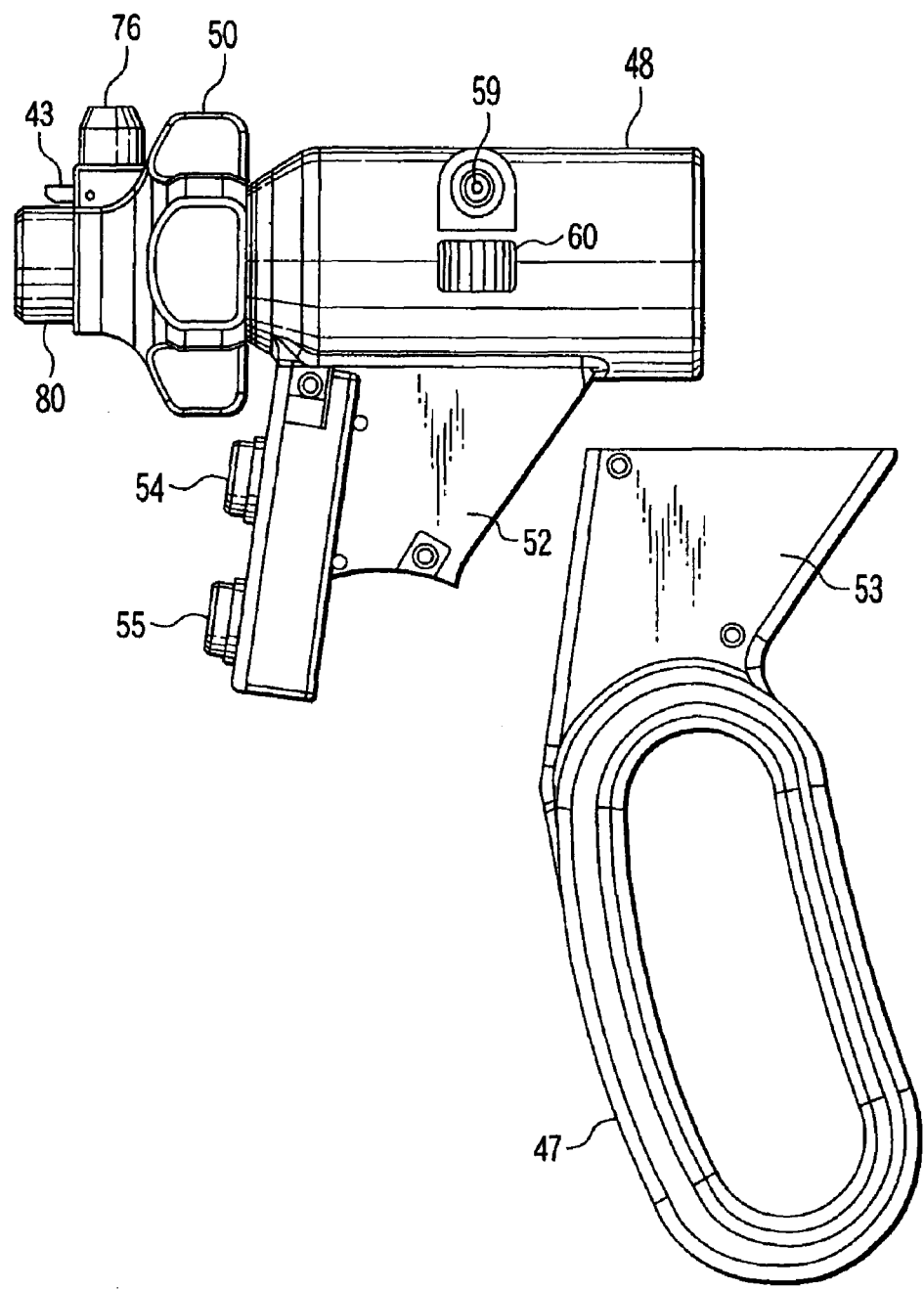
F I G. 36

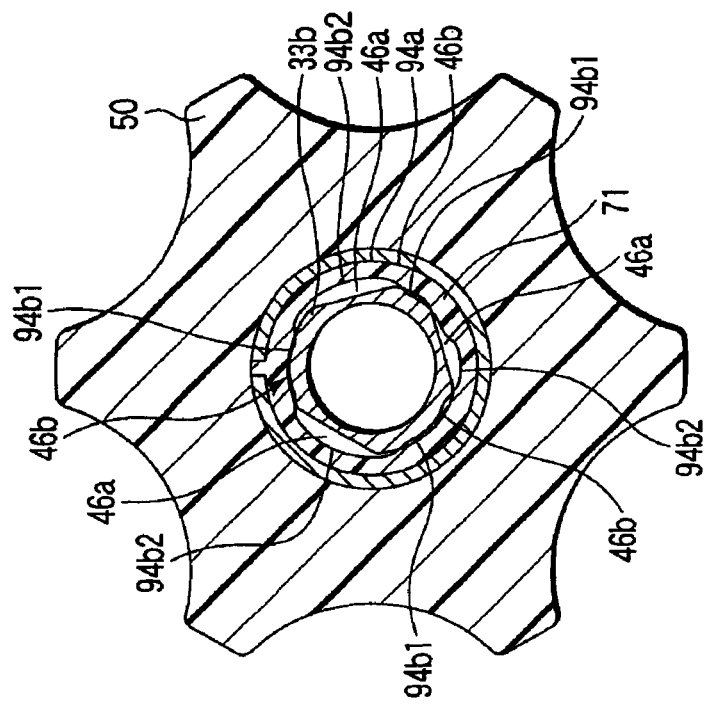
F I G. 41B
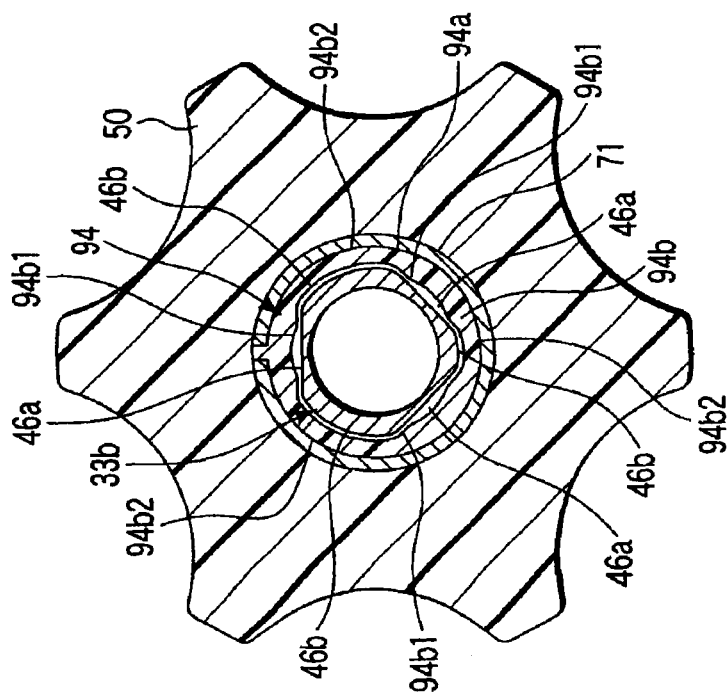
F I G. 41A

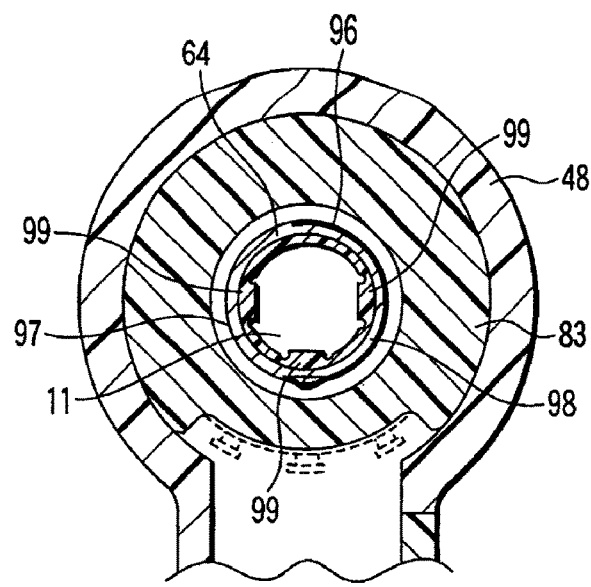
F I G. 42
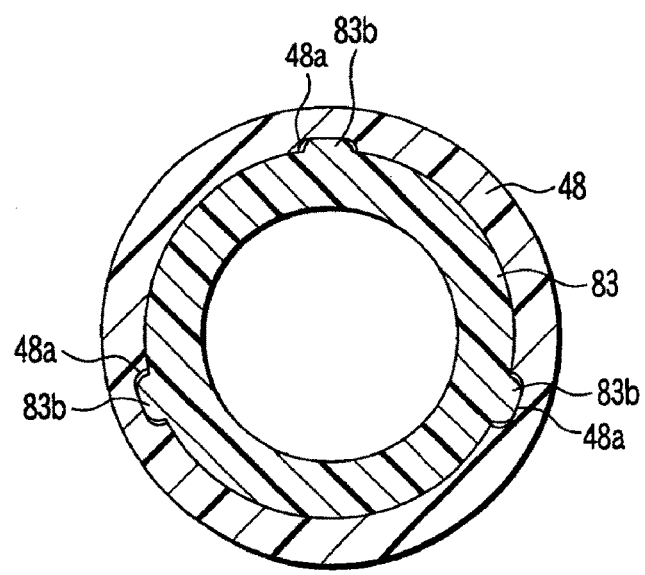
F I G. 51

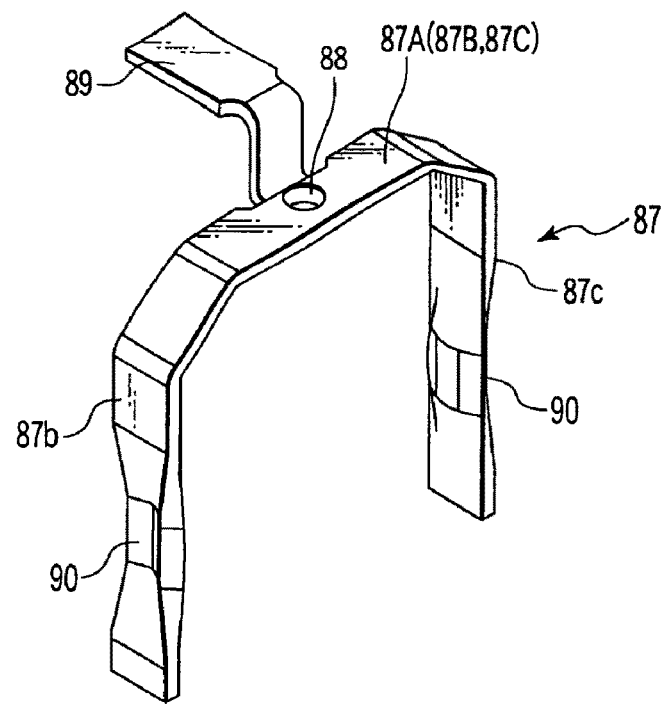
F I G. 49
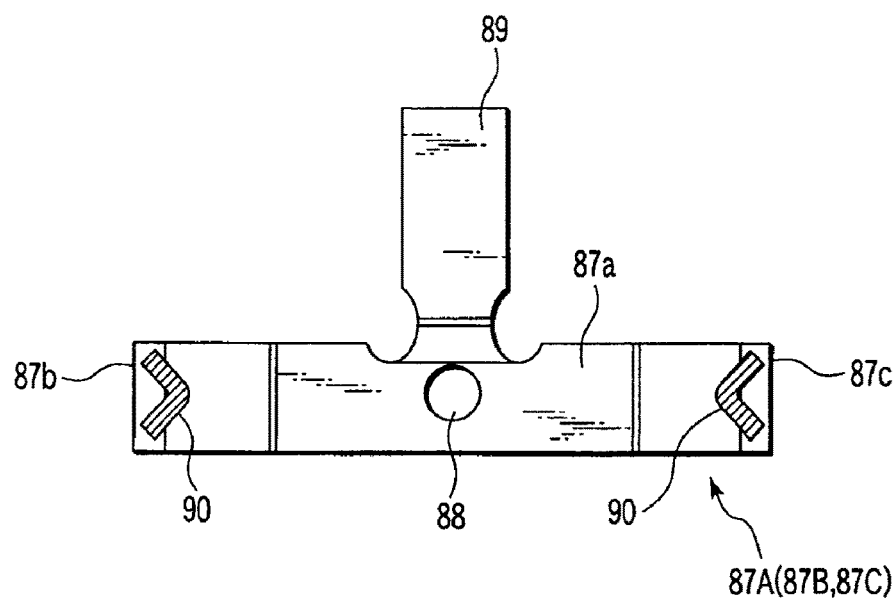
F I G. 50

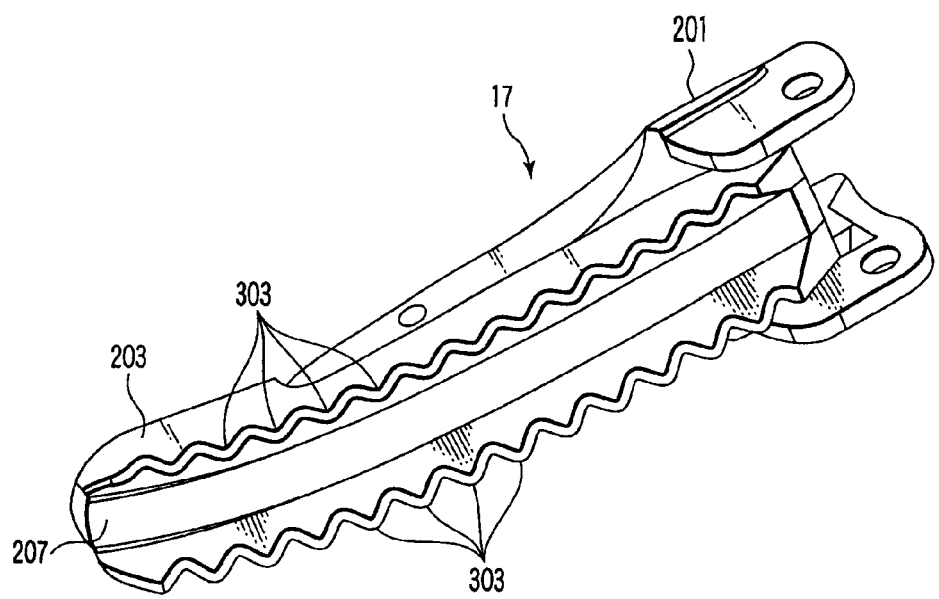
F I G. 55
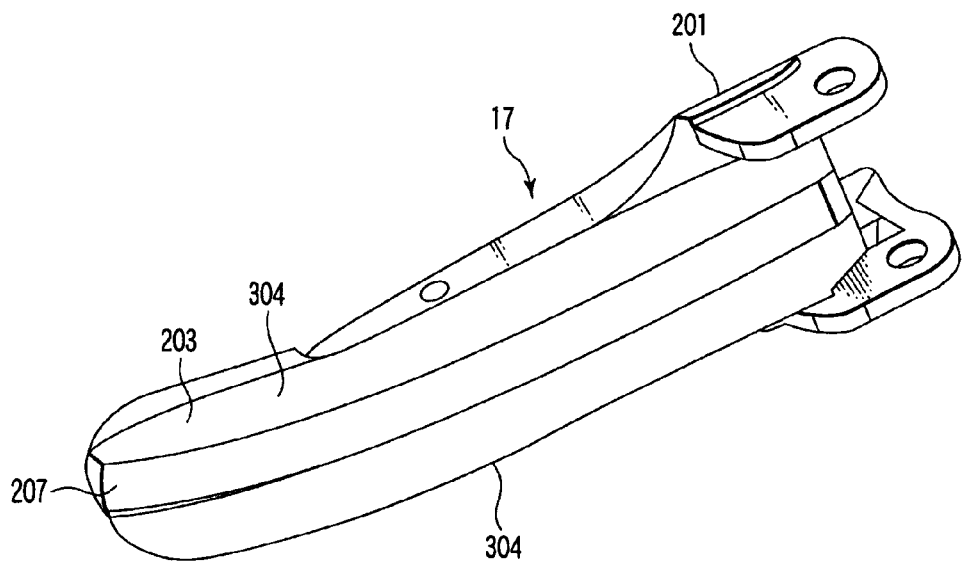
F I G. 56

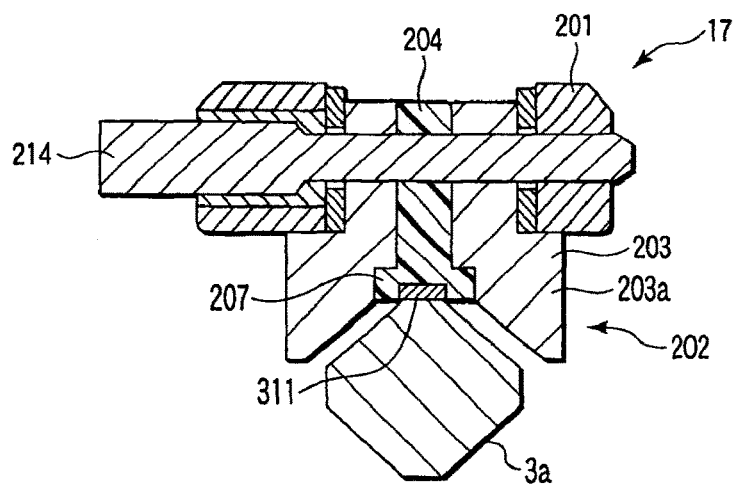
F I G. 59
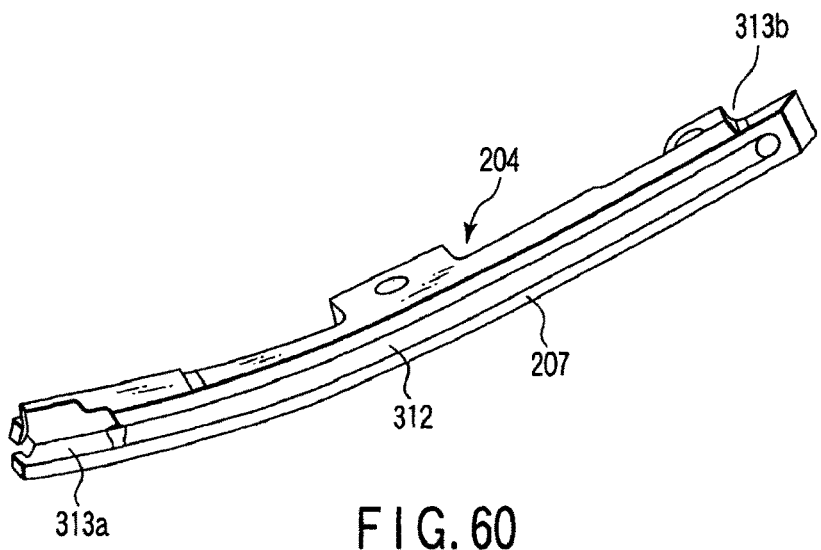
F I G. 60
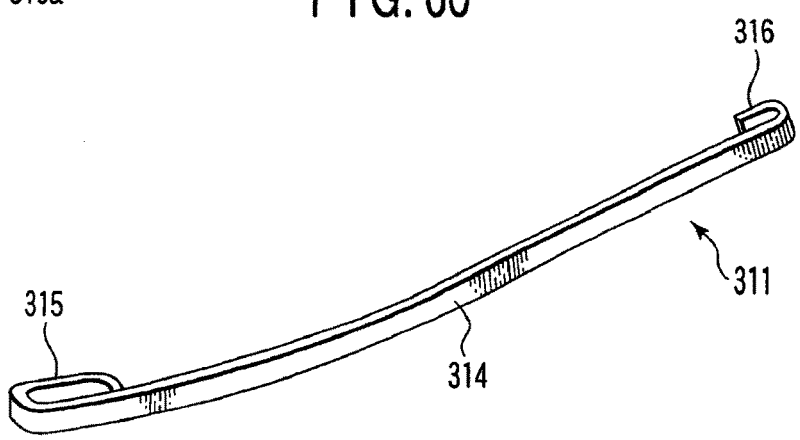
F I G. 61

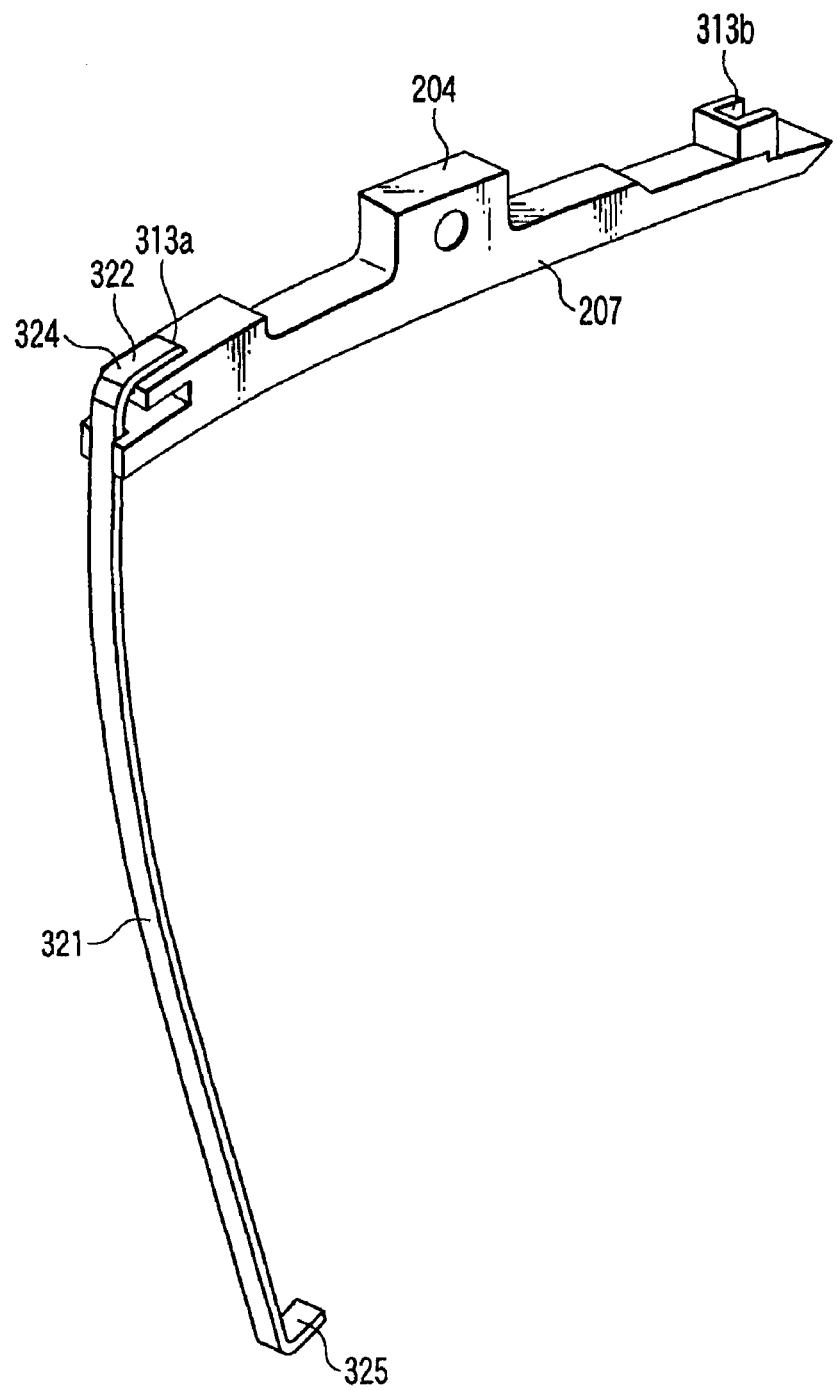
F I G. 65

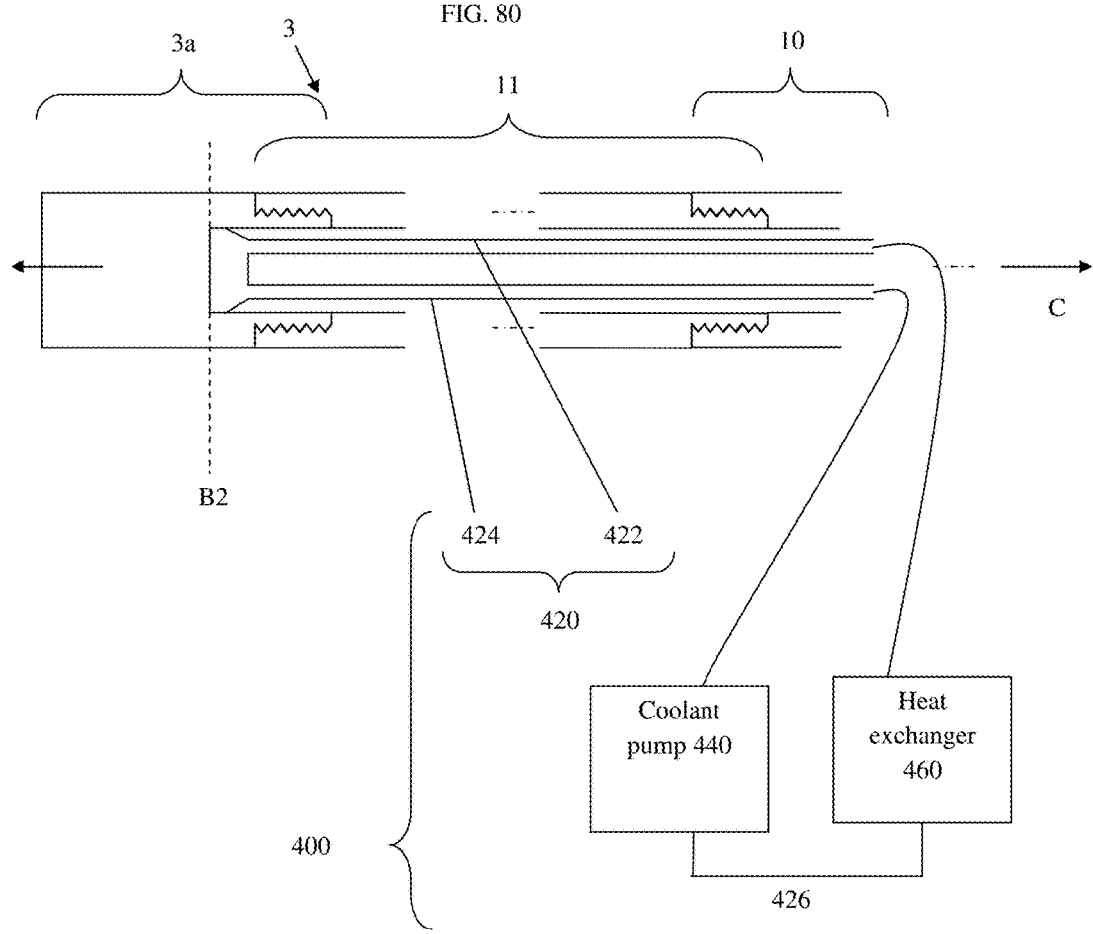

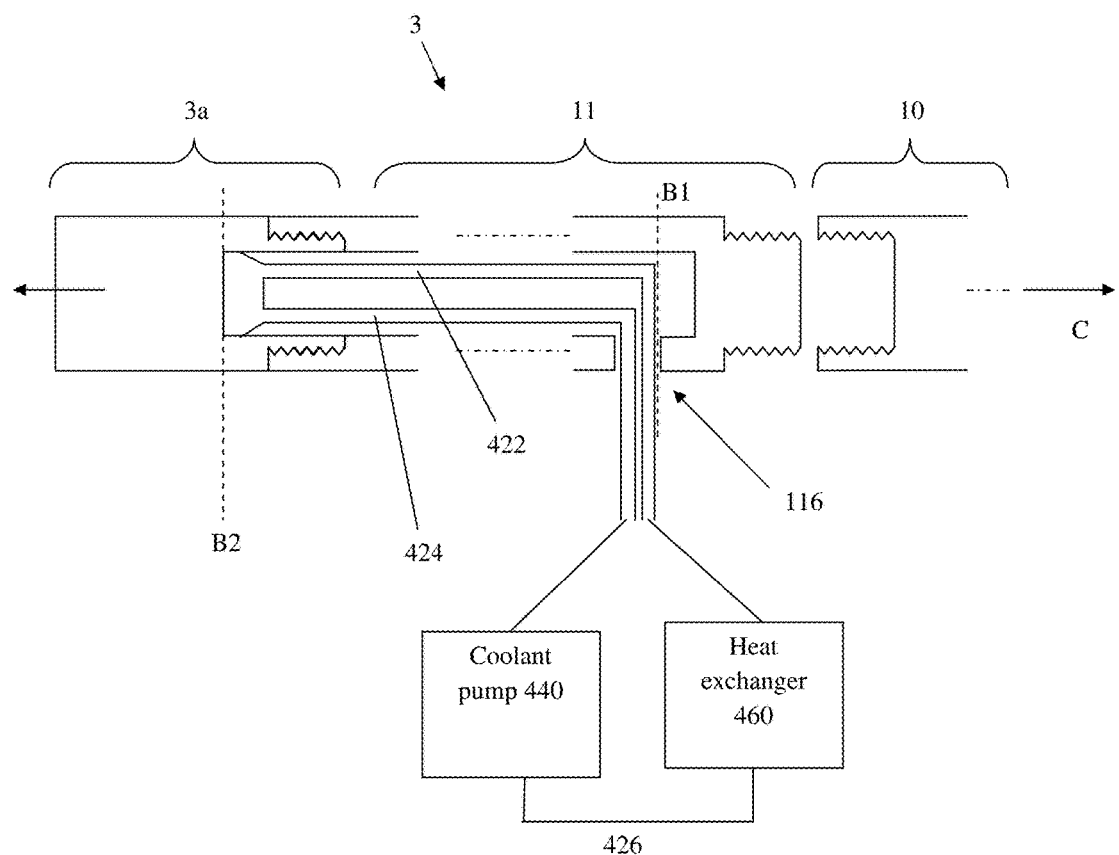

SURGICAL OPERATING APPARATUS WITH TEMPERATURE CONTROL

BACKGROUND

The present invention relates to a surgical operation apparatus which performs therapeutic treatment, such as incision, resection or coagulation, of a living body tissue by making use of ultrasonic and composite energy of ultrasonic and high-frequency waves.

SUMMARY

This summary is provided to introduce a selection of concepts in a simplified form that are further described below in the Detailed Description. This summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

A probe according to a first aspect of the invention is provided. The probe comprises: a probe distal end body comprising a first electrode; a vibration transmission body arranged to a proximal end of the probe distal end body, wherein the vibration transmission body is configured to transmit ultrasonic vibration generated by an ultrasonic transducer to the probe distal end body, and to transmit current to the first electrode, and wherein an interior surface of the probe distal end body and an interior surface of the vibration transmission body define an interior space; and a heat dissipation unit configured to dissipate heat generated at the probe distal end body, wherein at least a portion of the heat dissipation unit is arranged in the interior space defined by the probe distal end body and the vibration transmission body.

A treatment instrument according to a second aspect of the invention is provided. The treatment instrument comprises: a probe comprising: a probe distal end body comprising a first electrode of a pair of bipolar electrodes, wherein the first electrode is electrically connected to a first electric path through which an electric current is transmitted; a vibration transmission body arranged to a proximal end of the probe distal end body, wherein the vibration transmission body is configured to transmit ultrasonic vibration generated by an ultrasonic transducer to the probe distal end body, and to transmit the electric current to the first electrode, and wherein an interior surface of the probe distal end body and an interior surface of the vibration transmission body define an interior space; a heat dissipation unit configured to dissipate heat generated at the probe distal end body, wherein at least a portion of the heat dissipation unit is arranged in the interior space defined by the probe distal end body and the vibration transmission body; and an end effector configured to move relative to the probe distal end body to change a distance between the end effector and the probe distal end body, wherein the end effector comprises a second electrode of the pair of bipolar electrodes, the second electrode being configured to be electrically connected to a second electric path through which the electric current is transmitted.

BRIEF DESCRIPTION OF THE DRAWINGS

FIG. 3 is a side view showing a coupled state between a handle unit and a transducer unit of the ultrasonic therapeutic apparatus according to the first embodiment;

FIG. 5 is a plan view showing a probe unit of the ultrasonic therapeutic apparatus according to the first embodiment;

FIG. 6 is a cross-sectional view taken along line VI-VI in FIG. 5;

FIG. 9B is a cross-sectional view taken along line IXB-IXB in FIG. 9A;

FIG. 17 is a plan view showing an engaged state between the electrode member of the jaw and the probe distal end portion of the ultrasonic therapeutic apparatus according to the first embodiment;

FIG. 18 is a vertical cross-sectional view showing an engaged state between the electrode member of the jaw and the probe distal end portion of the ultrasonic therapeutic apparatus according to the first embodiment;

FIG. 19 is a plan view showing a living body tissue contact surface of the hold member of the jaw of the ultrasonic therapeutic apparatus according to the first embodiment;

FIG. 20 is a plan view showing the probe distal end portion of the ultrasonic therapeutic apparatus according to the first embodiment;

FIG. 31 is a perspective view showing a state after the rotational engagement at the time when the handle unit and sheath unit of the ultrasonic therapeutic apparatus according to the first embodiment are coupled;

FIG. 32 is a plan view showing the state after the rotational engagement at the time when the handle unit and sheath unit of the ultrasonic therapeutic apparatus according to the first embodiment are coupled;

FIG. 36 is a side view showing a state before an attachment member is attached to a base member of a stationary handle of the handle unit of the ultrasonic therapeutic apparatus according to the first embodiment;

FIG. 41A is a vertical cross-sectional view showing a state prior to engagement of the engagement section between the handle unit and sheath unit of the ultrasonic therapeutic apparatus according to the first embodiment;

FIG. 41B is a vertical cross-sectional view showing a state prior to engagement of the engagement section between the handle unit and sheath unit of the ultrasonic therapeutic apparatus according to the first embodiment;

FIG. 42 is a cross-sectional view taken along line 42-42 in FIG. 37;

FIG. 49 is a perspective view showing an electrode member of the ultrasonic therapeutic apparatus according to the first embodiment;

FIG. 50 is a transverse cross-sectional view showing the electrode member of the ultrasonic therapeutic apparatus according to the first embodiment;

FIG. 51 is a cross-sectional view taken along line 51-51 in FIG. 37;

FIG. 55 is a perspective view showing the structure of a jaw of an ultrasonic therapeutic apparatus according to a fourth embodiment of the present invention;

FIG. 56 is a perspective view showing the structure of a jaw of an ultrasonic therapeutic apparatus according to a fifth embodiment of the present invention;

FIG. 59 is a vertical cross-sectional view showing an engagement state between an electrode member of the jaw and a probe distal end portion of the ultrasonic therapeutic apparatus according to the sixth embodiment;

FIG. 60 is a perspective view showing an insulation member of the jaw of the ultrasonic therapeutic apparatus according to the sixth embodiment:

FIG. 61 is a perspective view showing a metallic pad of the jaw of the ultrasonic therapeutic apparatus according to the sixth embodiment;

FIG. 65 is a perspective view showing a first step of bending the metallic plate which is assembled to the insulation member of the jaw of ultrasonic therapeutic apparatus according to the seventh embodiment is bent;

FIG. 80 is a cross-section view schematically showing a probe unit according to a first example of a seventh modification of the first embodiment.

FIG. 81 is a cross-section view schematically showing a probe unit according to a second example of the seventh modification of the first embodiment.

DETAILED DESCRIPTION

Figure 1:
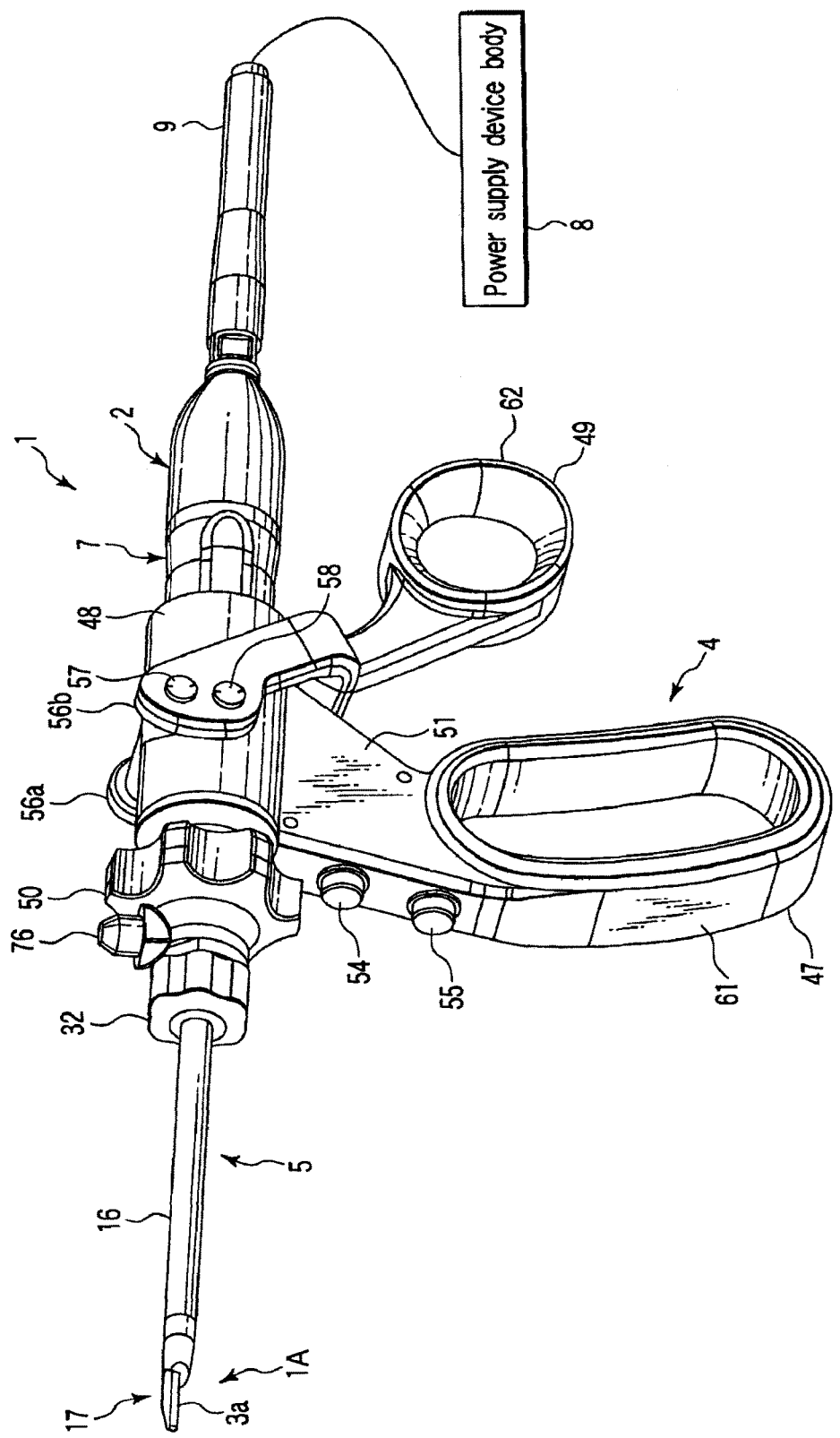
FIG. 1 is a perspective view that schematically shows the entire structure of an ultrasonic therapeutic apparatus according to a first embodiment of the present invention.
Figure 52:
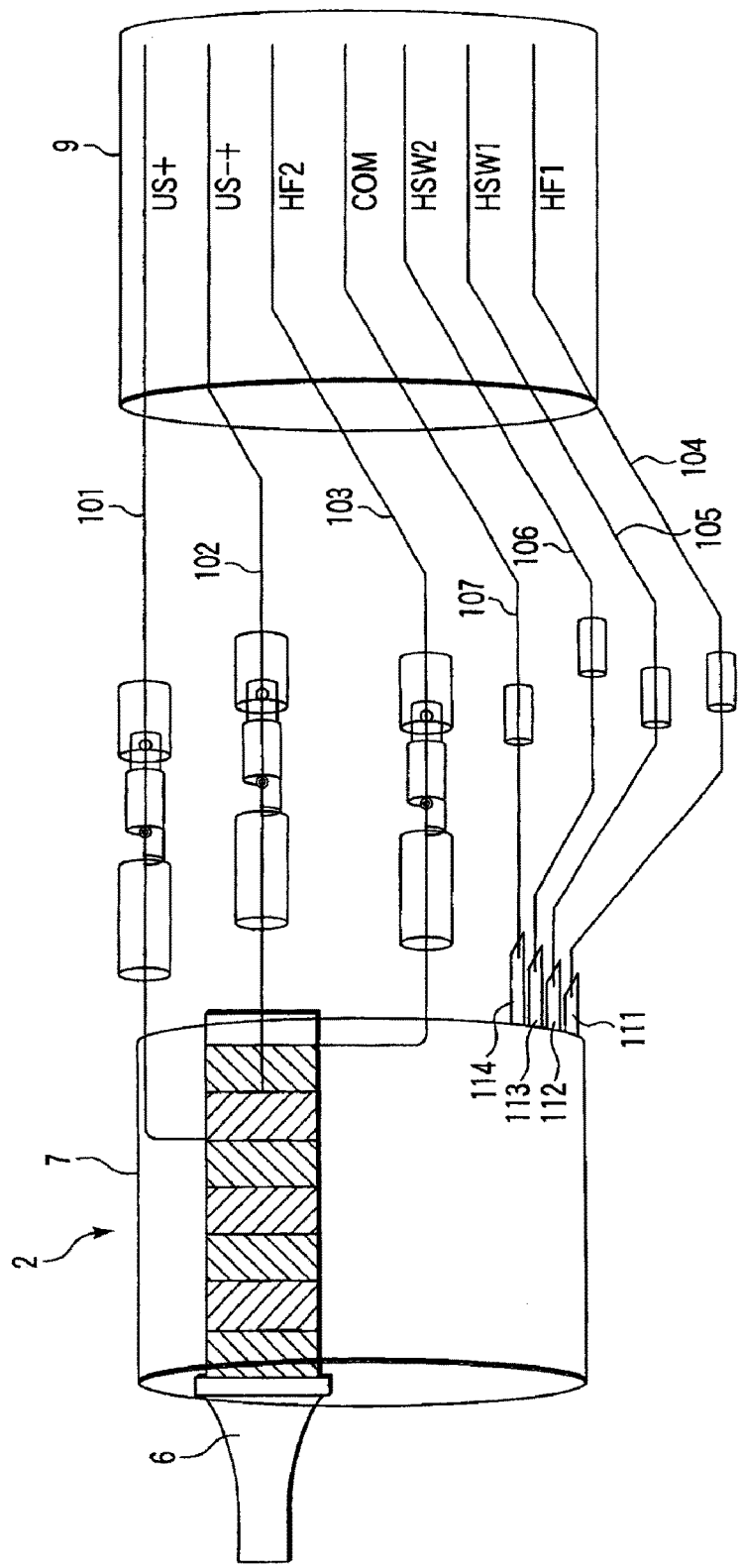
FIG. 52 is a schematic view showing an internal structure of a cable of the transducer unit of the ultrasonic therapeutic apparatus according to the first embodiment.

A first embodiment of the present invention will now be described with reference to FIG. 1 to FIG. 52. FIG. 1 schematically shows the entire structure of a handpiece 1 of an ultrasonic therapeutic apparatus which is a surgical operating apparatus according to the first embodiment. The ultrasonic therapeutic apparatus of the present embodiment is an ultrasonic coagulation/incision apparatus. This ultrasonic coagulation/incision apparatus can perform therapeutic treatment, such as incision, resection or coagulation, of a living body tissue by making use of ultrasound, and can also perform therapeutic treatment by high-frequency waves.

Figure 2:
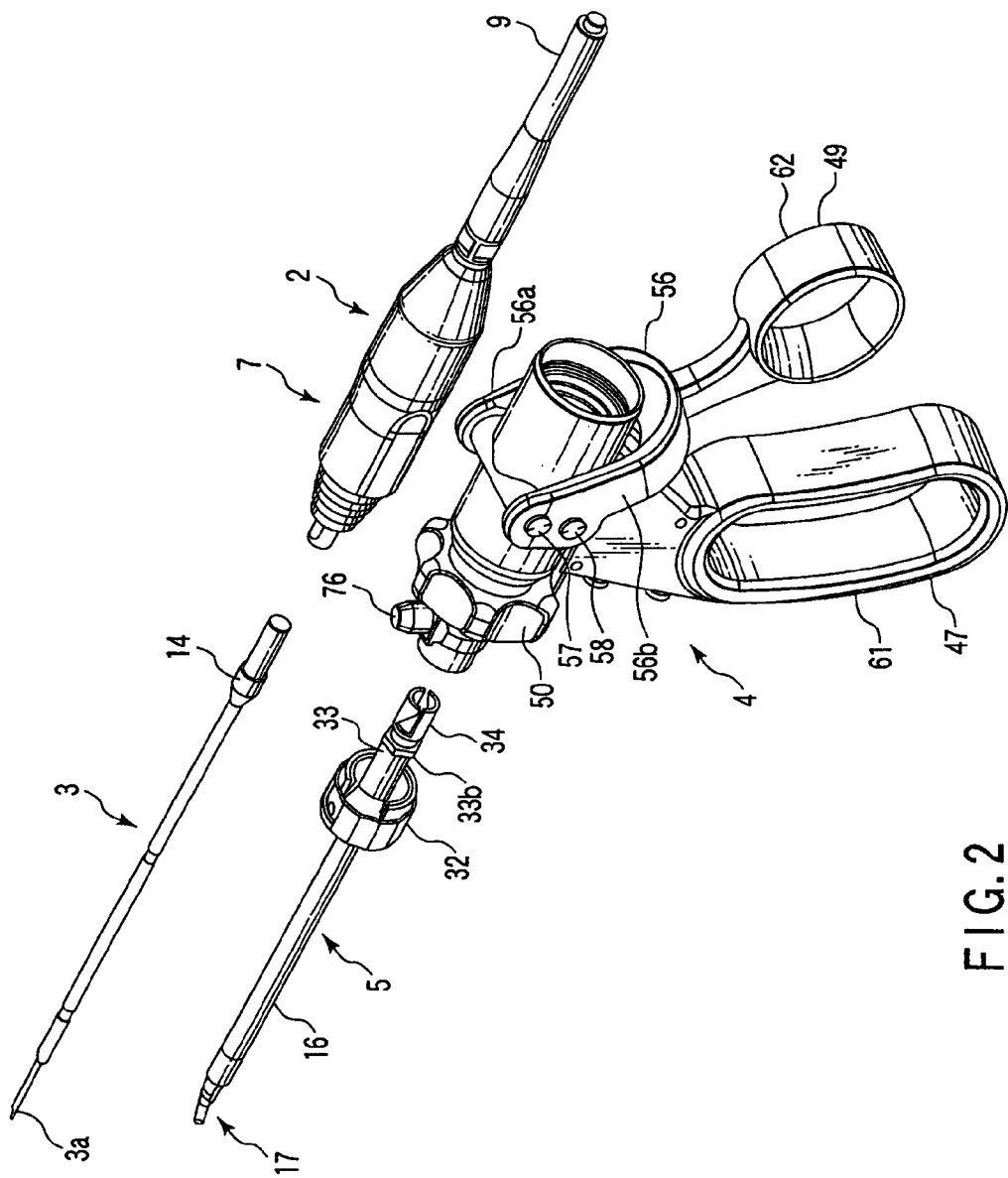
FIG. 2 is a perspective view showing a disassembled state of the ultrasonic therapeutic apparatus according to the first embodiment, with coupling sections of assembly units of the ultrasonic therapeutic apparatus being disconnected.

The handpiece 1, as shown in FIG. 2, comprises four units, namely, a transducer unit 2, a probe unit (probe section) 3, a handle unit (operation section) 4 and a sheath unit (sheath section) 5. These units are detachably coupled.

Figure 4:
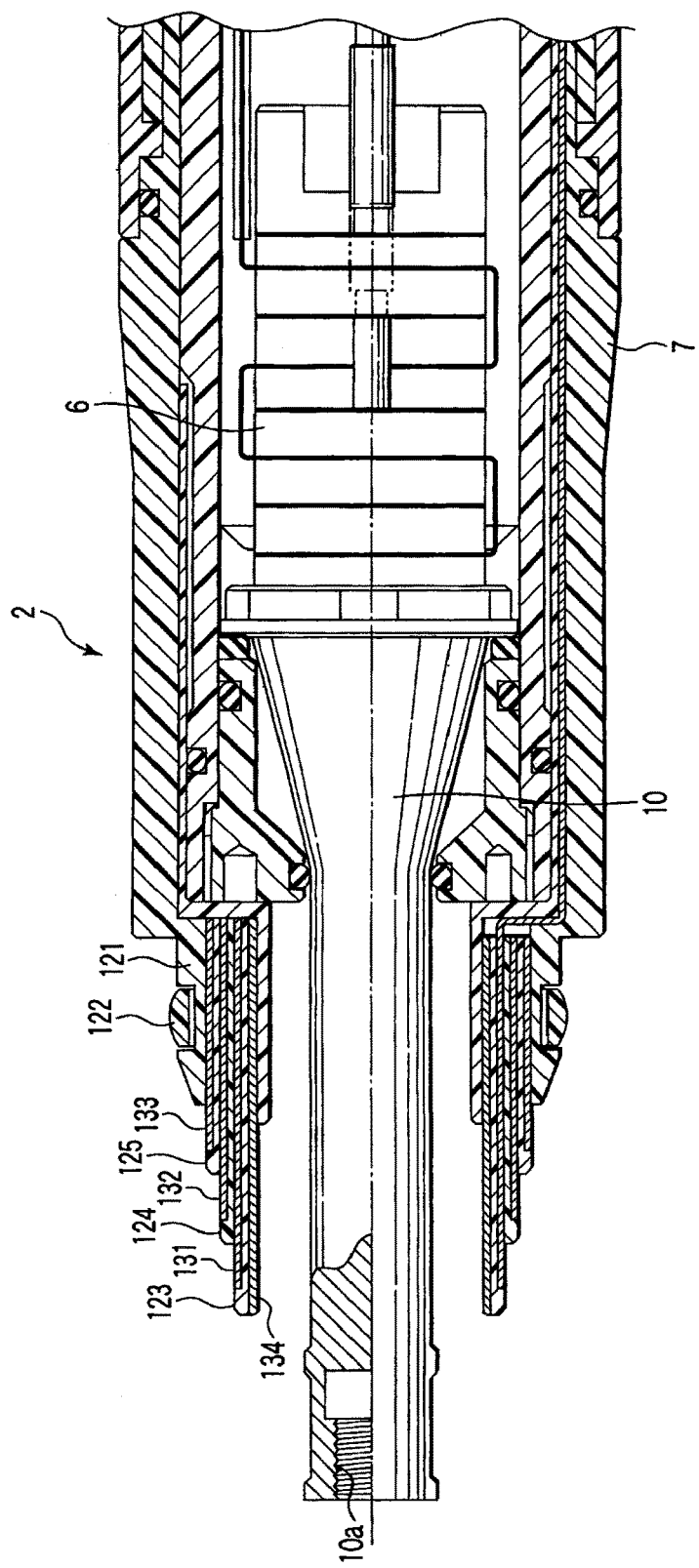
FIG. 4 is a longitudinal cross-sectional view showing an internal structure of the transducer unit of the ultrasonic therapeutic apparatus according to the first embodiment.

As shown in FIG. 4, an ultrasonic transducer 6 for generating ultrasonic vibration by a piezoelectric oscillator, which converts an electric current to ultrasonic vibration, is built in the transducer unit 2. An outside of the ultrasonic transducer 6 is covered with a cylindrical transducer cover 7. As shown in FIG. 1, a cable 9 for supplying an electric current for generating ultrasonic vibration from a power supply device body 8 extends from a rear end of the transducer unit 2.

A proximal end portion of a horn 10, which increases the amplitude of ultrasonic vibration, is coupled to a front end portion of the ultrasonic transducer 6. A screw hole portion 10a for attaching the probe unit 3 is formed at a distal end portion of the horn 10.

FIG. 5 shows the external appearance of the entire probe unit 3. The probe unit 3 is designed such that the entire length thereof may become an integer number of times of half-wave length of the ultrasonic vibration. The probe unit 3 has a distal end and a proximal end defining a longitudinal axis C (see FIGS. 72-81), and includes a metallic rod-shaped vibration transmission member 11 extending along the longitudinal axis C.

A proximal end portion of the vibration transmission member 11 is provided with a screw portion 12 which is to be engaged with the screw hole portion 10a of the horn 10. The screw portion 12 is engaged with the screw hole portion 10a of the horn 10 of the transducer unit 2. Thereby, the probe unit 3 and the transducer unit 2 are assembled.

A probe distal end portion 3a is provided at a distal end portion of the vibration transmission member 11. The probe distal end portion 3a is formed in a substantially J-shaped curved form. The probe distal end portion 3a constitutes a first electrode section which is one of a pair of bipolar electrodes. In a proximal end portion of the probe distal end portion 3a, a screw portion 3a2 is provided. The distal end portion of the vibration transmission member 11 is provided with a screw hole portion 1120 which is to be engaged with the screw portion 3a2 (see FIG. 72).

Upon engagement of the screw hole portion 1120 of the vibration transmission member 11 with the screw portion 3a2 of the probe distal end portion 3a, and engagement of the screw hole portion 10a of the horn 10 with the screw portion 12 of the vibration transmission member 11, a first high-frequency electric path 13, through which a high-frequency current is transmitted, is formed in the coupled body of the ultrasonic transducer 6 and the probe unit 3.

Figure 7:
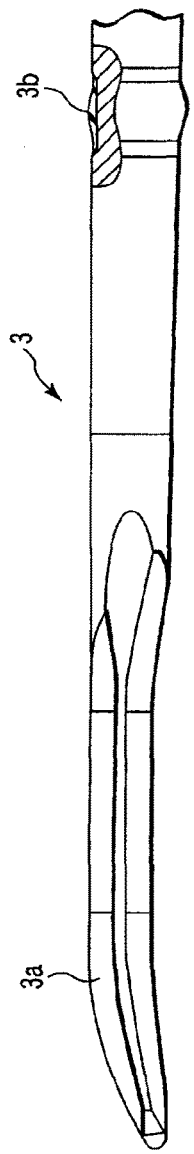
FIG. 7 is a plan view showing a distal end portion of the probe unit of the ultrasonic therapeutic apparatus according to the first embodiment.

The cross-sectional area of the probe unit 3 is decreased in the axial direction at several nodes of vibration in the axial direction, so that an amplitude necessary for therapeutic treatment can be obtained at the probe distal end portion 3a. Rubber rings 3b (see FIG. 7), which are formed of elastic material in an annular shape, are attached to several positions of nodes of vibration along the axial direction of the probe unit 3. The rubber rings 3b prevent interference between the probe unit 3 and the sheath unit 5.

A flange portion 14 is provided at the position of the node of vibration on the most proximal end side in the axial direction of the probe unit 3. As shown in FIG. 6, engaging recess portions 15 each having a key groove shape are formed on the outer peripheral surface of the flange portion 14 at three positions in the circumferential direction thereof.

A first modification of the probe unit 3 will be described below with reference to FIG. 72.

Figure 72:
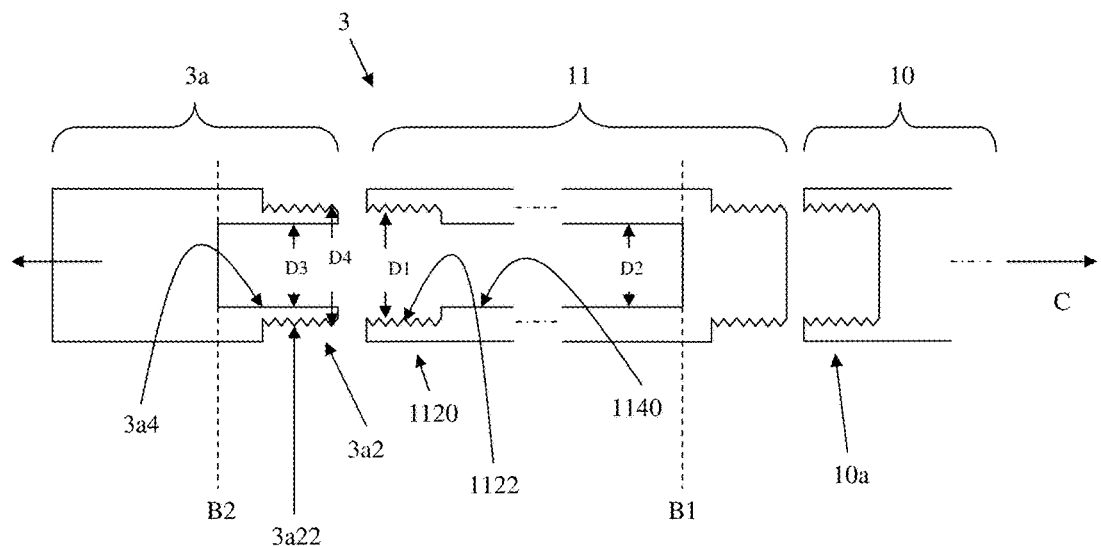
FIG. 72 is a cross-section view schematically showing a probe unit according to a first modification of the first embodiment.

As illustrated in FIG. 72, the vibration transmission member 11 is provided with an inner surface 1140 that defines an interior space extending along the longitudinal axis C of the probe unit 3. The inner surface 1140 extends in a distal direction along the longitudinal axis C to communicate the interior space with the screw hole portion 1120 of the vibration transmission member 11. The inner surface 1140 extends in a proximal direction along the longitudinal axis C and forms a closed end of the interior space at substantially a node position B1 of ultrasonic vibration.

As an example of the communication of the interior space of the vibration transmission member 11 and the screw hole portion 1120 of the vibration transmission member 11, the screw hole portion 1120 is provided with an internal thread portion 1122 that is arranged in a stepped manner with the inner surface 1140. In the stepped arrangement of the screw hole portion 1120 with the inner surface 1140, the internal thread portion 1122 is substantially coaxial with the interior space defined by the inner surface 1140 about the longitudinal axis C, while a radial dimension D1 of the internal thread portion 1122 is greater than a radial dimension D2 of the inner surface 1140.

In the probe distal end portion 3a, an inner surface 3a4 defines an interior space extending along the longitudinal axis C of the probe unit 3. The inner surface 3a4 extends in a distal direction along the longitudinal axis C and forms a closed end of the interior space at a node position B2 of the ultrasonic vibration. The inner surface 3a4 extends in a proximal direction along the longitudinal axis C through the screw portion 3a2 to form an open end of the interior space.

FIG. 72 illustrates an example of the extension of the inner surface 3a4 of the probe distal end portion 3a through the screw portion 3a2 to form an open end of the interior space of the probe distal end portion 3a. The screw portion 3a2 of the probe distal end portion 3a is provided with an external thread portion 3a22 to be screwed into the internal thread portion 1122 of the vibration transmission member 11. The external thread portion 3a22 is substantially coaxial with the interior space defined by the inner surface 3a4 of the probe distal end portion 3a about the longitudinal axis C. A radial dimension D3 of the inner surface 3a4 of the probe distal end portion 3a is substantially the same as the radial dimension D2 of the inner surface 1140 of the vibration transmission member 11 and less than a radial dimension D4 of the external thread portion 3a22 of the probe distal end portion 3a.

Upon engagement of the screw hole portion 1120 of the vibration transmission member 11 with the screw portion 3a2 of the probe distal end portion 3a, the interior space defined by the inner surface 1140 of the vibration transmission member 11 communicates with the interior space defined by the inner surface 3a4 of the probe distal end portion 3a such that a closed space is formed by the inner surface 1140 and the inner surface 3a4.

A second modification of the probe unit 3 will be described below with reference to FIG. 73.

Figure 73:
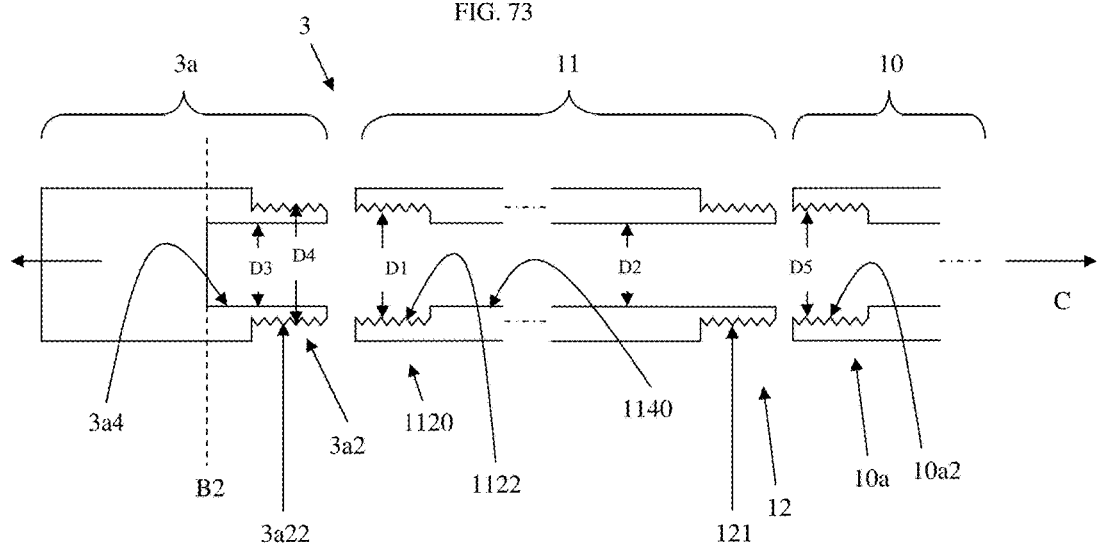
FIG. 73 is a cross-section view schematically showing a probe unit according to a second modification of the first embodiment.

As illustrated in FIG. 73, the vibration transmission member 11 is provided with an inner surface 1140 that defines an interior space extending along the longitudinal axis C of the probe unit 3. The inner surface 1140 extends in a distal direction along the longitudinal axis C to communicate the interior space with the screw hole portion 1120 of the vibration transmission member 11. The inner surface 1140 extends in a proximal direction along the longitudinal axis C through the screw portion 12 to form an open end of the interior space.

An example of the communication of the interior space of the vibration transmission member 11 and the screw hole portion 1120 of the vibration transmission member 11 is described below. The screw hole portion 1120 is provided with an internal thread portion 1122 that is arranged in a stepped manner with the inner surface 1140. In the stepped arrangement of the screw hole portion 1120 with the inner surface 1140, the internal thread portion 1122 is substantially coaxial with the interior space defined by the inner surface 1140 about the longitudinal axis C, while a radial dimension D1 of the internal thread portion 1122 is greater than a radial dimension D2 of the inner surface 1140.

In the probe distal end portion 3a, an inner surface 3a4 defines an interior space extending along the longitudinal axis C of the probe unit 3. The inner surface 3a4 extends in a distal direction along the longitudinal axis C and forms a closed end of the interior space at a node position B2 of the ultrasonic vibration. The inner surface 3a4 extends in a proximal direction along the longitudinal axis C through the screw portion 3a2 to form an open end of the interior space.

FIG. 73 illustrates an example of the extension of the inner surface 3a4 of the probe distal end portion 3a through the screw portion 3a2 to form an open end of the interior space of the probe distal end portion 3a. The screw portion 3a2 of the probe distal end portion 3a is provided with an external thread portion 3a22 to be screwed into the internal thread portion 1122 of the vibration transmission member 11. The external thread portion 3a22 is substantially coaxial with the interior space defined by the inner surface 3a4 of the probe distal end portion 3a about the longitudinal axis C. A radial dimension D3 of the inner surface 3a4 of the probe distal end portion 3a is substantially the same as the radial dimension D2 of the inner surface 1140 of the vibration transmission member 11 and less than a radial dimension D4 of the external thread portion 3a22 of the probe distal end portion 3a.

FIG. 73 illustrates an example of the extension of the inner surface 1140 of the vibration transmission member 11 through the screw portion 12 to form the open end of the interior space of the vibration transmission member 11. The screw portion 12 of the vibration transmission member 11 is provided with an external thread portion 121 to be screwed into an internal thread portion 10a2 of the screw hole portion 10a of the horn 10. The external thread portion 121 is substantially coaxial with the interior space defined by the inner surface 1140 of the vibration transmission member 11 about the longitudinal axis C. The radial dimension D2 of the inner surface 1140 of the vibration transmission member 11 is less than a radial dimension D5 of the internal thread portion 10a2 of the screw portion 12.

Upon engagement of the screw hole portion 1120 of the vibration transmission member 11 with the screw portion 3a2 of the probe distal end portion 3a, the interior space defined by the inner surface 1140 of the vibration transmission member 11 communicates with the interior space defined by the inner surface 3a4 of the probe distal end portion 3a such that a space is formed by the inner surface 1140 and the inner surface 3a4.

A third modification of the probe unit 3 will be described below with reference to FIG. 74.

In the fourth modification, the probe distal end portion 3a and the vibration transmission member 11 are formed as a single integral piece.

Figure 74:
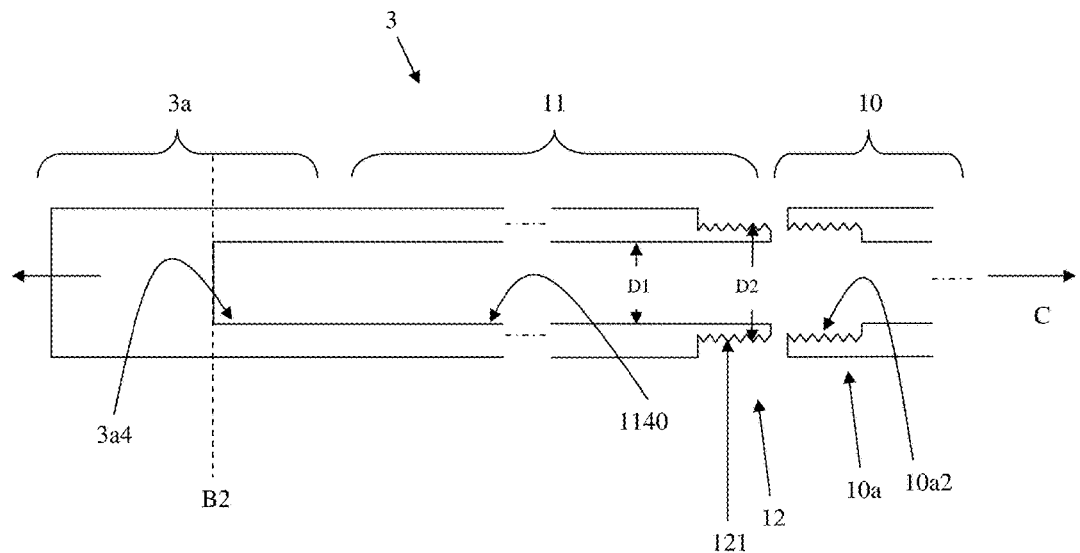
FIG. 74 is a cross-section view schematically showing a probe unit according to a third modification of the first embodiment.

As illustrated in FIG. 74, the vibration transmission member 11 is provided with an inner surface 1140 that defines an interior space extending along the longitudinal axis C of the probe unit 3 and the probe distal end portion 3a is provided with an inner surface 3a4 that defines an interior space extending along the longitudinal axis C of the probe unit 3.

The inner surface 3a4 of the probe distal end portion 3a extends in a distal direction along the longitudinal axis C to form a closed end. The inner surface 3a4 of the probe distal end portion 3a extends in a proximal direction along the longitudinal axis C to meet the inner surface 1140 of the vibration transmission member 11. The inner surface 1140 of the vibration transmission member 11 extends in a proximal direction along the longitudinal axis C through the screw portion 12 to form an open end of the interior space.

FIG. 74 illustrates an example of the extension of the inner surface 1140 of the vibration transmission member 11 through the screw portion 12 to form the open end of the interior space of the vibration transmission member 11. The screw portion 12 of the vibration transmission member 11 is provided with an external thread portion 121 to be screwed into an internal thread portion 10a2 of the screw hole portion 10a of the horn 10. The external thread portion 121 is substantially coaxial with the interior space defined by the inner surface 1140 of the vibration transmission member 11 about the longitudinal axis C. The radial dimension D1 of the inner surface 1140 of the vibration transmission member 11 is less than a radial dimension D2 of the external thread portion 121 of the screw portion 12.

Compatible with the second and third modifications of the probe unit 3, the horn 10 can be provided with a passage portion about the longitudinal axis C from the screw hole portion 10a to the proximal end of the horn 10, and the ultrasonic transducer 6 can be provided with a passage portion about the longitudinal axis C. The passage portion of the horn 10 and the passage portion of the ultrasonic transducer 6 can be coaxial with the interior space defined by the inner surface 1140 of the vibration transmission member 11 and the interior space defined by the inner surface 3a4 of the probe distal end portion 3a.

A fourth modification of the probe unit 3 will be described below with reference to FIG. 75.

Figure 75:
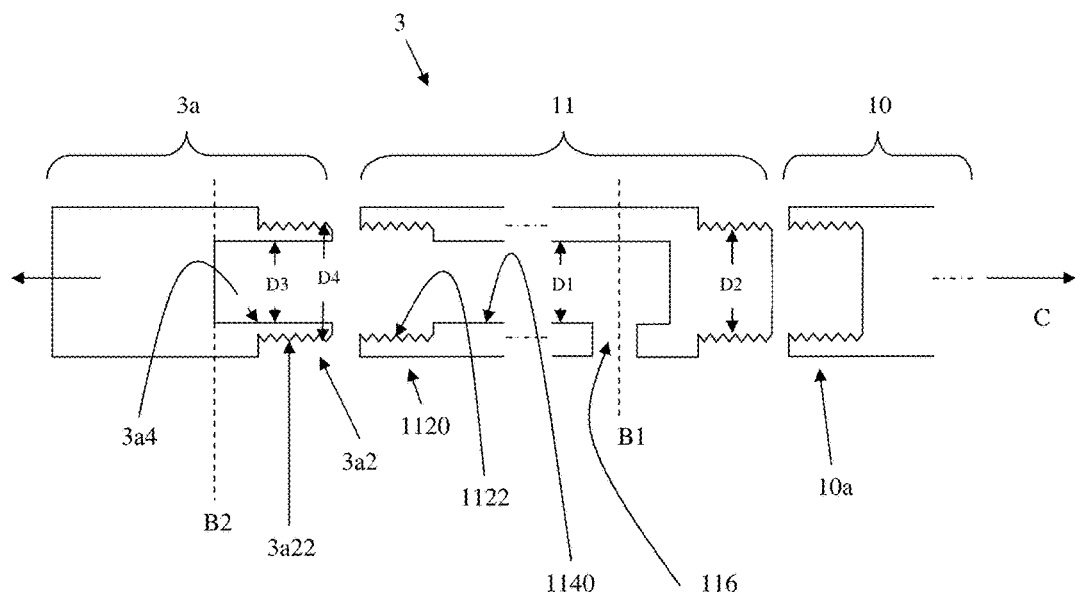
FIG. 75 is a cross-section view schematically showing a probe unit according to a fourth modification of the first embodiment.

As illustrated in FIG. 75, the vibration transmission member 11 is provided with an inner surface 1140 that defines an interior space extending along the longitudinal axis C of the probe unit 3. The inner surface 1140 extends in a distal direction along the longitudinal axis C to communicate the interior space with the screw hole portion 1120 of the vibration transmission member 11. The inner surface 1140 extends in a proximal direction along the longitudinal axis C and forms a closed end of the interior space in the vicinity of the screw portion 12.

In the vibration transmission member 11, the screw hole portion 1120 is provided with an internal thread portion 1122 that is arranged in a stepped manner with the inner surface 1140 of the vibration transmission member 11. In the stepped arrangement of the screw hole portion 1120 with the inner surface 1140, the internal thread portion 1122 is substantially coaxial with the interior space defined by the inner surface 1140 about the longitudinal axis C, while a radial dimension D1 of the internal thread portion 1122 is greater than a radial dimension D2 of the inner surface 1140.

In the probe distal end portion 3a, an inner surface 3a4 defines an interior space extending along the longitudinal axis C of the probe unit 3. The inner surface 3a4 extends in a distal direction along the longitudinal axis C and forms a closed end of the interior space at a node position B2 of the ultrasonic vibration. The inner surface 3a4 extends in a proximal direction along the longitudinal axis C through the screw portion 3a2 to form an open end of the interior space.

In the probe distal end portion 3a, the screw portion 3a2 of the probe distal end portion 3a is provided with an external thread portion 3a22 to be screwed into the internal thread portion 1122 of the vibration transmission member 11. The external thread portion 3a22 is substantially coaxial with the interior space defined by the inner surface 3a4 of the probe distal end portion 3a about the longitudinal axis C. A radial dimension D3 of the inner surface 3a4 of the probe distal end portion 3a is substantially the same as the radial dimension D1 of the inner surface 1140 of the vibration transmission member 11 and less than a radial dimension D4 of the external thread portion 3a22 of the probe distal end portion 3a.

Further, a through port 116 connecting the inner surface 1140 of the vibration transmission member 11 and an external surface of the vibration transmission member 11 is provided at a node position B1 of the ultrasonic vibration. The node position B1 is proximal to the node position B2 and positioned along the longitudinal axis C in the vibration transmission member 11 to be closer to the screw portion 12 than to the screw hole portion 1120.

In the first to fourth modifications of the probe unit 3 described above, various material and combination of materials are contemplated. In a first example, both the probe distal end portion 3a and the vibration transmission member 11 can be formed of a titanium alloy. In a second example, both the probe distal end portion 3a and the vibration transmission member 11 can be formed of stainless steel. In a third example, the probe distal end portion 3a can be formed of a titanium alloy and the vibration transmission member 11 can be formed of stainless steel. In the third example, for a probe unit 3 that is approximately 430 mm in length along the longitudinal axis C and approximately 15 grams in weight, the vibration transmission member 11 formed of stainless steel can be approximately 9 grams in weight and a radial thickness of the vibration transmission member 11 from the outer surface of the vibration transmission member 11 to the inner surface 1140 of the vibration transmission member 11 is approximately 0.012 inches and within a range of 0.010 inches and 0.015 inches.

A conventional vibration transmission member can be constructed as a solid titanium alloy rod. In contrast, in the second and third example, the vibration transmission member 11 is constructed of stainless steel. In selecting stainless steel as a replacement material, it is contemplated that the resulting vibration transmission member 11 has a same or substantially same weight as the conventional vibration transmission member, the resulting vibration transmission member 11 has a same or substantially same strength to sustain mechanical loads as the conventional vibration transmission member, and the resulting vibration transmission member 11 has a same or substantially same outer diameter as the conventional vibration transmission member.

In the case of keeping the weight of the vibration transmission member 11 the same as the conventional vibration transmission member, as well keeping the outer diameter of the vibration transmission member 11 the same as the outer diameter of the conventional vibration transmission member, the following formula can be used to calculate the radial thickness (Wall Thickness$_{tube}$) of the vibration transmission member 11:

$$\text{Wall Thickness}_{tube} = D(1-(1-\rho_1/\rho_2)^{0.5}),$$

where:
D is the outer diameter of the conventional vibration transmission member,
$\rho_1$ is the density of the titanium alloy of the conventional vibration transmission member, and
$\rho_2$ is the density of the stainless steel selected for the vibration transmission member.

Selection of other material or materials for forming the probe distal end portion 3a and the vibration transmission member 11 is contemplated. Factors that can be considered in the selection of material or materials for forming the probe distal end portion 3a and the vibration transmission member 11 will be described below. The material or materials can be selected based on the ultrasonic energy transmission requirements of the probe unit 3. Further, the material or materials can be selected based on the electric conductivity requirements of the probe unit 3.

As a variation of the first to fourth modifications of the probe unit 3, it is also contemplated that the vibration transmission member 11 can be formed from a plurality of segments connected in series by, for example, welding, to result in a structure substantially the same as the vibration transmission member 11 described above in the first to fourth modifications.

Figure 76:
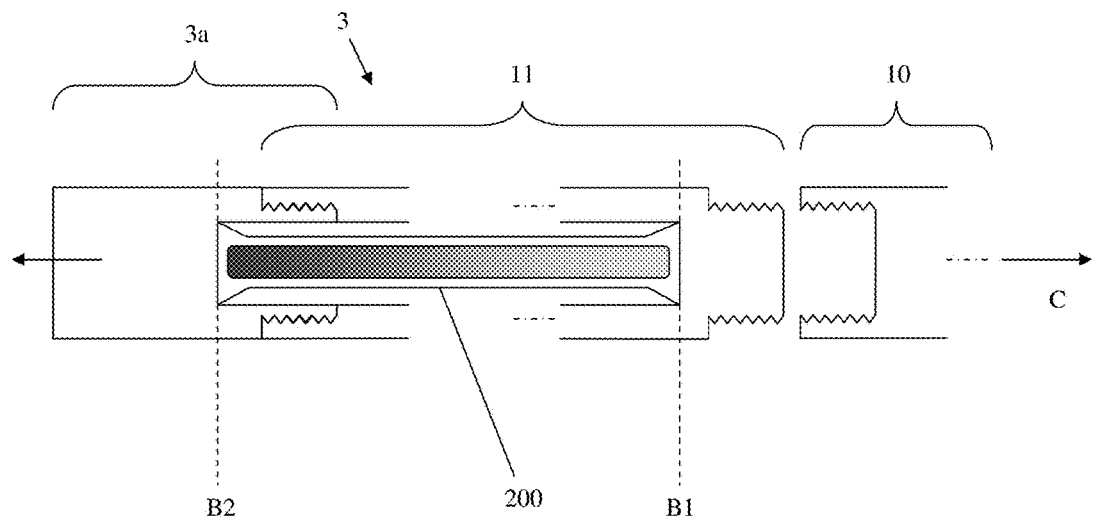
FIG. 76 is a cross-section view schematically showing a probe unit according to a first example of a fifth modification of the first embodiment.

A fifth modification of the probe unit 3 will be described below with reference to FIG. 76.

The fifth modification of the probe unit 3 incorporates a heat pipe 200. The heat pipe 200 can include a tube that is partially filled with a working fluid and then sealed. The sealed tube can be composed of a heat conduction material such as copper or silver that is stable enough to be configured to allow the sealed tube to hold a vacuum. The working fluid mass is chosen so that the heat pipe 200 contains both vapor and liquid over the operating temperature range of the probe unit 3. Examples of the working fluid include water or an alcohol.

Heat energy which is conducted into the distal end portion of the heat pipe 200 causes the internal evaporation of the working fluid of heat pipe 200 and its subsequent recondensation in the cooler regions of heat pipe 200 at positions proximal to the distal end portion of the heat pipe 200.

Heat pipe 200 can further include an internal wick structure to return the recondensed working fluid to the distal end portion of the heat pipe 200. An example of the internal wick structure is sintered metal powder lining the inner surface of the sealed tube along the length of the sealed tube. The recondensed working fluid in the heat pipe 200 is drawn along the length of the tube by capillary action of the porous sintered metal lining the inner surface of the enclosed tube toward the distal end portion of the sealed tube. Another example of the internal wick structure is grooves formed on the inner surface of the sealed tube along the length of the sealed tube. The recondensed working fluid in the heat pipe 200 is drawn along the length of the grooves by capillary action toward the distal end portion of the sealed tube. Another example of the internal wick structure is a metal mesh wick arranged along the inner surface of the enclosed tube. The recondensed working fluid in the heat pipe 200 is drawn along the length of the tube by the capillary action of the metal mesh wick toward the distal end portion of the sealed tube.

A first example of the probe unit 3 according to the fifth modification will be described below with reference to FIG. 76.

In the first example, the heat pipe 200 is provided within the probe unit 3 described in the first modification. Specifically, the heat pipe 200 is arranged in the closed space formed by the interior space defined by the inner surface 1140 of the vibration transmission member 11 and the interior space defined by the inner surface 3a4 of the probe distal end portion 3a.

In the first example, the distal end portion of the heat pipe 200 can be attached to the inner surface 3a4 of the probe distal end portion 3a at the node position B2 and the proximal end portion of the heat pipe 200 can be attached to the inner surface of the vibration transmission member 11 at the node position B1.

At node positions B1, B2 of the ultrasonic vibration, the stress in the directions perpendicular to the longitudinal axis C is maximized, but the displacement due to ultrasonic vibration becomes zero. Therefore, by attaching the distal end portion and the proximal end portion of the heat pipe 200 to the inner surface 1140 at node position B1 and the inner surface 3a4 at node position B2, the heat pipe 200 is not easily influenced by the ultrasonic vibration. As a result, the heat pipe 200 is prevented from being damaged.

Figure 77:
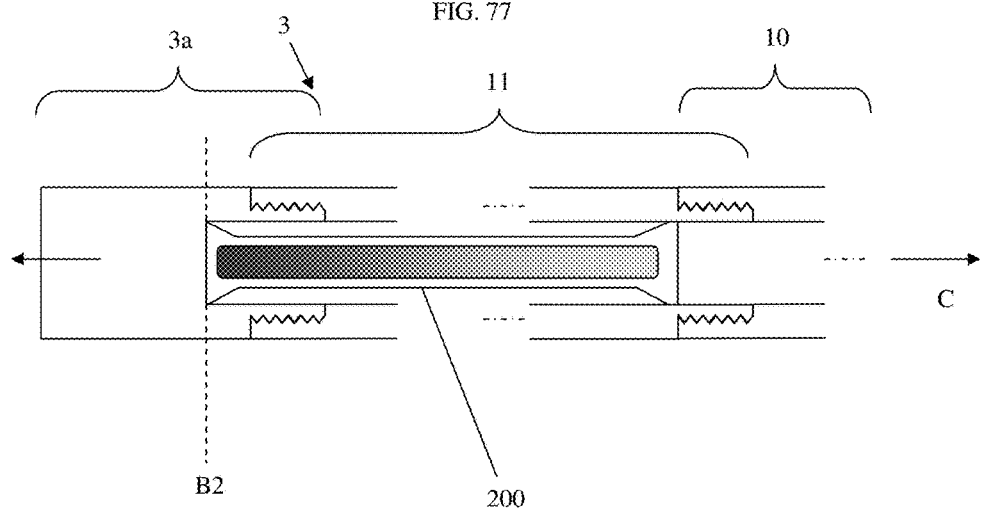
FIG. 77 is a cross-section view schematically showing a probe unit according to a second example of the fifth modification of the first embodiment.

A second example of the probe unit 3 according to the fifth modification will be described below with reference to FIG. 77.

In the second example, the heat pipe 200 is provided within the probe unit 3 described in the second modification. Specifically, the heat pipe 200 is arranged in the space formed by the interior space defined by the inner surface of the vibration transmission member 11 and the interior space defined by the inner surface 200 of the probe distal end portion 3a.

The heat pipe 200 can extend proximally along the longitudinal axis C past the open end of the interior space of the vibration transmission member 11 and into one or both of the passage portion of the horn 10 and the passage portion of the ultrasonic transducer 6.

In the second example, the heat pipe 200 can be attached at a distal end portion along the longitudinal axis C to the inner surface 3a4 of the probe distal end portion 3a at the node position B2 and can be attached at a proximal end portion along the longitudinal axis C to the inner surface of the vibration transmission member 11 at another node position.

Figure 78:
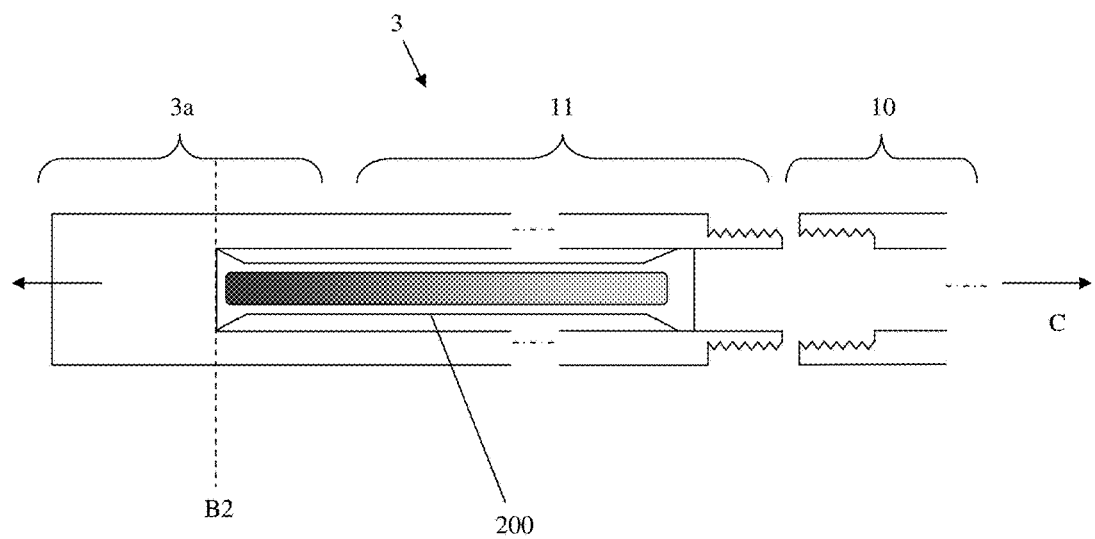
FIG. 78 is a cross-section view schematically showing a probe unit according to a third example of the fifth modification of the first embodiment.

A third example of the probe unit according to the fifth modification will be described below with reference to FIG. 78.

In the third example, the heat pipe 200 is provided within the probe unit 3 described in the third modification. Specifically, the heat pipe 200 is arranged in the space formed by the interior space defined by the inner surface 1140 of the vibration transmission member 11 and the interior space defined by the inner surface 3a4 of the probe distal end portion 3a.

The heat pipe 200 can extend proximally along the longitudinal axis C past the open end of the interior space of the vibration transmission member 11 and into one or both of the passage portion of the horn 10 and the passage portion of the ultrasonic transducer 6.

In the third example, a distal end portion of the heat pipe 200 can be attached to the inner surface 3a4 of the probe distal end portion 3a at the node position B2 and a proximal end portion of the heat pipe 200 can be attached to the inner surface 1140 of the vibration transmission 11 at another node position.

Figure 79:
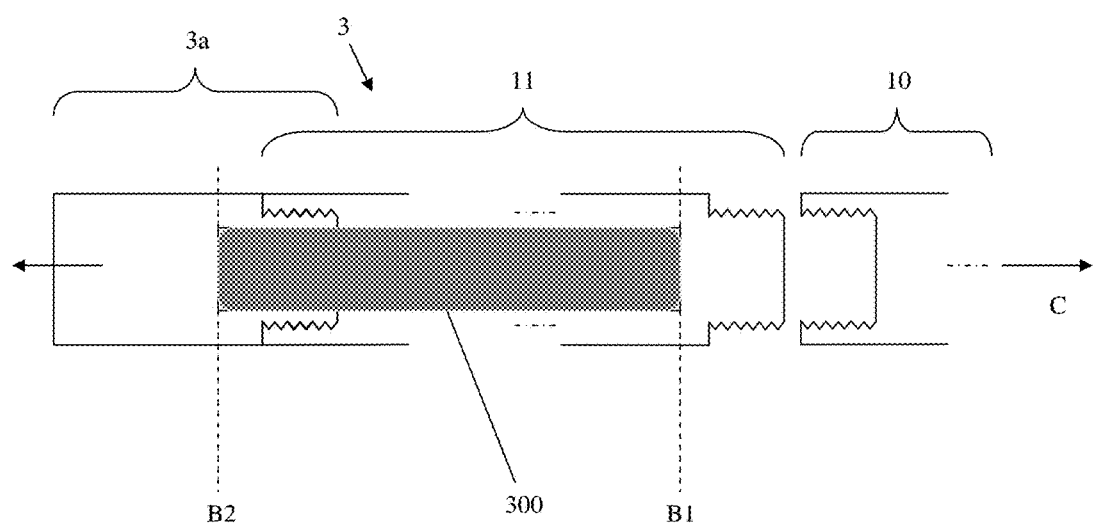
FIG. 79 is a cross-section view schematically showing a probe unit according to a sixth modification of the first embodiment.

A sixth modification of the probe unit 3 will be described below with reference to FIG. 79.

The sixth modification of the probe unit 3 incorporates a thermal dissipating core material 300 such as graphite. Other thermal conducting material such as copper, silver and gold can be selected as the thermal dissipating core material 300.

In an example of probe unit 3 according to the sixth modification, the thermal dissipating core material 300 is provided within the probe unit 3 described in the first modification.

The thermal dissipating core material 300 can be arranged in the closed space formed by the interior space defined by the inner surface 1140 of the vibration transmission member 11 and the interior space defined by the inner surface 3a4 of the probe distal end portion 3a. Specifically, the thermal dissipating core material 300 can be formed in a rod shape that conforms to the inner surface 1140 of the vibration transmission member 11 and the inner surface 3a4 of the probe distal end portion 3a.

Heat energy which is conducted into the distal end portion of the thermal dissipating core material 300 is dissipated by the thermal dissipating core material 300 at a portion proximal to the distal end portion of the thermal dissipating core material 300.

A seventh modification of the probe unit 3 will be described below with reference to FIG. 80.

In the seventh modification, a closed loop coolant circulation system 400 is provided. The closed loop coolant circulation system 400 can include a coolant tubing 420, a coolant pump 440, and a heat exchanger 460.

The coolant tubing 420 includes an input tubing segment 422, an output tubing segment 424, and a heat exchange tubing segment 426. The input tubing segment 422 is arranged within the interior space of the vibration transmission member 11 and the interior space of the probe distal end portion 3a. The input tubing segment 422 passes an inflow of coolant through the interior space of the vibration transmission member 11 and into the interior space of the probe distal end portion 3a. The input tubing segment 422 is in thermal contact with the probe distal end portion 3a to pick up heat from the probe distal end portion 3a. The output tubing segment 424 is arranged within the interior space of the probe distal end portion 3a and the interior space of the vibration transmission member 11. The output tubing segment 424 passes an outflow of heated coolant through the interior space of the probe distal end portion 3a and through the interior space of the vibration transmission member 11. The coolant pump 440 is connected at an input end to the output tubing segment 424 and at an output end to the heat exchange tubing segment 426. The coolant pump 440 pumps the heated coolant from the output tubing segment 424 to the heat exchange tubing segment 426. The heat exchange tubing segment 426 connects the coolant pump 440 to the heat exchanger 460 in the form of coolant flow. As the coolant pump 440 operates, it causes the coolant to flow through heat exchanger 460, along input tubing segment 422, through the probe distal end portion 3a, back through output tubing segment 424, and finally back to the coolant pump 440 for another cycle.

The coolant pump 440 may be powered electrically, mechanically or pneumatically. The heat exchanger 460 can be a liquid-to-air heat exchanger. In the liquid-to-air heat exchanger, coolant is flowed inside of the heat exchanger 460 and air on the outside of heat exchanger 460 carries the heat away. The air on the outside of the heat exchanger 460 can be naturally convected or forced across heat exchanger 460. Examples of the heat exchanger 460 include a radiator or a combination of a fan and the radiator.

A first example of the probe unit 3 according to the seventh modification will be described below with reference to FIG. 80.

In the first example, the closed loop coolant circulation system 400 is provided within the probe unit 3 described in the second modification or the third modification.

In the first example, the input tubing segment 422 is arranged to be in thermal contact with the probe distal end portion 3a. Further, the input tubing segment 422 and the output tubing segment 424 extend proximally through the open end of the interior space of the vibration transmission member 11 and the heat exchange tubing segment 426, the coolant pump 440 and the heat exchanger 460 are arranged on the exterior of the probe unit 3.

A second example of the probe unit 3 according to a seventh modification will be described below with reference to FIG. 81. In the second example, the closed loop coolant circulation system 400 is provided within the probe unit 3 described in the fourth modification.

In the second example, the input tubing segment 422 is arranged to be in thermal contact with the probe distal end portion 3a. Further the input tubing segment 422 and the output tubing segment 424 extend proximally in the interior space of the vibration transmission member 11 and through the through port 116 to the exterior of the probe unit 3. Specifically, the input tubing segment 422 and the output tubing segment 424 are bent from a direction substantially parallel to the longitudinal axis C to a direction substantially perpendicular to the longitudinal axis C at the through port 116. As discussed above, the through port 116 is provided at the node position B1 of the ultrasonic vibration. At the node position B1, stress in the directions perpendicular to the longitudinal axis C is maximized, but displacement due to ultrasonic vibration becomes zero. Therefore, when the input tubing segment 422 and the output tubing segment 424 are bent at the node position B1, the bent portion of the input tubing segment 422 and the bent portion of the output tubing segment 424 are not easily influenced by the ultrasonic vibration. Therefore, the input tubing segment 422 and the output tubing segment 424 are effectively prevented from being damaged by the ultrasonic vibration.

Figure 8B:
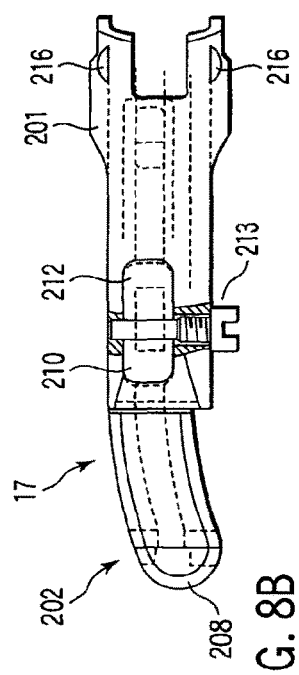
FIG. 8B is a plan view showing a jaw of the sheath unit of the ultrasonic therapeutic apparatus according to the first embodiment.
Figure 8A:
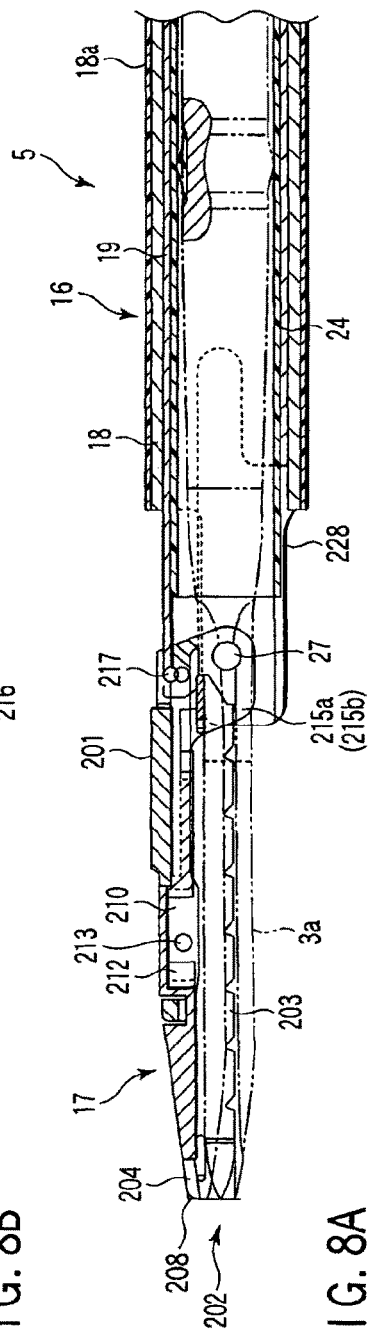
FIG. 8A is a longitudinal cross-sectional view showing a distal end portion of a sheath unit of the ultrasonic therapeutic apparatus according to the first embodiment.
Figure 9A:
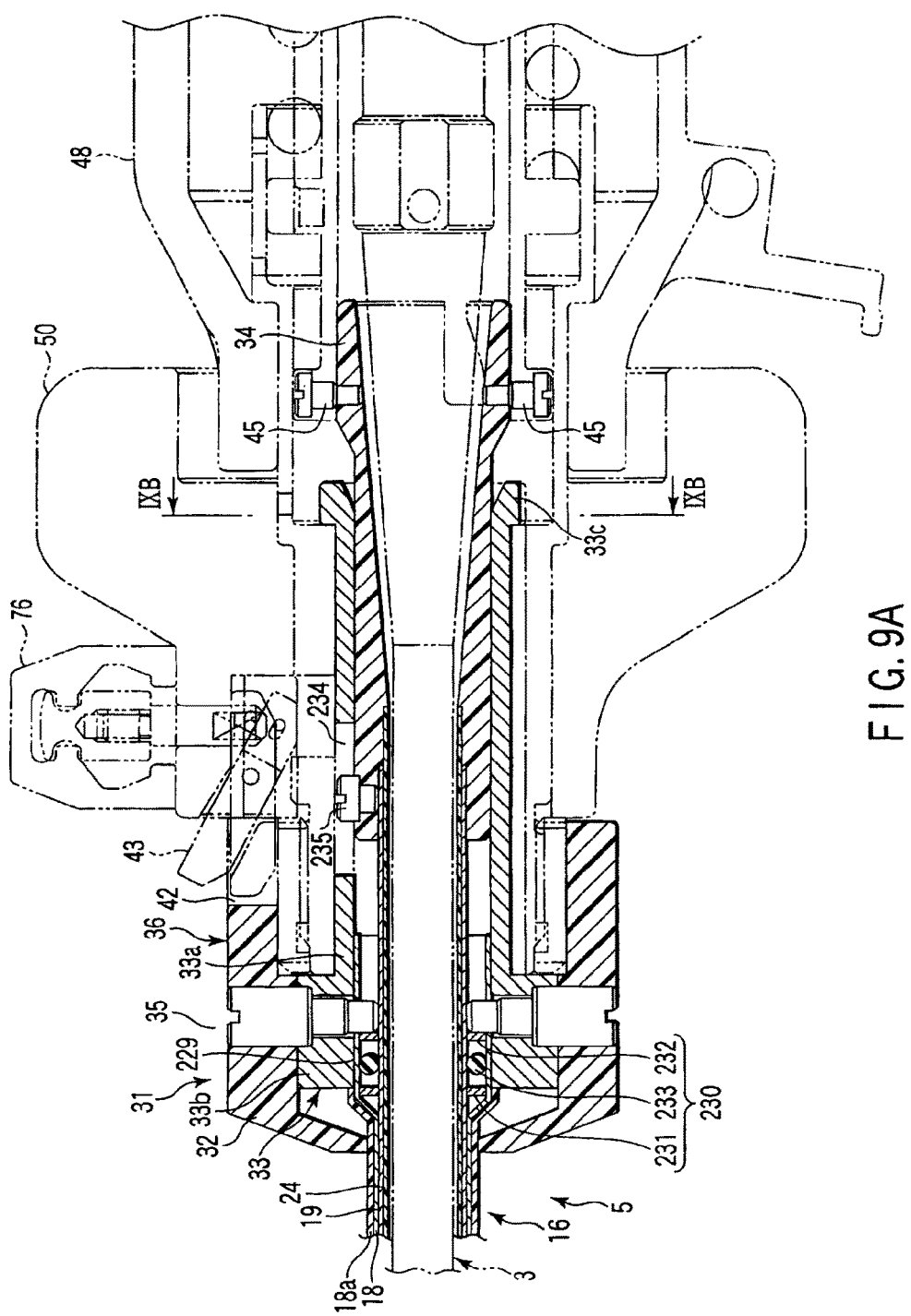
FIG. 9A is a longitudinal cross-sectional view showing a proximal end portion of the sheath unit of the ultrasonic therapeutic apparatus according to the first embodiment.

FIG. 8A shows a distal end portion of the sheath unit 5, and FIG. 9A shows a proximal end portion of the sheath unit 5. As shown in FIG. 8A, the sheath unit 5 includes a sheath body 16, which is formed of a cylindrical body, and a jaw 17 which is provided at a distal end of the sheath body 16. The sheath body 16 includes a metallic sheath 18 which is an outer cylinder, and a metallic driving pipe 19 which is an inner cylinder. The driving pipe 19 is axially movably inserted in the sheath 18.

As shown in FIG. 8A, the outer peripheral surface of the sheath 18 is covered with an outer coating 18a which is formed of an insulating material such as a resin. An insulation tube 24, which is formed of an insulating material, is provided on the inner peripheral side of the driving pipe 19.

Figure 10:
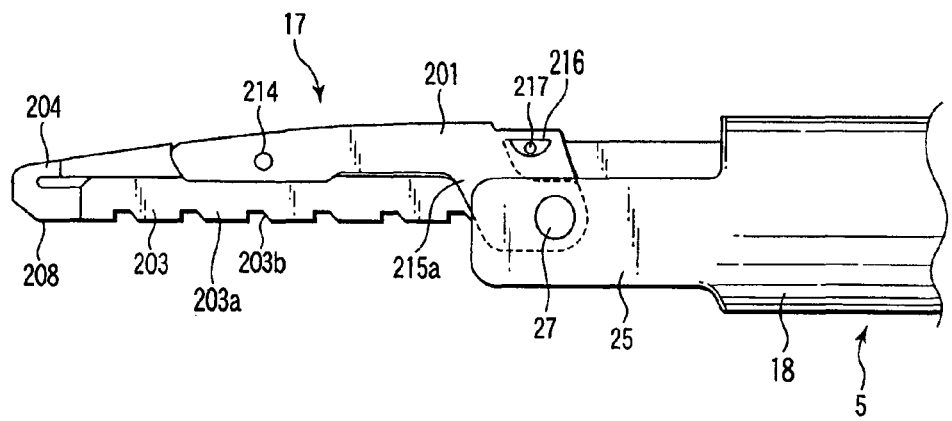
FIG. 10 is a side view showing an attachment section of the jaw of the ultrasonic therapeutic apparatus according to the first embodiment.
Figure 11:
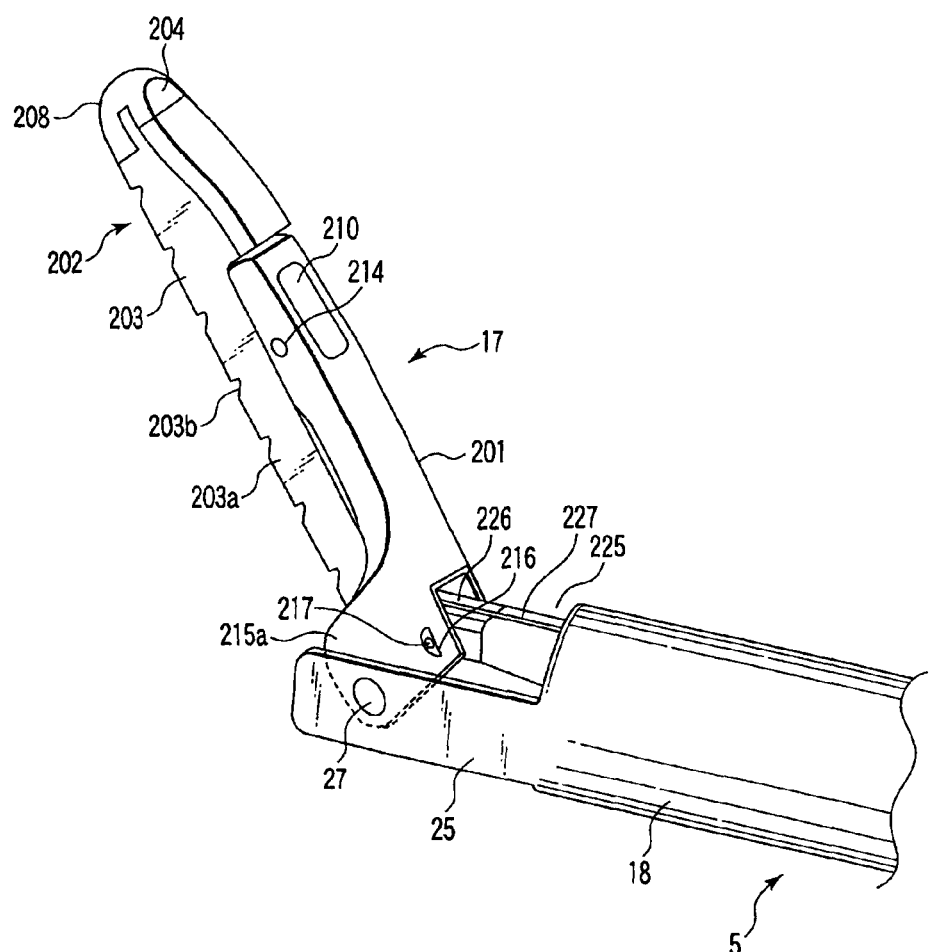
FIG. 11 is a perspective view showing a state in which the jaw of the ultrasonic therapeutic apparatus according to the first embodiment is opened.
Figure 12:
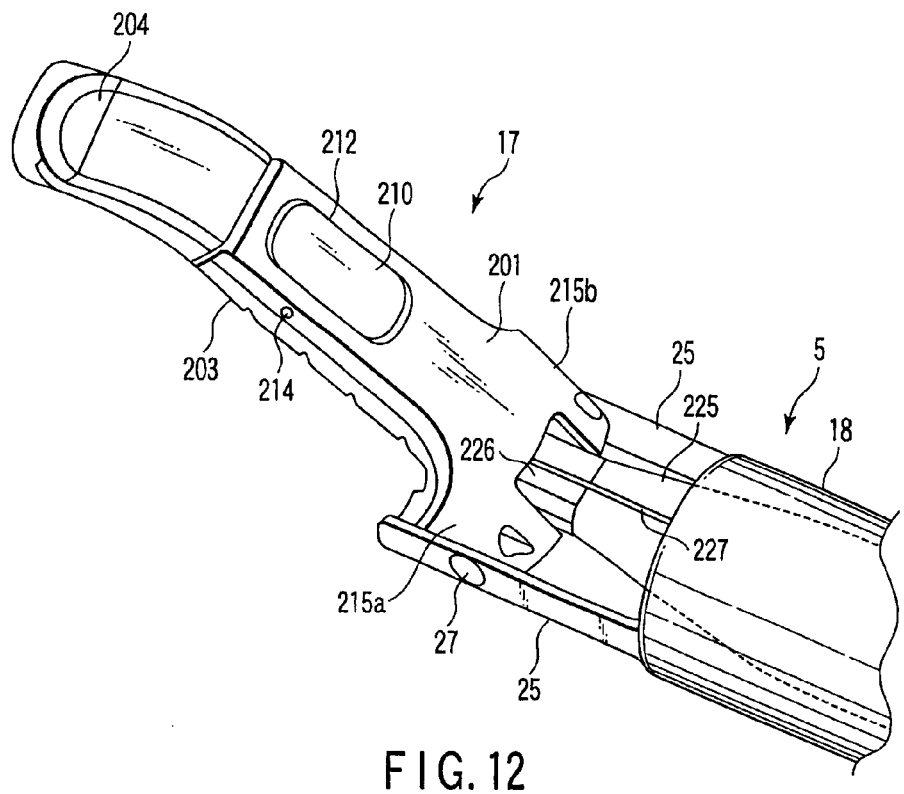
FIG. 12 is a perspective view showing, in a direction different from the direction in FIG. 11, the state in which the jaw of the ultrasonic therapeutic apparatus according to the first embodiment is opened.
Figure 13:
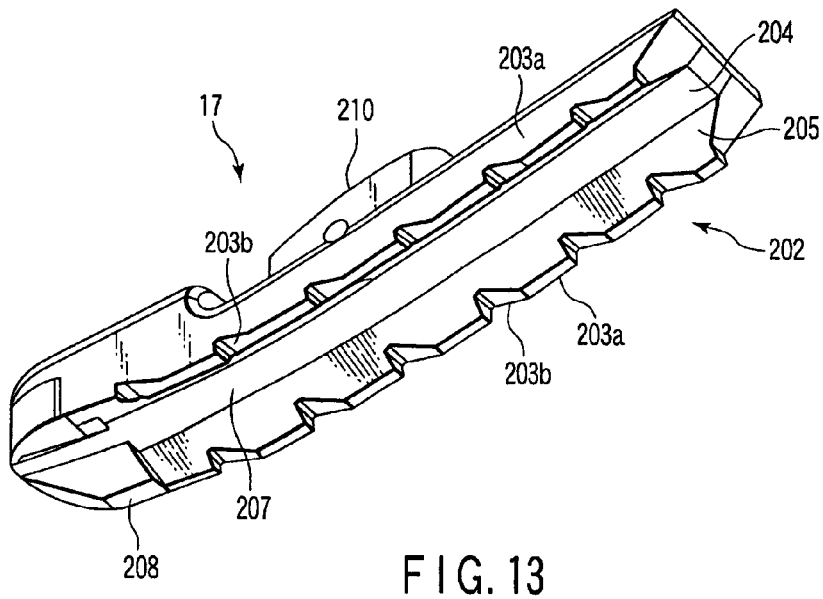
FIG. 13 is a perspective view showing a hold member of the jaw of the ultrasonic therapeutic apparatus according to the first embodiment.

As shown in FIGS. 10 to 12, a pair of right and left projection portions 25 are provided at a distal end portion of the sheath 18 so as to project in a forward direction of the sheath 18. A proximal end portion of the jaw 17 is rotatably attached to the projection portions 25 via a support pin 27. When the probe unit 3 and the sheath unit 5 are assembled, the jaw 17 is positioned to be opposed to the probe distal end portion 3*a* of the probe unit 3.

As shown in FIG. 8B, the jaw 17 is formed in a substantially J-shaped curved form, which corresponds to the curved shape of the probe distal end portion 3*a*, in accordance with the curved shape of the probe distal end portion 3*a* of the probe unit 3. The jaw 17 is configured to be rotated about the support pin 27 by the advancing/retreating movement of the driving pipe 19 in the axial direction. A therapeutic section 1A of the handpiece 1 is constituted by the jaw 17 and the probe distal end portion 3*a*.

Figure 14:
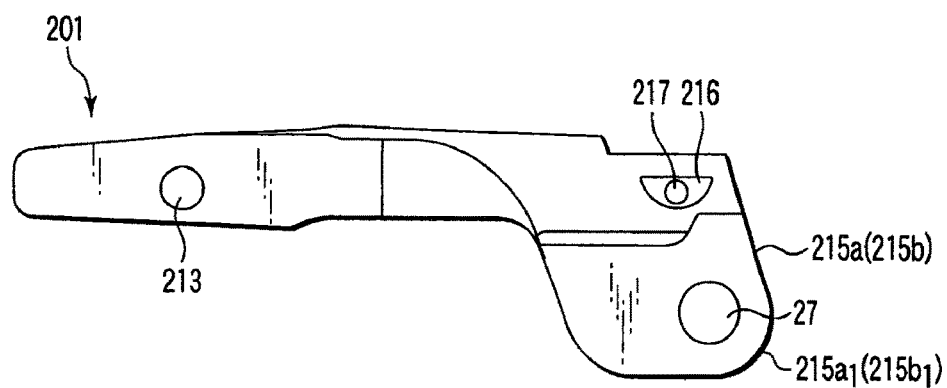
FIG. 14 is a side view showing a jaw body of the jaw of the ultrasonic therapeutic apparatus according to the first embodiment.
Figure 15:
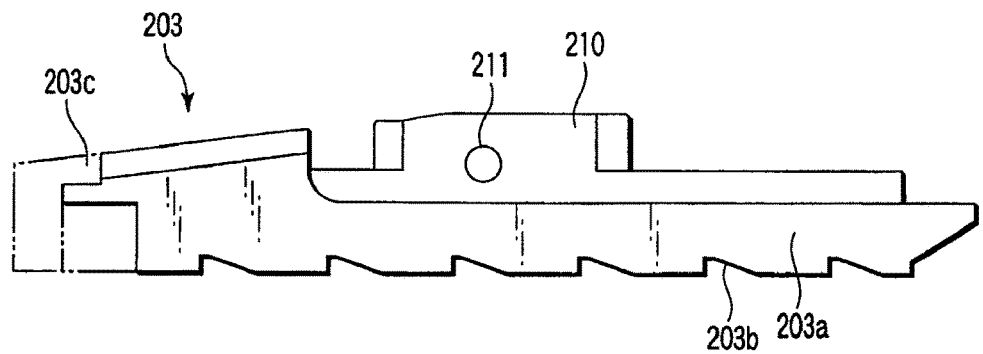
FIG. 15 is a side view showing an electrode member of the jaw of the ultrasonic therapeutic apparatus according to the first embodiment.

The jaw 17 includes a metallic jaw body 201 (see FIG. 14) which is an electrically conductive member, and a hold member 202 which is attached to the jaw body 201. The hold member 202 is composed of an electrode member 203 (see FIG. 15) for high-frequency therapeutic treatment, and an insulation member 204 (see FIG. 16) for ultrasonic therapeutic treatment. The electrode member 203 constitutes a second electrode section which is the other electrode of the bipolar electrodes.

As shown in FIGS. 17 and 18, a groove portion 205, which is formed in accordance with the curved shape of the probe distal end portion 3*a*, is formed on the lower surface of the electrode member 203. An engaging surface 206, which is to be engaged with the probe distal end portion 3*a*, is formed by the groove portion 205. A groove width W of the groove portion 205 is set in consideration of the diameter dimension of the probe distal end portion 3*a*. Specifically, the groove width W is set to be greater than the diameter dimension of the probe distal end portion 3*a* by a predetermined ratio, thereby preventing contact between the engaging surface 206 of the electrode member 203 and the probe distal end portion 3*a*.

Inclined surfaces 205*a*, which are configured to gradually increase the groove width toward a lower-side opening surface, as shown in FIG. 18, are formed on both side wall surfaces of the groove portion 205. In addition, as shown in FIG. 19, tooth portions 203*b* for preventing a slip are formed on both side walls 203*a* of the groove portion 205 on the lower-side opening surface side. The tooth portions 203*b* form a slip-preventing section for preventing a slip of a clamped object between the probe distal end portion 3*a* and the jaw 17 when the jaw 17 and probe distal end portion 3*a* are engaged. A wall thickness T of the electrode member 203 is properly determined in consideration of the rigidity and coagulation performance.

Further, in the electrode member 203, a notch portion 205*b* is formed at a bottom portion of the groove portion 205. The notch portion 205*b* is formed in accordance with the curved shape of the probe distal end portion 3*a*. A pad member 207, which is formed of an insulating material, for instance, a resin material such as polytetrafluoroethylene, is disposed in the notch portion 205*b*. As shown in FIG. 18, the pad member 207 is a probe contact member which is in contact with the probe distal end portion 3*a*. The probe distal end portion 3*a* comes in contact with the pad member 207, thus securing a clearance between the second electrode section of the electrode member 203 and the probe distal end portion 3*a*.

In addition, the jaw 17 has a block-shaped distal end chip 208 at a distal end portion of the engaging surface 206 for engagement with the probe distal end portion 3*a*. The distal end chip 208 is formed of an insulating material, for instance, a resin material such as polytetrafluoroethylene. When the jaw 17 and probe distal end portion 3*a* are engaged, a positional displacement relative to the probe distal end portion 3*a* is tolerated by the distal end chip 208.

Figure 16:
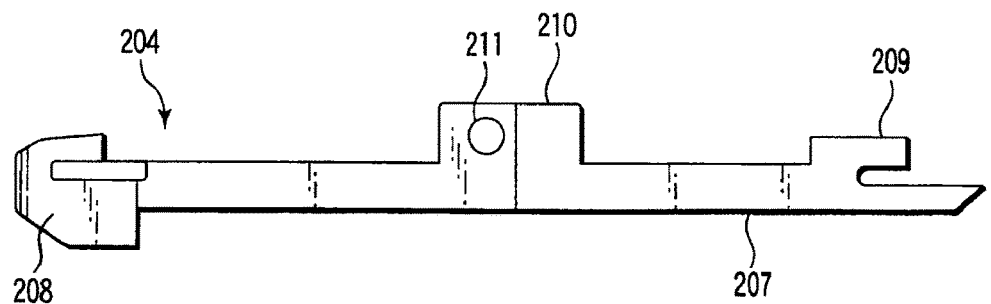
FIG. 16 is a side view showing an insulation member of the jaw of the ultrasonic therapeutic apparatus according to the first embodiment.

As shown in FIG. 16, in the insulation member 204, the distal end chip 208 is coupled to the distal end portion of the pad member 207. In the insulation member 204, the pad member 207 and the distal end chip 208 are provided as one body.

The electrode member 203 and insulation member 204 are integrally assembled to form the hold member 202. A hook-shaped engaging portion 209 is formed at a rear end portion of the insulation member 204. In addition, a distal end chip engaging portion 203*c*, which engages the distal end chip 208, is formed at the distal end portion of the electrode member 203. When the electrode member 203 and the insulation member 204 are assembled, the distal end chip 208 is engaged with the distal end chip engaging portion 203*c*, and also the engaging portion 209 at the rear end portion of the insulation member 204 is engaged with the rear end portion of the electrode member 203 in the state in which the pad member 207 is inserted in the notch portion 205*b* of the groove portion 205 of the electrode member 203.

A projection portion 210 for attachment is provided on that side of the hold member 202, which is opposed to the engaging surface 206 for engagement with the probe distal end portion 3*a*. A screw insertion hole 211 is formed in the projection portion 210.

A hold member engaging portion 212, which engages the projection portion 210 of the hold member 202, is provided on a distal end side of the jaw body 201. The hold member 202 is engaged with the hold member engaging portion 212. Further, a screw hole 213 is formed in side wall portions of the hold member engaging portion 212. As shown in FIG. 18, when the hold member engaging portion 212 of the jaw body 201 and the projection portion 210 of the hold member 202 are engaged, a fixing screw 214, which is engaged in the screw hole 213 of the jaw body 201, is inserted in the screw insertion hole 211 of the hold member 202. In this state, the fixing screw 214 is fastened in the screw hole 213, and thereby the hold member 202 is attached to the jaw body 201. The electrode member 203 of the hold member 202 and the jaw body 201 are electrically connected via the fixing screw 214.

A proximal end portion of the jaw body 201 has two-forked arm portions 215*a* and 215*b*. The respective arm portions 215*a* and 215*b* have extension portions 215*a*1 and 215*b*1, which extend obliquely downward from a position of a center line of the jaw body 201. The extension portions 215*a*1 and 215*b*1 are rotatably attached by the support pin 27 to the right and left projection portions 25 at the distal end portion of the sheath 18.

A coupling pin insertion hole 216 is formed in a proximal portion of each of the two arm portions 215*a* and 215*b*. A coupling pin 217 for coupling the jaw body 201 and the driving pipe 19 is inserted in the coupling pin insertion holes 216. The jaw body 201 and the driving pipe 19 are electrically connected via the coupling pin 217.

Thereby, the driving force of the driving pipe 19 is transmitted to the jaw 17 via the coupling pin 217 by the advancing/retreating in the axial direction of the driving pipe 19. Accordingly, the jaw 17 is rotated about the support pin 27. In this case, when the driving pipe 19 is pulled rearward, the jaw 17 is rotated about the support pin 27 and driven (to an open position) in a direction away from the probe distal end portion 3*a*. Conversely, when the driving pipe 19 is pushed forward, the jaw 17 is rotated about the support pin 27 and driven (to a closed position) in a direction toward the probe distal end portion 3*a*. A living body tissue is held between the jaw 17 and the probe distal end portion 3a of the probe unit 3 when the jaw 17 is rotated to the closed position.

The therapeutic section 1A of the handpiece 1 is constituted by the jaw 17 and the probe distal end portion 3a of the probe unit 3. The therapeutic section 1A is configured to selectively perform a plurality of therapeutic functions, for example, two therapeutic functions (a first therapeutic function and a second therapeutic function) in this embodiment. For instance, the first therapeutic function is set to be a function of simultaneously outputting an ultrasonic therapeutic output and a high-frequency therapeutic output. The second therapeutic function is set to be a function of outputting only the high-frequency therapeutic output.

The first therapeutic function and second therapeutic function of the therapeutic section 1A are not limited to the above-described configuration. For example, the first therapeutic function may be set to be a function of outputting an ultrasonic therapeutic output in a maximum output state, and the second therapeutic function may be set to be a function of outputting the ultrasonic therapeutic output in a preset arbitrary output state which is lower than the maximum output state.

As shown in FIGS. 17 and 19, the jaw 17 has, at a distal end portion of the groove portion 205, a distal-end-side groove width varying section 205t1 which has such a tapering shape that the groove width of the groove portion 205 gradually increases toward the distal end. In addition, the jaw 17 has, at a proximal end portion of the groove portion 205, a proximal-end-side groove width varying section 205t2 which has such a tapering shape that the groove width of the groove portion 205 gradually increases toward the proximal end. In the distal-end-side groove width varying section 205t1 and proximal-end-side groove width varying section 205t2, a positional displacement in assembly between the probe distal end portion 3a and the electrode member 203 of the jaw 17 can be tolerated in a case where the assembly position of the electrode member 203 of the jaw 17 is slightly displaced, relative to the probe distal end portion 3a, in the axial direction of the sheath unit 5 when the probe unit 3 and the sheath unit 5 are assembled.

Figure 21:
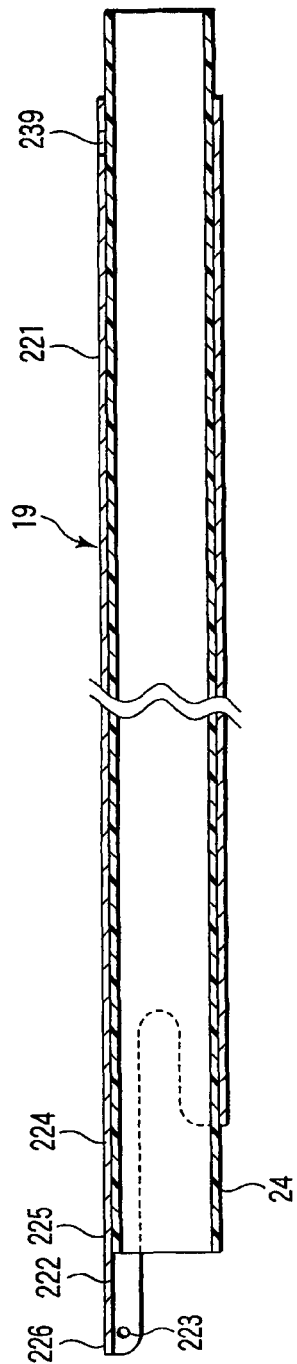
FIG. 21 is a longitudinal cross-sectional view showing a driving pipe of the ultrasonic therapeutic apparatus according to the first embodiment.

FIG. 21 shows the driving pipe 19. The driving pipe 19 includes a tubular body section 221 and an operating section 222. The body section 221 is inserted in the sheath 18 so as to be slidable in the axial direction of the sheath 18. The operating section 222 is disposed on the distal end side of the body section 221, and includes a connection section 223 which is connected to the jaw 17.

Figure 22:
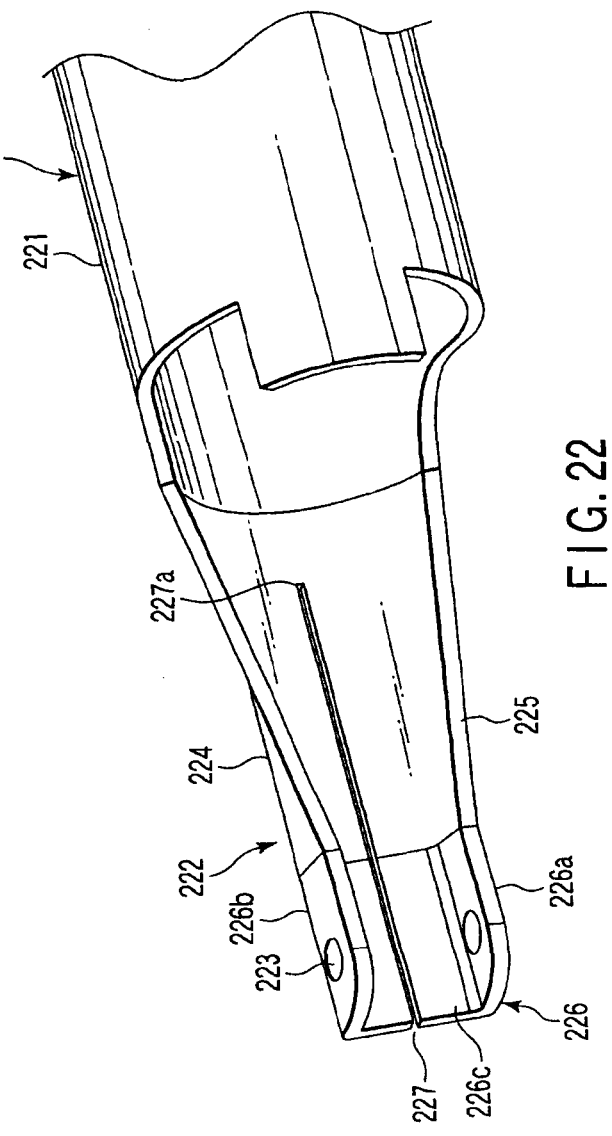
FIG. 22 is a perspective view showing a distal end portion of the driving pipe of the ultrasonic therapeutic apparatus according to the first embodiment.
Figure 23:
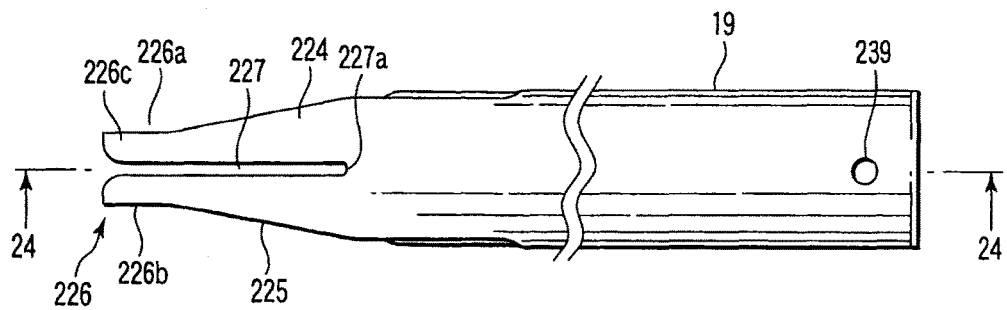
FIG. 23 is a plan view showing the driving pipe of the ultrasonic therapeutic apparatus according to the first embodiment.
Figure 24:
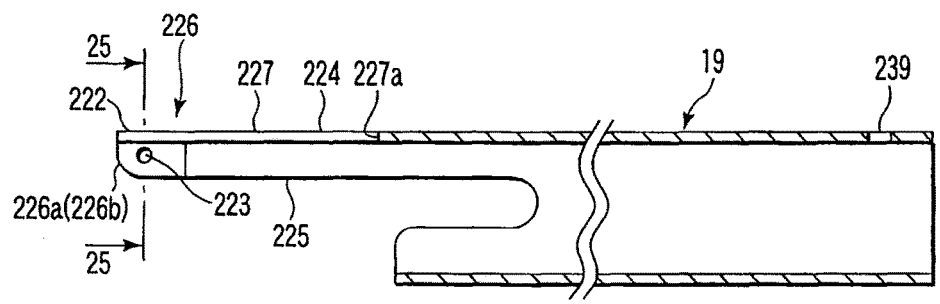
FIG. 24 is a cross-sectional view taken along line 24-24 in FIG. 23.
Figure 25:
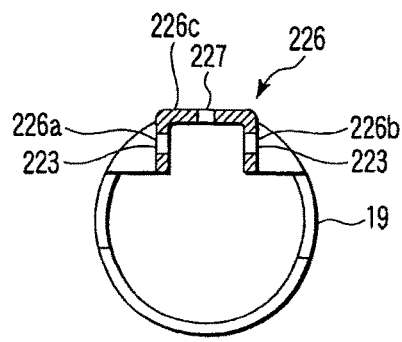
FIG. 25 is a front view showing the driving pipe of the ultrasonic therapeutic apparatus according to the first embodiment.

As shown in FIG. 22, the peripheral wall of a tubular distal end portion of the body section 221 includes a crescent-shaped arcuate cross-sectional portion 224, which is formed by leaving a substantially crescent-shaped arcuate cross-sectional portion over a predetermined length in the axial direction, and cutting out the other portion. As shown in FIG. 23, the arcuate cross-sectional portion 224 includes a taper portion 225 with a tapered distal end portion, which is gradually tapered toward the distal end side. As shown in FIG. 22 and FIG. 25, a U-shaped portion 226 having a U-shaped cross section is formed at a distal end of the taper portion 225. The operating section 222 is constituted by the U-shaped portion 226.

As shown in FIG. 22, the U-shaped portion 226 has two side surfaces 226a and 226b, which are opposed to each other, and a connecting surface 226c which connects the two side surfaces 226a and 226b. The connection section 223 is formed in each of the two side surfaces 226a and 226b of the U-shaped portion 226.

The operating section 222 has a slit 227 extending in the axial direction of the sheath 18 in a distal end portion of the connecting surface 226c. As shown in FIG. 23, the slit 227 has a terminal end portion 227a which is located at a position corresponding to a proximal end portion of the taper portion 225.

As shown in FIG. 8A, the insulation tube 24 includes a projection portion 228 which projects forward of the body section 221 of the driving pipe 19. The projection portion 228 extends up to a rear end position of the U-shaped portion 226.

Further, a proximal end portion of the insulation tube 24 extends to a proximal end side of the sheath body 16. The driving pipe 19 and probe unit 3 are electrically insulated by the insulation tube 24.

FIG. 9 shows a proximal end portion of the sheath body 16. The proximal end portion of the sheath 18 includes a flare portion 229 which has a greater inside diameter than the other portion. A proximal end portion of the driving pipe 19 extends more rearward than the flare portion 229 of the sheath 18.

Seal means 230 for effecting sealing between the sheath 18 and the driving pipe 19 is provided between the flare portion 229 and the driving pipe 19. The seal means 230 includes two backup rings 231 and 232 and one O ring 233. The two backup rings 231 and 232 are disposed between the flare portion 229 and the driving pipe 19 in the state in which the two backup rings 231 and 232 are paired in a back-and-forth direction along the axis of the sheath 18. The O ring 233 is provided between the backup rings 231 and 232 so as to be movable in the axial direction of the sheath 18.

In addition, the proximal end portion of the sheath body 16 is provided with an attachment/detachment mechanism section 31 for attachment/detachment to/from the handle unit 4. The attachment/detachment mechanism section 31 includes a cylindrical large-diameter handle member 32 which is formed of a resin material, a guide cylindrical body (first tubular member) 33 which is formed of a metallic cylindrical body, and a cylindrical connection tube body (second tubular member) 34 which is formed of a resin material.

The guide cylindrical body 33 includes a tubular body 33a which is fitted on the flare portion 229 of the proximal end portion of the sheath 18 and extends rearward. A distal end portion of the tubular body 33a is provided with a large-diameter 33b which has a greater outside diameter than the other portion thereof. The handle member 32 is fitted on the large-diameter portion 33b. A connection flange portion 33c, which projects outward, is formed on an outer peripheral surface of a rear end portion of the guide cylindrical body 33.

Figure 27:
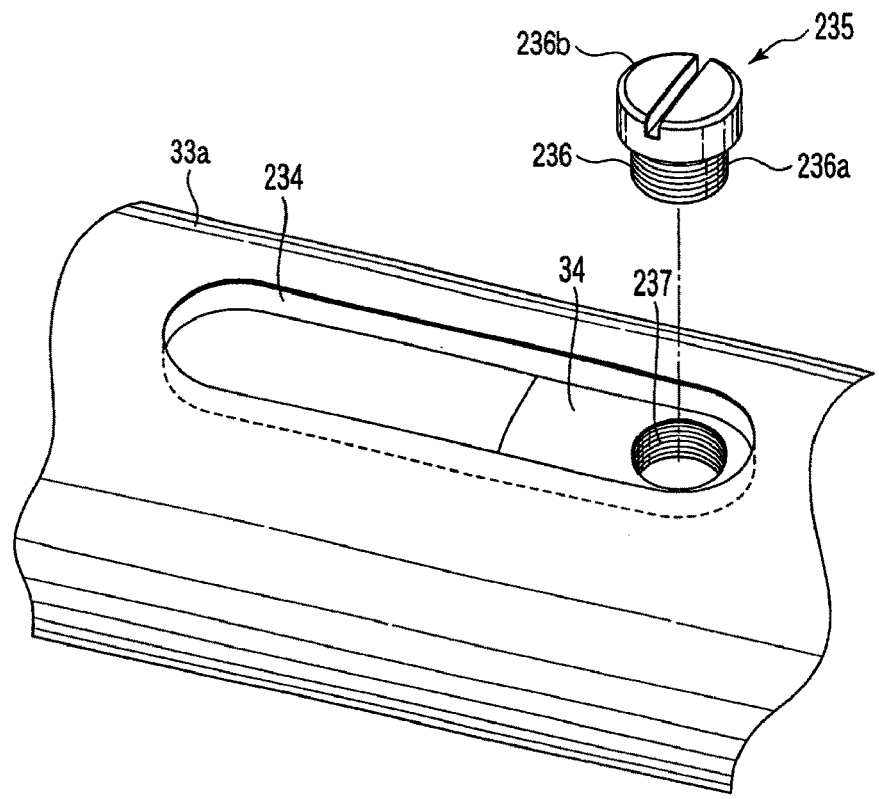
FIG. 27 is a perspective view showing the state before the threaded pin is engaged in the assembly section at the proximal end portion of the sheath unit of the ultrasonic therapeutic apparatus according to the first embodiment.

As shown in FIG. 27, an outer peripheral wall portion of the tubular 33a has an elongated slit 234 extending in the axial direction of the sheath 18. In addition, on the rear end portion side of the guide cylindrical body 33, a distal end portion of the connection tube body 34 is inserted so as to be slidable in the axial direction of the sheath 18. A proximal end portion of the driving pipe 19 is fitted and inserted inside the inner peripheral surface of the distal end portion of the connection tube body 34.

Figure 26:
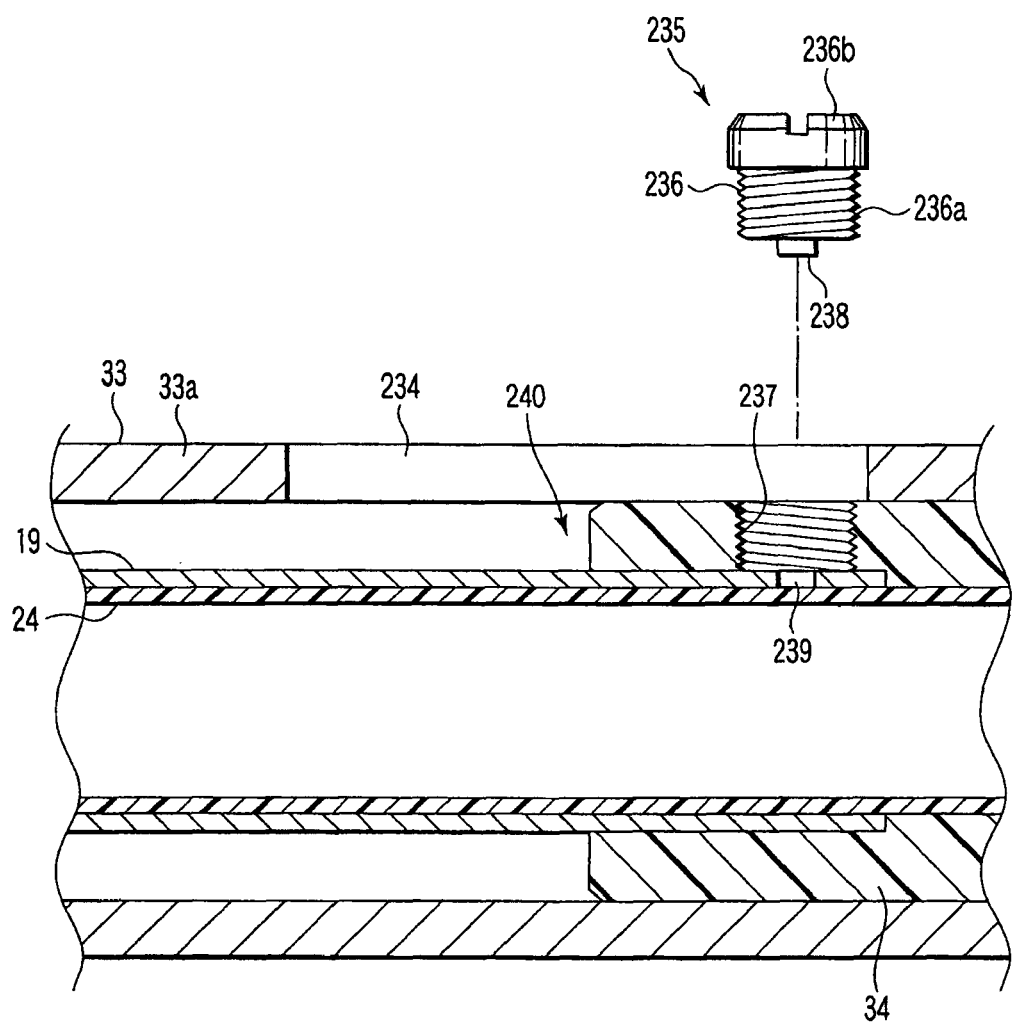
FIG. 26 is a longitudinal cross-sectional view showing a state before a threaded pin is engaged in an assembly section at the proximal end portion of the sheath unit of the ultrasonic therapeutic apparatus according to the first embodiment.
Figure 28:
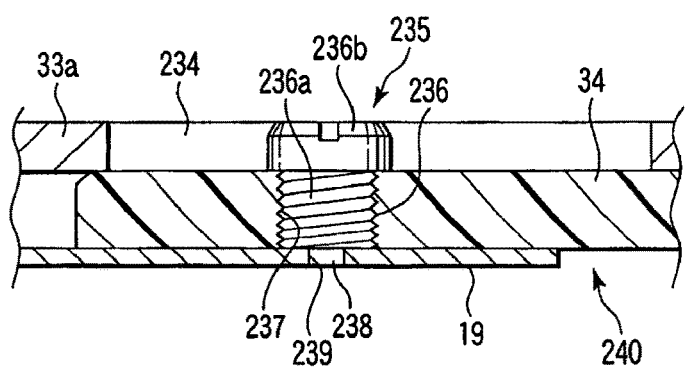
FIG. 28 is a longitudinal cross-sectional view showing the state in which the threaded pin is engaged in the assembly section at the proximal end portion of the sheath unit of the ultrasonic therapeutic apparatus according to the first embodiment.

As shown in FIG. 28, a threaded pin (projection body) 235 is fixed to a proximal end portion of the driving pipe 19. As shown in FIG. 26, the threaded pin 235 includes a male screw member 236. A threaded hole portion 237, which is engaged with a male screw portion 236a of the threaded pin 235, is formed in the connection tube body 34.

A large-diameter portion 236b, which has a greater diameter than the male screw portion 236a, is formed on a head portion of the screw member 236. The large-diameter portion 236b of the threaded pin 235 is an engaging portion which is engaged in the slit 234 of the guide cylindrical body 33.

A small-diameter portion 238, which has a smaller diameter than the male screw portion 236a, is provided on the threaded pin 235 so as to project on a side opposite to the head portion of the screw member 236. The small-diameter portion 238 is inserted and fitted in a fixing hole 239 which is formed in a proximal end portion of the driving pipe 19. Thereby, the male screw portion 236a of the threaded pin 235 is engaged in and passed through the screw hole portion 237 of the connection tube body 34, and a coupling body 240, in which the driving pipe 19 and the connection tubular body 34 are coupled, is formed. Further, the large-diameter portion 236b of the threaded pin 235 is engaged with the slit 234 of the guide cylindrical body 33, and thereby the coupling body 240 is coupled to the guide cylindrical body 33 so as to be movable as one body along the slit 234 in the axial direction of the sheath 18.

A fixing section 35 of the guide cylindrical body 33 is formed by an engaging section between the handle member 32 and the large-diameter portion 33b of the guide cylindrical body 33. Further, in the handle member 32, an attachment/detachment section 36 for attachment/detachment to/from the handle unit 4 is disposed on the rear side of the fixing section 35.

Figure 29:
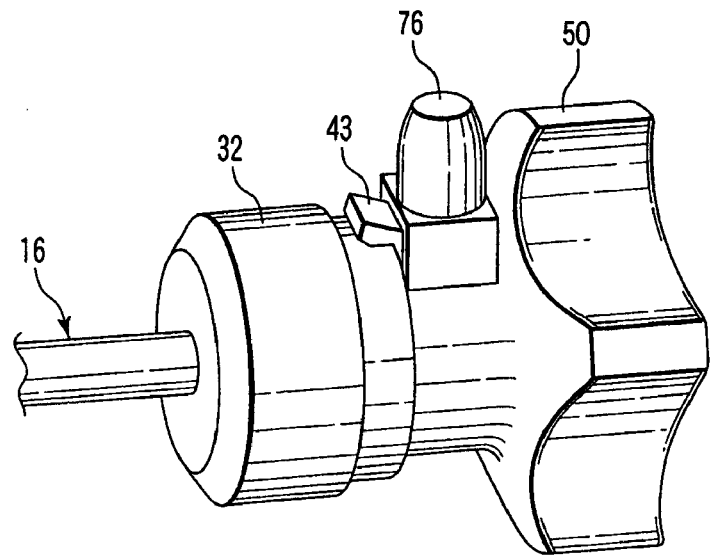
FIG. 29 is a perspective view showing a state prior to rotational engagement at the time when the handle unit and sheath unit of the ultrasonic therapeutic apparatus according to the first embodiment are coupled.
Figure 30:
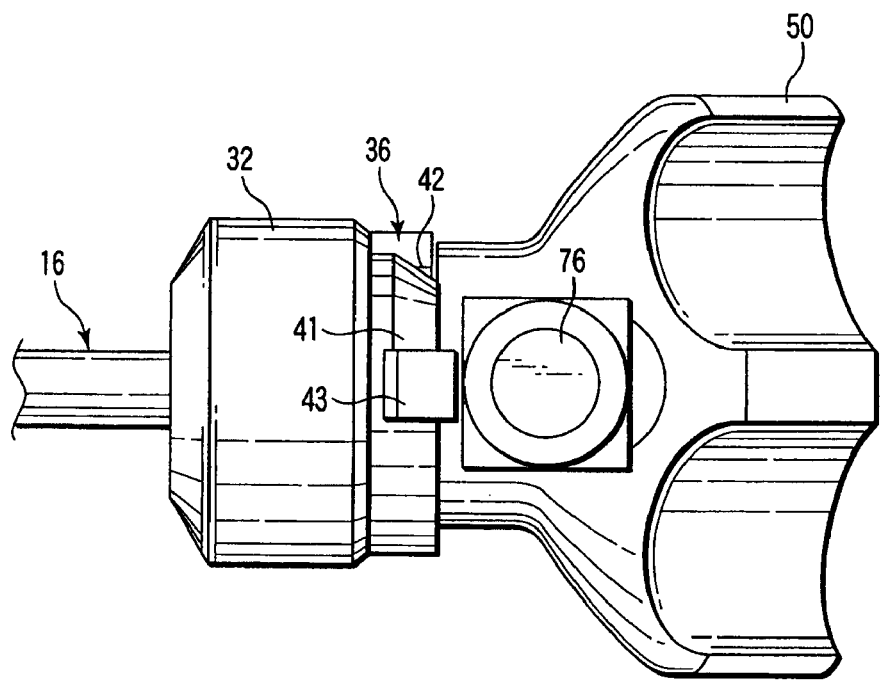
FIG. 30 is a plan view showing the state prior to rotational engagement at the time when the handle unit and sheath unit of the ultrasonic therapeutic apparatus according to the first embodiment are coupled.

FIG. 29 to FIG. 32 show the structure of the attachment/detachment part between the handle member 32 and the handle unit 4. As shown in FIGS. 30 to 32, the attachment/detachment section 36 of the handle member 32 has a guide groove 41 with an inclined surface, and an engaging recess portion 42. The guide groove 41 is provided to extend in a circumferential direction on the outer peripheral surface of the proximal end portion of the handle member 32. In addition, the guide groove 41 has a tapered inclined surface with an outside diameter decreasing toward the rear end portion side of the handle member 32.

Figure 33:
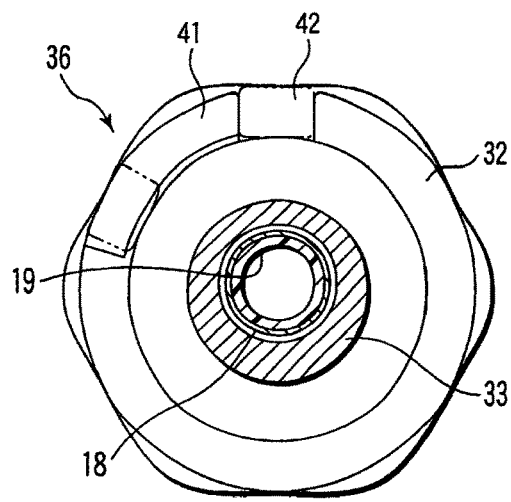
FIG. 33 is an explanatory view for explaining a positional relationship between a guide groove and an engaging recess portion at the coupling section between the handle unit and sheath unit of the ultrasonic therapeutic apparatus according to the first embodiment.

As shown in FIG. 33, the engaging recess portion 42 is formed at one end portion of the guide groove 41. The engaging recess portion 42 is formed of a recess portion having a smaller diameter than the inclined surface of the guide groove 41. The engaging recess portion 42 is configured such that the engaging lever 43 (to be described later) on the handle unit 4 side is disengageably engaged in the engaging recess portion 42. FIGS. 31 and 32 show the state in which the engaging lever 43 is engaged in the engaging recess portion 42, and FIGS. 29 and 30 show the disengaged state in which the engaging lever 43 is pulled out of the engaging recess portion 42.

Figure 34:
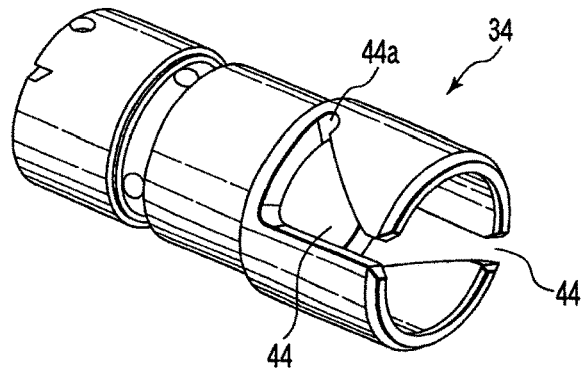
FIG. 34 is a perspective view showing a connection tube body of the sheath unit of the ultrasonic therapeutic apparatus according to the first embodiment.
Figure 35:
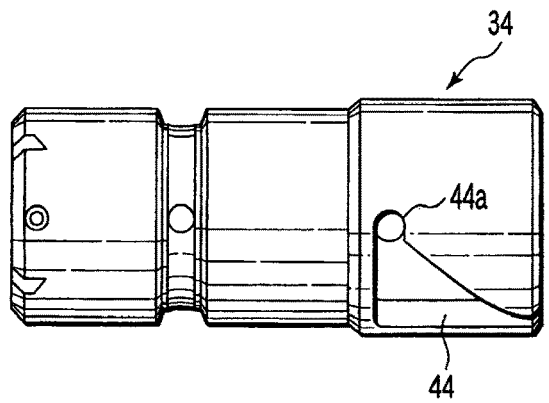
FIG. 35 is a perspective view showing the connection tube body of the sheath unit of the ultrasonic therapeutic apparatus according to the first embodiment.

As shown in FIGS. 34 and 35, a proximal end portion of the connection tube body 34 has two guide grooves 44 which are used at a time of attachment/detachment to/from the handle unit 4 side. The guide grooves 44 are configured such that two engaging pins 45 (to be described later) on the handle unit 4 side are disengageably engaged in the guide grooves 44, respectively. An engaging groove 44a, which restricts movement of the engaging pin 45 in the axial direction of the sheath body 16, is formed at a terminal end portion of the guide groove 44.

As shown in FIG. 9B, the connection flange portion 33c of the guide cylindrical body 33 has a non-circular engaging portion 46. The engaging portion 46 has three cut-out flat-surface portions 46a at a plurality of locations on the circular outer peripheral surface of the connection flange portion 33c, for example, at three locations in this embodiment. Corner portions 46b, each having a greater diameter than the flat-surface portion 46a, are formed at connection parts between the three flat-surface portions 46. Thereby, the engaging portion 46 with a substantially triangular cross section is formed on the connection flange portion 33c. It is not necessary that the non-circular engaging portion 46 have a substantially triangular shape. The non-circular engaging portion 46 may have any other non-circular shape, for instance, a polygon such as a rectangle or a pentagon.

As shown in FIG. 3, the handle unit 4 mainly includes a stationary handle 47, a hold cylinder 48, a movable handle 49 and a rotational operation knob 50. The hold cylinder 48 is provided on the upper part of the stationary handle 47. A switch hold section 51 is provided between the stationary handle 47 and the hold cylinder 48. As shown in FIG. 36, the switch hold section 51 includes a switch attachment section 52 which is fixed to a lower end portion of the hold cylinder 48, and a cover member 53 which is fixed to an upper end portion of the stationary handle 47.

Figure 37:
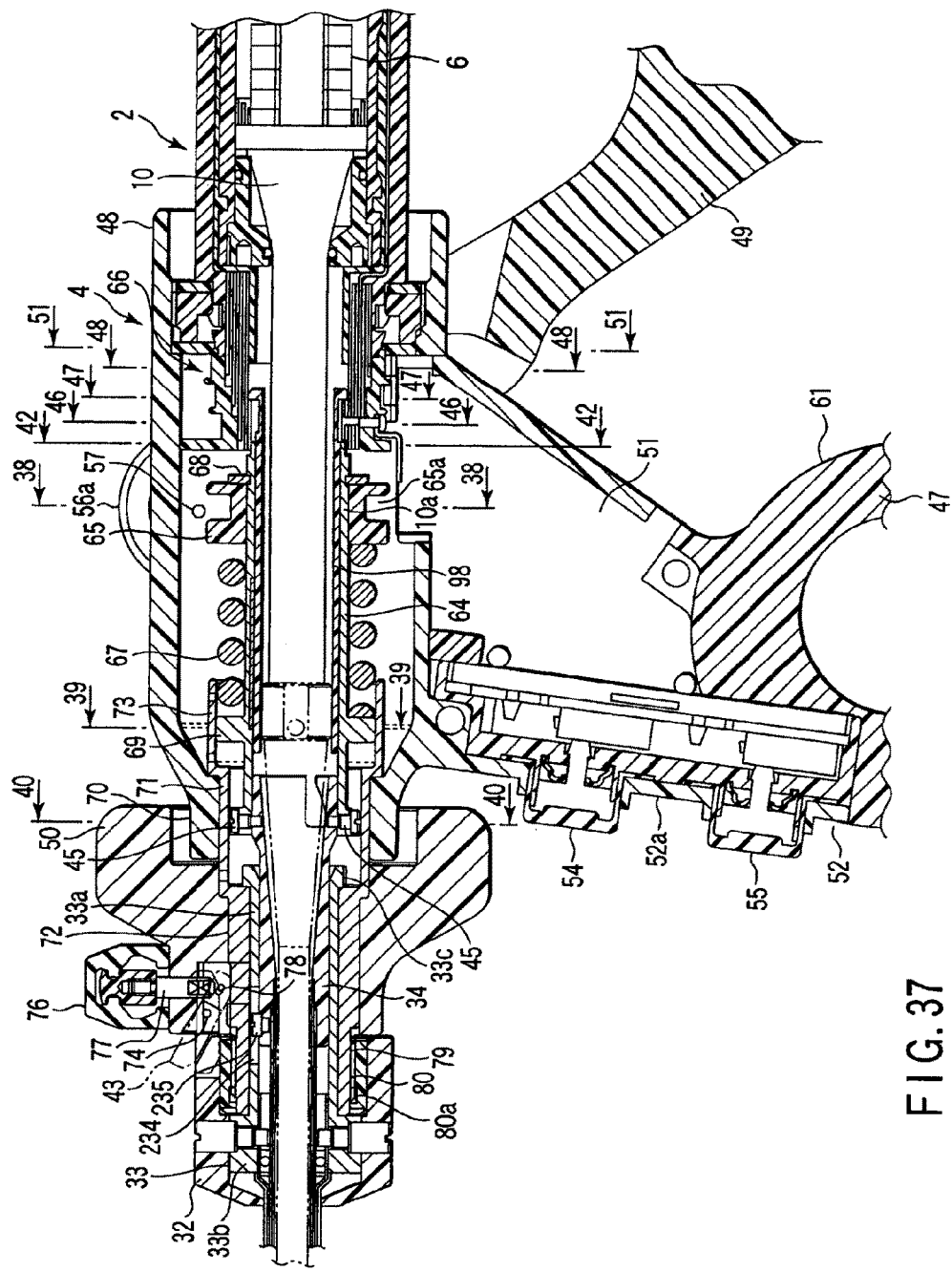
FIG. 37 is a longitudinal cross-sectional view showing a state after engagement between the handle unit and sheath unit of the ultrasonic therapeutic apparatus according to the first embodiment.

As shown in FIG. 37, the switch attachment section 52 has a switch attachment surface 52a on a front side thereof, to which a plurality of hand switches, for example, two hand switches (first switch 54 and second switch 55) in the present embodiment, are attached. The first switch 54 and second switch 55 are switches for selecting therapeutic functions of the therapeutic section 1A of the handpiece 1.

In the switch attachment section 52, the first switch 54 and second switch 55 are arranged in the up-and-down direction. The first switch 54 is disposed on an upper side of the switch attachment surface 52a, and is set to be a switch which selects a first therapeutic function that is frequently used among the plural therapeutic functions. The second switch 55 is disposed on a lower side of the switch attachment surface 52a, and is set to be a switch which selects another second therapeutic function of the plural therapeutic functions.

As shown in FIG. 2, the movable handle 49 has a substantially U-shaped arm section 56 at an upper part thereof. The U-shaped arm section 56 includes two arms 56a and 56b. The movable handle 49 is assembled to the hold cylinder 48 in the state in which the hold cylinder 48 is inserted between the two arms 56a and 56b.

Each of the arms 56a and 56b has a support pin 57 and an operation pin 58. As shown in FIG. 36, a pin receiving hole portion 59 and a window portion 60 are formed in each of both side portions of the hold cylinder 48. The support pin 57 of each arm 56a, 56b is inserted in the pin receiving hole portion 59 of the hold cylinder 48. Thereby, an upper end portion of the movable handle 49 is rotatably supported on the hold cylinder 48 via the support pins 57.

Ring-shaped finger hook portions 61 and 62 are provided on lower end portions of the stationary handle 47 and movable handle 49, respectively. By hooking the fingers on the finger hook portions 61 and 62 and holding them, the movable handle 49 rotates via the support pins 57 and the movable handle 49 is opened/closed relative to the stationary handle 47.

The operation pins 58 of the movable handle 49 extend into the hold cylinder 48 through the window portions 60 of the hold cylinder 48. An operation force transmission mechanism 63, which transmits an operation force of the movable handle 49 to the driving pipe 19 of the jaw 17, is provided inside the hold cylinder 48.

As shown in FIG. 37, the operation force transmission mechanism 63 mainly comprises a metallic cylindrical spring receiving member 64 and a resin-made slider member 65. The spring receiving member 64 is disposed coaxially with the center axis of the hold cylinder 48, and extends in the same direction as the direction of insertion of the probe unit 3.

A coil spring 67, the slider member 65, a stopper 68 and a spring receiver 69 are provided on an outer peripheral surface of the spring receiving member 64. A front end portion of the coil spring 67 is fixed to the spring receiver 69. The stopper 68 restricts the position of movement of a rear end side of the slider member 65. The coil spring 67 is disposed between the spring receiver 69 and the slider member 65 with a fixed amount of mounting force.

Figure 38:
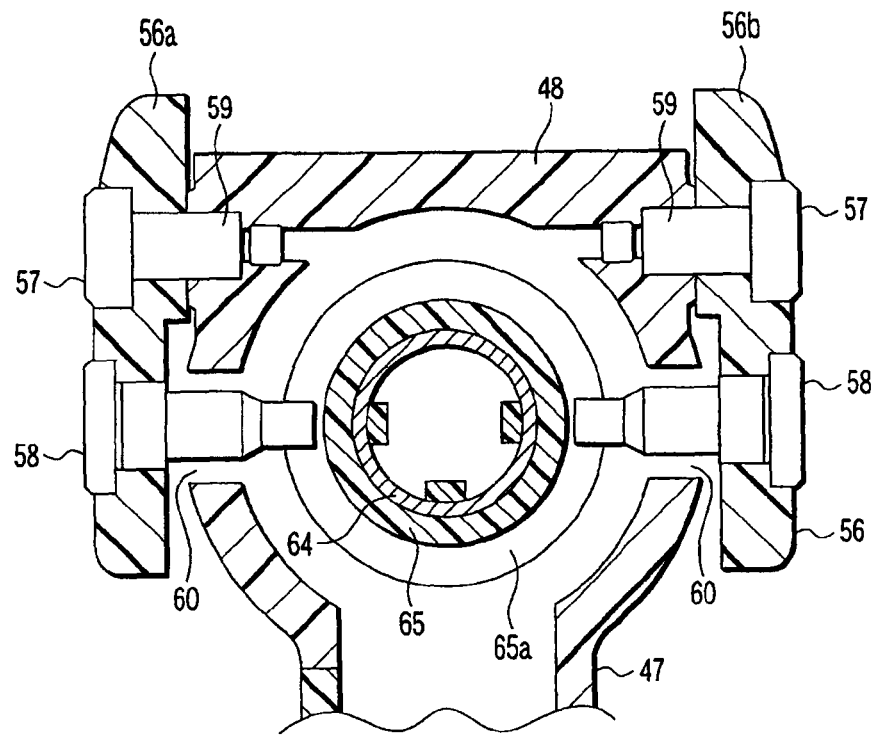
FIG. 38 is a cross-sectional view taken along line 38-38 in FIG. 37.
Figure 40:
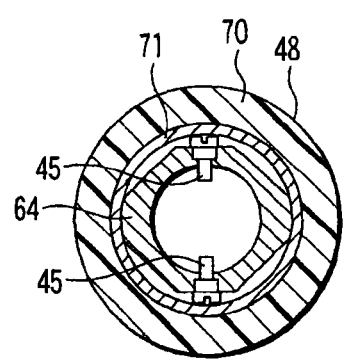
FIG. 40 is a cross-sectional view taken along line 40-40 in FIG. 37.

An annular engaging groove 65a is formed in a circumferential direction in an outer peripheral surface of the slider member 65. As shown in FIG. 38, the operation pins 58 of the movable handle 49 are inserted and engaged in the engaging groove 65a. If the movable handle 49 is held and the movable handle 49 is closed relative to the stationary handle 47, the operation pins 58 rotate about the support pins 57 in accordance with the rotational operation of the movable handle 49 at this time. The slider member 65, which is in interlock with the rotation of the support pins 57, moves forward in the axial direction. At this time, the spring receiving member 64, which is coupled to the slider member 65 via the coil spring 67, moves forward/backward together with the slider member 65. As shown in FIG. 40, a pair of engaging pins 45, which are used when the sheath unit 5 and the handle unit 4 are attached/detached, are fixed to a distal end portion of the spring receiving member 64. Thereby, the operation force of the movable handle 49 is transmitted to the connection tube body 34 of the sheath unit 5 via the pair of engaging pins 45, and the driving pipe 19 of the jaw 17 moves forward. Thereby, the jaw body 201 of the jaw 17 rotates via the support pin 27.

Further, when a living body tissue is clamped between the hold member 202 of the jaw 17 and the probe distal end portion 3a of the probe unit 3 by this operation, the hold member 202 rotates over a certain angle about the pin 214 in accordance with the bending of the probe distal end portion 3a so that force uniformly acts over the entire length of the hold member 202. In this state, ultrasonic is output and a living body tissue, such as a blood vessel, can be coagulated or cut.

An annular bearing portion 70 is formed at a front end portion of the hold cylinder 48. The bearing portion 70 is metallic, and a cylindrical rotation transmission member 71 is coupled to the bearing portion 70 rotatably about the axis. The rotation transmission member 71 includes a projecting portion 72 which projects forward of the bearing portion 70, and a large-diameter portion 73 which extends to the inner side of the hold cylinder 48 from the bearing portion 70.

The rotational operation knob 50 is fitted and fixed on the projecting portion 72. The engaging lever 43 is provided at the front end portion of the rotational operation knob 50. An intermediate portion of the engaging lever 43 is rotatably coupled to the projecting portion 72 via a pin 74. A proximal end portion of the engaging lever 43 extends to the inside of a lever receiving recess portion 75 which is formed in a front surface of the rotational operation knob 50.

An operation button 76 for operating the engaging lever 43 in such a direction as to disengage the engaging lever 43 is provided on an outer peripheral surface of the front end portion of the rotational operation knob 50. An operation pin 77, which is disposed downward, is provided so as to project from the operation button 76. The operation pin 77 extends to the inside of the lever receiving recess portion 75 through a wall hole of the rotational operation knob 50. A proximal end portion of the engaging lever 43 is rotatably coupled to a lower end portion of the operation pin 77 via a pin 78.

A removal prevention ring 80 for the rotational operation knob 50 is provided on a distal end portion of the projecting portion 72. A male threaded portion 79 is formed on the distal end portion of the projecting portion 72. A female threaded portion 80a, which is to be meshed with the male threaded portion 79, is formed on an inner peripheral surface of the removal prevention ring 80. The female threaded portion 80a of the removal prevention ring 80 is meshed and engaged with the male threaded portion 79 of the projecting portion 72, and thereby the rotational operation knob 50 is fixed to the rotation transmission member 71.

Figure 39:
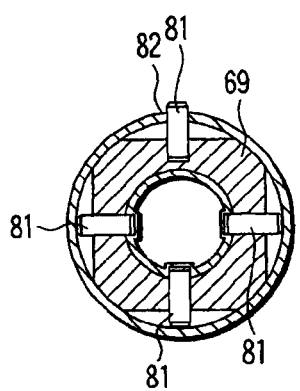
FIG. 39 is a cross-sectional view taken along line 39-39 in FIG. 37.

As shown in FIG. 39, the spring receiver 69 of the spring receiving member 64 is provided with four metallic positioning pins 81 which project radially outward. An elongated engaging hole portion 82, in which one pin 81 of the spring receiving member 64 is inserted, is formed in the large-diameter portion 73 of the rotation transmission member 71. The engaging hole portion 82 extends in the same direction as the direction of insertion of the probe unit 3. Thereby, when the movable handle 49 is operated, the pin 81 is moved along the engaging hole portion 82 and thus the advancing/retreating movement of the spring receiving member 64 is prevented from being transmitted to the rotation transmission member 71.

On the other hand, when the rotational operation knob 50 is rotated, the rotational movement of the rotation transmission member 71, which rotates together with the rotational operation knob 50, is transmitted to the spring receiving member 64 via the pin 81. Thereby, when the rotational operation knob 50 is rotated, the assembly unit of the rotation transmission member 71, pin 81, spring receiving member 64, slider member 65 and coil spring 67 within the hold cylinder 48 is rotated together with the rotational operation knob as one body about the axis thereof.

Engaging means 94, which is disengageably engaged with the connection flange portion 33c of the sheath unit 5, is provided on the inner peripheral surface of the rotation transmission member 71. FIGS. 41A and 41B show the engaging means 94. The engaging means 94 includes an insertion hole portion 94a in which the connection flange portion 33c is inserted when the sheath unit 5 and handle unit 4 are coupled, and an electrically conductive rubber ring (urging means) 94b which is disposed within the insertion hole portion 94a.

The shape of the inner peripheral surface of the electrically conductive rubber ring 94b is substantially the same as the shape of the engaging portion 46 of the connection flange portion 33c. Specifically, the inner peripheral surface of the electrically conductive rubber ring 94b has three cut-out flat-surface portions 94b 1 at a plurality of locations on the circular outer peripheral surface, for example, at three locations in this embodiment, and three corner portions 94b2 which are located at connection parts between the three flat-surface portions 94b1 and have greater diameters than the flat-surface portions 94b. Thereby, the electrically conductive rubber ring 94b has a substantially triangular cross-sectional shape. Thus, as shown in FIG. 41A, the electrically conductive rubber ring 94b is held in a natural, non-compressed position in the positional state in which the inner peripheral surface shape of the electrically conductive rubber ring 94b corresponds to the engaging portion 46 of the connection flange portion 33c, that is, in the state in which the three corner portions 46b of the connection flange portion 33c correspond in position to the three corner portions 94b2 of the electrically conductive rubber ring 94b.

On the other hand, by rotating the handle unit 4 and the sheath unit 5 relative to each other about the center axis of the sheath unit 5, the position of the electrically conductive rubber ring 94*b* is switched to a pressure contact position, as shown in FIG. 41B, where the electrically conductive rubber ring 94*b* is pressed on the three corner portions 46*b* of the connection flange portion 33*c*. At this time, the three corner portions 46*b* of the connection flange portion 33*c* are put in contact with, and pressed by, the three flat-surface portions 94*b* 1 of the electrically conductive rubber ring 94*b*.

In the present embodiment, at the time of coupling the sheath unit 5 and handle unit 4, when the connection flange portion 33*c* of the sheath unit 5 is inserted straight into the electrically conductive rubber ring 94*b* (see FIG. 29 and FIG. 30), the electrically rubber ring 94*b* is held in the natural, non-compressed position, as shown in FIG. 41A. At this time, the engaging lever 43 on the handle unit 4 side is held in the state in which the engaging lever 43 rests on the inclined surface of the guide groove 41 of the handle member 32 of the sheath unit 5. Subsequently, the handle member 32 of the sheath unit 5 is rotated about the axis, relative to the handle unit 4. Thereby, as shown in FIG. 31 and FIG. 32, the engaging lever 43 on the handle unit 4 side is inserted and engaged in the engaging recess portion 42 at one end portion of the guide groove 41. At this time, as shown in FIG. 41B, the electrically conductive rubber ring 94*b* is switched to the pressure contact position where the electrically conductive rubber ring 94*b* is put in pressure contact with the three corner portions 46*b* of the connection flange portion 33*c*. Thereby, a sheath-unit-side electric path 40 (formed between the guide cylindrical body 33, fixing screw 39, coupling pipe 38, sheath 18, distal end cover 25, support pin 27 and jaw body) and a handle-unit-side electric path 95 (formed between an electrical contact member 96, spring receiving member 64, positioning pin 81 and rotation transmission member 71) are electrically connected via the electrically conductive rubber ring 94*b*. In this case, a second high-frequency electric path 97, which transmits a high-frequency current, is formed in the coupled body of the sheath unit 5 and handle unit 4.

As shown in FIG. 42, the handle unit 4 includes a tubular member 98 which is formed of an insulating material on the inner peripheral surface of the spring receiving member 64. The tubular member 98 is fixed on the inner peripheral surface of the spring receiving member 64. Thereby, when the probe unit 3 and the handle unit 4 are connected, the first high-frequency electric path 13 and the second high-frequency electric path 97 are insulated by the tubular member 98.

An inner peripheral surface of the tubular member 98 has three engaging projection portions 99 which correspond to the three engaging recess portions 15 (see FIG. 6) of the flange portion 14 of the probe unit 3. When the probe unit 3 and handle unit 4 are connected, the three engaging projection portions 99 of the tubular member 98 are disengageably engaged with the three engaging recess portions 15 of the flange portion 14 of the probe unit 3. Thereby, the rotational-directional position between the probe unit 3 and the tubular member 98 of the handle unit 4 is restricted. Hence, when the rotational operation knob 50 is rotated, the coupled body of the probe unit 3 and transducer unit 2 is rotated as one body together with the assembly unit within the hold cylinder 48.

The engaging section between the flange portion 14 of the probe unit 3 and the tubular member 98 is not limited to the above-described structure. For example, the tubular member 98 may be formed to have a D-shaped cross section, and the flange portion 14 of the probe unit 3 may be formed to have a corresponding D-shaped cross section.

Figure 43:
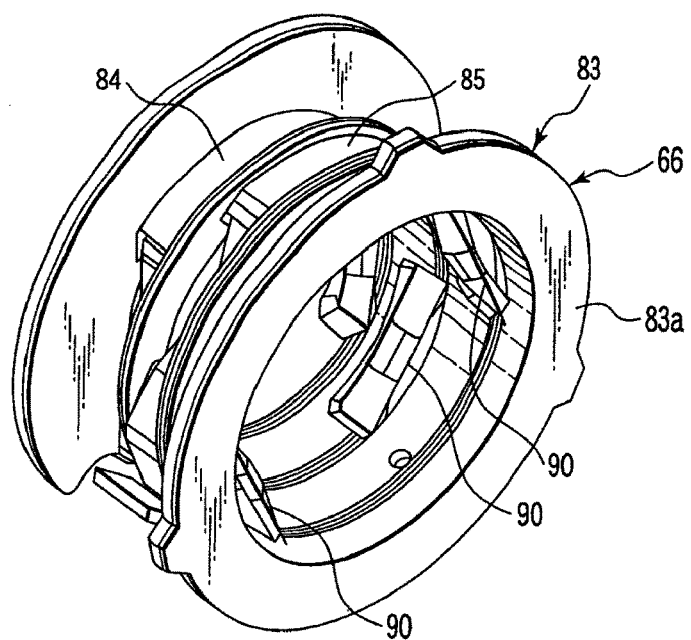
FIG. 43 is a perspective view showing an electrode hold member of the ultrasonic therapeutic apparatus according to the first embodiment.
Figure 44:
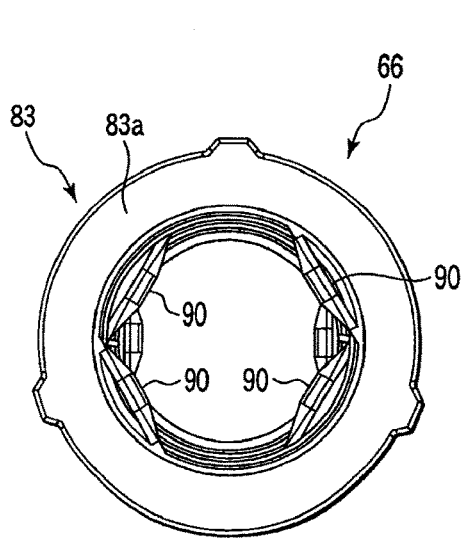
FIG. 44 is a front view showing the electrode hold member of the ultrasonic therapeutic apparatus according to the first embodiment.
Figure 45:
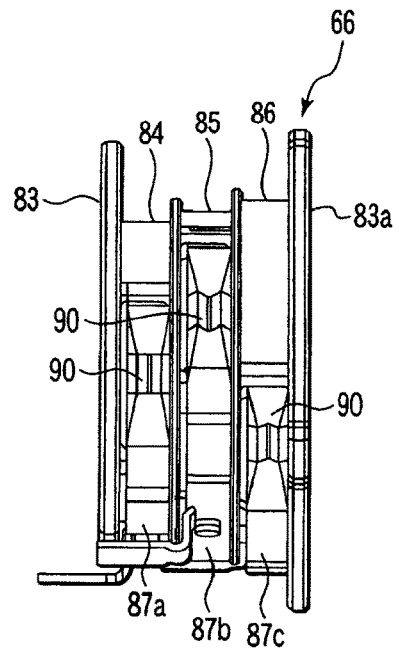
FIG. 45 is a side view showing the electrode hold member of the ultrasonic therapeutic apparatus according to the first embodiment.

FIGS. 43 to 45 show a cylindrical contact-point unit 66 which is assembled to the hold cylinder 48. The contact-point unit 66 includes a cylindrical electrode hold member 83 which is formed of a resin. As shown in FIG. 45, the electrode hold member 83 includes three (first to third) electrode receiving sections 84, 85 and 86 with different outside diameters. The first electrode receiving section 84 on the distal end side has a smallest diameter, and the third electrode receiving section 86 on the rear end side has a greatest diameter.

Figure 48:
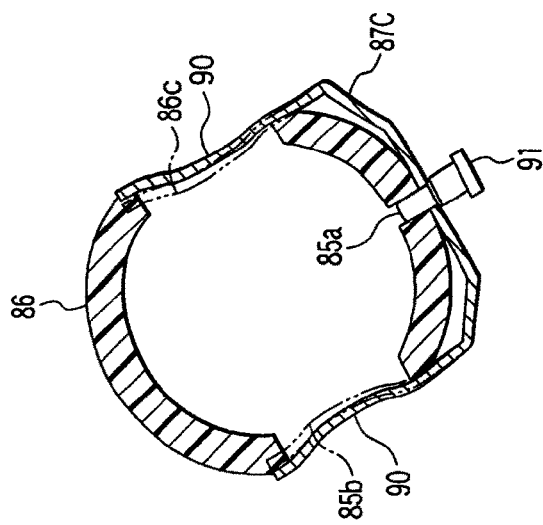
FIG. 48 is a cross-sectional view taken along line 48-48 in FIG. 37.
Figure 47:
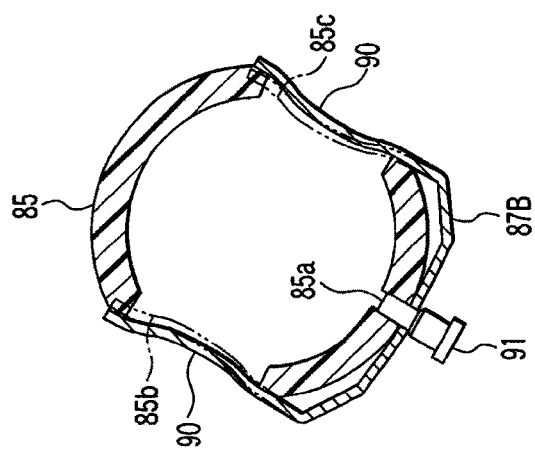
FIG. 47 is a cross-sectional view taken along line 47-47 in FIG. 37.
Figure 46:
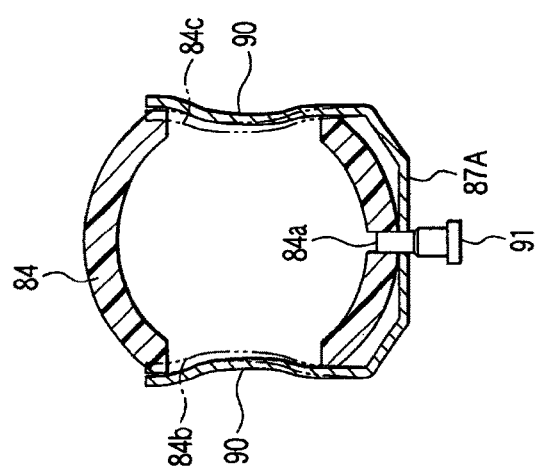
FIG. 46 is a cross-sectional view taken along line 46-46 in FIG. 37.

FIG. 46 shows the first electrode receiving section 84, FIG. 47 shows the second electrode receiving section 85, and FIG. 48 shows the third electrode receiving section 86.

As shown in FIG. 46, the first electrode receiving section 84 has one contact-point member fixing hole 84*a*, and two through-holes 84*b* and 84*c*. A center line of the two through-holes 84*b* and 84*c* is set to be perpendicular to a center line of the contact-point member fixing hole 84*a*.

Similarly, as shown in FIG. 47, the second electrode receiving section 85 has one contact-point member fixing hole 85*a*, and two through-holes 85*b* and 85*c*. As shown in FIG. 48, the third electrode receiving section 86 has one contact-point member fixing hole 86*a*, and two through-holes 86*b* and 86*c*.

The positions of the contact-point member fixing hole 84*a* of the first electrode receiving section 84, the contact-point member fixing hole 85*a* of the second electrode receiving section 85 and the contact-point member fixing hole 86*a* of the third electrode receiving section 86 are displaced in the circumferential direction of the electrode hold member 83.

FIG. 49 and FIG. 50 show electrode members 87A, 87B and 87C which are assembled to the first to third electrode receiving sections 84, 85 and 86. These electrode members 87A, 87B and 87C are formed in the same shape. In the description below, only the electrode member 87A, which is assembled to the first electrode receiving section 84, is described. The common parts of the electrode members 87B and 87C of the other second and third electrode receiving sections 85 and 86 are denoted by like reference numerals, and a description thereof is omitted.

The electrode member 87A includes one straight stationary portion 87*a* and two bend portions 87*b* and 87*c*. One bend portion 87*b* is disposed at one end of the straight stationary portion 87*a*, and the other bend portion 87*c* is disposed at the other end of the straight stationary portion 87*a*. Thereby, as shown in FIG. 49, the electrode member 87A is formed and bent in a substantially U shape.

A hole 88 and an L-shaped wiring connection portion 89 are provided at a central position of the stationary portion 87*a*. Inwardly curved waist portions 90 are formed at central positions of the two bend portions 87*b* and 87*c*.

When the first electrode receiving section 84 and the electrode member 87A are assembled, a fixing pin 91 is inserted in the hole 88 of the stationary portion 87*a* of the electrode member 87A and in the contact-point member fixing hole 84*a* of the first electrode receiving section 84. The electrode member 87A is fixed to the first electrode receiving section 84 by the fixing pin 91. At this time, the waist portion 90 of one bend portion 87*b* of the electrode member 87A is disposed in one through-hole 84*b* of the first electrode receiving section 84, and the waist portion 90 of the other bend portion 87*c* of the electrode member 87A is disposed in the other through-hole 84*c*. The same applies when the electrode member 87B is assembled to the second electrode receiving section 85 and the electrode member 87C is assembled to the third electrode receiving section 86.

As shown in FIG. 51, a large-diameter fixing flange portion 83*a* is formed at a rear end portion of the electrode hold member 83 of the contact-point unit 66. Engaging projection portions 83*b* are provided to project from the outer peripheral surface of the fixing flange portion 83*a* at a plurality of locations, for example, at three locations in this embodiment. Engaging recess portions 48*a* are formed in an inner peripheral surface of the rear end portion of the hold cylinder 48 at positions corresponding to the three engaging projection portions 83*b* of the stationary flange portion 83*a*. In the case where the electrode hold member 83 is assembled in the hold cylinder 48, the three engaging projection portions 83*b* of the stationary flange portion 83*a* are inserted, engaged and fixed in the engaging recess portions 48*a* of the hold cylinder 48. Thereby, the rotation of the electrode hold member 83 about the axis thereof, relative to the hold cylinder 48, is restricted.

A stepped portion 43*b*, which comes in contact with the fixing flange portion 83*a* of the electrode hold member 83, is formed on the hold cylinder 48. The electrode hold member 83 is fixed to the hold cylinder 48 by a fixing screw 48*c* in the state in which the fixing flange portion 83*a* of the electrode hold member 83 abuts upon the stepped portion 43*b*. Thereby, the axial movement of the electrode hold member 83, relative to the hold cylinder 48, is restricted.

End portions of three wiring lines 93*a* to 93*c*, which are assembled in the switch hold section 51, are connected to the wiring connection portions 89 of the three electrode members 87A, 87B and 87C that are assembled to the contact-point unit 66.

Further, as shown in FIG. 42, the contact-point unit 66 is provided with a substantially C-shaped electric contact-point member 96 which is formed of a metallic plate spring. The electric contact-point member 96 is connected to the outer-peripheral surface of the proximal end portion of the spring receiving member 64.

The handle-unit-side electric path 95 is composed of the electrical contact member 96, spring receiving member 64, positioning pin 81 and rotation transmission member 71.

A front end portion of the transducer unit 2 is detachably coupled to the contact-point unit 66. As shown in FIG. 52, two wiring lines 101 and 102 for the ultrasonic transducer, two wiring lines 103 and 104 for high-frequency power and three wiring lines 105, 106 and 107, which are connected to a wiring circuit board within the switch hold section 51, are assembled in the single cable 9 at the rear end of the transducer unit 2. Distal end portions of the two wiring lines 101 and 102 for the ultrasonic transducer are connected to the ultrasonic transducer 6. A distal end portion of one wiring line 103 for high-frequency power is connected to the ultrasonic transducer 6.

First to fourth electrically conductive plates 111 to 114 for electric connection are provided at the rear end of the transducer unit 2. A distal end portion of the other wiring line 104 for high-frequency power is connected to the first conductive plate 111. The three wiring lines 105, 106 and 107 are connected to the second to fourth conductive plates 112 to 114.

FIG. 4 shows the internal structure of a front end portion of the transducer unit 2. A connection cylindrical portion 121 is formed at the distal end portion of the transducer cover 7. A C-ring 122 having a partly cut-out annular plate shape is mounted on the outer peripheral surface of the connection cylindrical body 121. Three (first to third) cylindrical portions 123 to 125 with different outside diameters are projectingly provided on the inside of the connection cylindrical portion 121. The first cylindrical portion 123 has a smallest outside diameter and has a greatest length of projection from the distal end of the connection cylindrical body 121. The second cylindrical portion 124 has an outside diameter, which is greater than the outside diameter of the first cylindrical portion 123, and has a length of projection from the distal end of the connection cylindrical body 121, which is less than the length of projection of the first cylindrical portion 123. The third cylindrical portion 125 has a greatest outside diameter and has a length of projection from the distal end of the connection cylindrical body 121, which is less than the length of projection of the second cylindrical portion 124.

A first cylindrical contact-point member 131 is mounted on the outer peripheral surface of the first cylindrical portion 123. Similarly, a second cylindrical contact-point member 132 is mounted on the outer peripheral surface of the second cylindrical portion 124, and a third cylindrical contact-point member 133 is mounted on the outer peripheral surface of the third cylindrical portion 125. The second conductive plate 112 is connected to the first contact-point member 131, the third conductive plate 113 is connected to the second contact-point member 132, and the fourth conductive plate 114 is connected to the third contact-point member 133.

A fourth contact-point member 134 is mounted on the inner peripheral surface of the first cylindrical body 123. The fourth contact-point member 134 is connected to the first conductive plate 111.

When the handle unit 4 and the transducer unit 2 are coupled, the contact-point unit 66 of the handle unit 4 and the front end portion of the transducer unit 2 are connected. At this time, the electrode member 87A of the contact-point unit 66 and the first contact-point member 131 of the transducer unit 2 are connected. At the same time, the electrode member 87B of the contact-point unit 66 and the second contact-point member 132 of the transducer unit 2 are connected, the electrode member 87C of the contact-point unit 66 and the third contact-point member 133 of the transducer unit 2 are connected, and the C-shaped electric contact-point member 96 of the contact-point unit 66 and the fourth contact-point member 134 of the transducer unit 2 are connected.

Next, the operation of the present embodiment is described. The handpiece 1 of the ultrasonic therapeutic apparatus of the present embodiment, as shown in FIG. 2, comprises four units, namely, the transducer unit 2, probe unit 3, handle unit 4 and sheath unit 5, which are detachable. When the handpiece 1 is used, the transducer unit 2 and the probe unit 3 are coupled. Thereby, the first high-frequency electric path 13, which transmits a high-frequency current to the coupled body of the transducer unit 2 and probe unit 3, is formed.

Subsequently, the handle unit 4 and the sheath unit 5 are coupled. When the handle unit 4 and sheath unit 5 are coupled, the connection tube body 34 is inserted in the rotation transmission member 71 of the handle unit 4 in the state in which the handle member 32 of the sheath unit 5 is held. When the sheath unit 5 and handle unit 4 are coupled, the engaging lever 43 on the handle unit 4 side is held in the state in which the engaging lever 43 rests on the inclined surface of the guide groove 41 of the handle member 32 of the sheath unit 5, as shown in FIG. 29 and FIG. 30. At this time, as shown in FIG. 41A, the electrically conductive rubber ring 94*b* is held in the positional state in which the inner peripheral surface shape of the electrically conductive rubber ring 94*b* corresponds to the engaging portion 46 of the connection flange portion 33c, that is, in the state in which the three corner portions 46b of the connection flange portion 33c correspond in position to the three corner portions 94b2 of the electrically conductive rubber ring 94b. Accordingly, the connection flange portion 33c of the sheath unit 5 is inserted straight into the electrically conductive rubber ring 94b. At the time of this insertion operation, as shown in FIG. 41A, the conductive rubber ring 94b is held in the natural, non-compressed position. In this state, the sheath-unit-side electric path 40 and the handle-unit-side electric path 95 are not electrically connected.

Subsequently, following this insertion operation, the handle member 32 of the sheath unit 5 is rotated about the axis thereof, relative to the handle unit 4. By this operation, as shown in FIG. 31 and FIG. 32, the engaging lever 43 on the handle unit 4 side is inserted and engaged in the engaging recess portion 42 at one end portion of the guide groove 41. At this time, as shown in FIG. 41B, the electrically conductive rubber ring 94b is switched to the pressure contact position where the electrically conductive rubber ring 94b is put in pressure contact with the three corner portions 46b of the connection flange portion 33c. Thereby, the sheath-unit-side electric path 40 and the handle-unit-side electric path 95 are electrically connected via the electrically conductive rubber ring 94b. As a result, the second high-frequency electric path 97, which transmits a high-frequency current, is formed in the coupled body of the sheath unit 5 and handle unit 4.

When the sheath unit 5 is rotated about the axis thereof, the pair of engaging pins 45 on the handle unit 4 side are, at the same time, disengageably engaged in the engaging groove 44a at the terminal end portion of the guide groove 44 of the sheath unit 5. Thereby, the spring receiving member 64 on the handle unit 4 side and the connection tube body 34 on the sheath unit 5 side are coupled via the engaging pins 45. As a result, the operation force on the handle unit 4 side at the time when the movable handle 49 is closed relative to the stationary handle 47 can be transmitted to the driving pipe 19 of the jaw 17 on the sheath unit 5 side. This state is the coupled state between the sheath unit 5 and the handle unit 4.

Thereafter, the coupled body of the sheath unit 5 and handle unit 4 and the coupled body of the ultrasonic transducer 6 and probe unit 3 are assembled as one body. In this assembling work, the contact-point unit 66 of the handle unit 4 is connected to the front end portion of the transducer unit 2. At this time, the electrode member 87A of the contact-point unit 66 and the first contact-point member 131 of the transducer unit 2 are connected. At the same time, the electrode member 87B of the contact-point unit 66 and the second contact-point member 132 of the transducer unit 2 are connected, the electrode member 87C of the contact-point unit 66 and the third contact-point member 133 of the transducer unit 2 are connected, and the C-shaped electric contact-point member 96 of the contact-point unit 66 and the fourth contact-point member 134 of the transducer unit 2 are connected. Thereby, the second high-frequency electric path 97 of the coupled body of the sheath unit 5 and handle unit 4 is connected to the wiring line 104 for high-frequency power within the cable 9. Further, the three wiring lines 105, 106 and 107 within the cable 9 are connected to the wiring circuit board within the switch hold section 51. This state is the completion state of the assembly of the handpiece 1.

When the handpiece 1 is used, the movable handle 49 is opened/closed relative to the stationary handle 47. The driving pipe 19 is axially moved in interlock with the operation of the movable handle 49, and the jaw 17 is opened/closed, relative to the probe distal end portion 3a of the probe unit 3, in interlock with the advancing/retreating movement of the driving pipe 19 in its axial direction. When the movable handle 49 is closed relative to the stationary handle 47, the driving pipe 19 is pushed forward in interlock with the operation of the movable handle 49. The jaw 17 is rotated and driven (to a closed position) in a direction toward the probe distal end portion 3a of the probe unit 3 in interlock with the pushing operation of the driving pipe 19. By the rotation of the jaw 17 to its closed position, a living body tissue is held between the jaw 17 and the probe distal end portion 3a of the probe unit 3.

In this state, one of the switch button 54 for coagulation and the switch button 55 for incision, which are provided on the stationary handle 47, is selectively pressed. When the switch button 54 for coagulation is pressed, power is supplied to the first high-frequency electric path 13 for supplying a high-frequency current to the probe distal end portion 3a of the probe unit 3 and to the second high-frequency electric path 97 for supplying a high-frequency current to the jaw body of the sheath unit 5. Thereby, the two bipolar electrodes for high-frequency therapeutic treatment are constituted by the probe distal end portion 3a of the probe unit 3 and the jaw body of the sheath unit 5. By supplying a high-frequency current between the two bipolar electrodes which are constituted by the probe distal end portion 3a of the probe unit 3 and the jaw body of the sheath unit 5, bipolar high-frequency therapeutic treatment can be performed for the living body tissue between the jaw 17 and the probe distal end portion 3a of the probe unit 3.

When the switch button 55 for incision is pressed, a driving current is supplied to the ultrasonic transducer 6 at the same time as the supply of high-frequency current, and the ultrasonic transducer 6 is driven. At this time, ultrasonic vibration from the ultrasonic transducer 6 is transmitted to the probe distal end portion 3a via the vibration transmission member 11. Thereby, incision, resection, etc. of the living body tissue can be performed by making use of ultrasonic at the same time as the supply of high-frequency current. In the meantime, coagulation for the living body tissue can be performed by using ultrasonic.

When the movable handle 49 is opened relative to the stationary handle 47, the driving pipe 19 is pulled to the proximal side in interlock with the opening operation of the removable handle 49. The jaw 17 is driven (to an open position) in a direction away from the probe distal end portion 3a of the probe unit 3 in interlock with the pulling operation of the driving pipe 19.

When the rotational operation knob 50 is rotated, the rotational movement of the rotation transmission member 71, which rotates together with the rotational operation knob 50, is transmitted to the spring receiving member 64 side via the pin 81. Thereby, when the rotational operation knob 50 is rotated, the assembly unit of the rotation transmission member 71, pin 81, spring receiving member 64, slider member 65 and coil spring 67 within the hold cylinder 48 is rotated together with the rotational operation knob 50 as one body about the axis thereof. Further, the rotational operation force of the rotational operation knob 50 is transmitted to the vibration transmission member 11 of the probe unit 3 via the tubular member 98 that rotates together with the spring receiving member 64 within the hold cylinder 48. Thereby, the assembly unit within the hold cylinder 48 and the coupled body of the transducer unit 2 and probe unit 3 are rotated about the axis as one body.

At this time, the handle member 32 and guide cylindrical body 33 of the sheath unit 5 rotate together with the rotational operation knob 50. Furthermore, the sheath 18 rotates together with the guide cylindrical body 33, and the rotation of the guide cylindrical body 33 is transmitted to the connection tube body 34 and driving pipe 19 via the threaded pin 235. Thus, the jaw 17 and probe distal end portion 3*a* of the therapeutic section 1A are rotated about the axis at the same time together with the rotational operation knob 50.

The following advantageous effects can be obtained by the above-described structure. Specifically, in the handpiece 1 of the ultrasonic therapeutic apparatus of the present embodiment, the jaw 17 has the distal end chip 208 at a distal end portion of the engaging surface 206 for engagement with the probe distal end portion 3*a*. When the jaw 17 and probe distal end portion 3*a* are engaged, a positional displacement relative to the probe distal end portion 3*a* is tolerated by the distal end chip 208. Even in the case where a positional displacement occurs in the assembly position between the jaw 17 and the probe distal end portion 3*a* in the axial direction of the probe unit 3 when the probe unit 3 and the sheath unit 5 are assembled and the jaw 17 is positioned to face the probe distal end portion 3*a* of the probe unit 3, the distal end of the probe distal end portion 3*a* can exactly be put in contact with the distal end chip 208 which is the insulator. As a result, a fixed amount of clearance can be kept between the electrode member 203 of the jaw 17 and the probe distal end portion 3*a* after assembly, and contact between the electrode member 203 of the jaw 17 and the probe distal end portion 3*a* can be prevented. Since the bipolar high-frequency therapeutic function can be secured, it is not necessary to precisely manage a fabrication error of parts of the apparatus and an error in assembly, and the manufacturing cost can be reduced.

Moreover, in the present embodiment, in the jaw 17, the entire distal end portion of the engaging surface 206 for engagement with the probe distal end portion 3*a* is formed by the distal end chip 208. Thus, when the probe unit 3 and the sheath unit 5 are assembled, even if a positional displacement occurs in either the longitudinal direction or transverse direction between the jaw 17 and the probe distal end portion 3*a*, the clearance between the electrode member 203 of the jaw 17 and the probe distal end portion 3*a* after assembly can surely be secured.

As shown in FIGS. 17 and 19, the jaw 17 has, at the distal end portion of the groove portion 205, the distal-end-side groove width varying section 205*t*1 which has such a tapering shape that the groove width of the groove portion 205 gradually increases toward the distal end. Thereby, when the probe unit 3 and the sheath unit 5 are assembled, even if a positional displacement occurs in either the longitudinal direction or transverse direction between the jaw 17 and the probe distal end portion 3*a*, the positional displacement can be tolerated by the distal-end-side groove width varying section 205*t*1. As a result, the clearance between the electrode member 203 of the jaw 17 and the probe distal end portion 3*a* after assembly can surely be secured.

In addition, the jaw 17 has, at the proximal end portion of the groove portion 205, the proximal-end-side groove width varying section 205*t*2 which has such a tapering shape that the groove width of the groove portion 205 gradually increases toward the proximal end. Thereby, when the probe unit 3 and the sheath unit 5 are assembled, even if a positional displacement occurs in either the longitudinal direction or transverse direction between the jaw 17 and the probe distal end portion 3*a*, the positional displacement can be tolerated by the proximal-end-side groove width varying section 205*t*2. As a result, the clearance between the electrode member 203 of the jaw 17 and the probe distal end portion 3*a* after assembly can surely be secured.

The jaw 17 has the tooth portions 203*b* for preventing a slip, which are formed on both side walls 203*a* of the groove portion 205 of the electrode member 203. Thus, when the jaw 17 and probe distal end portion 3*a* are engaged, the tooth portions 203*b* can be made to bite into a clamped object between the probe distal end portion 3*a* and the jaw 17. Thereby, a slip of the clamped object between the probe distal end portion 3*a* and the jaw 17 can be prevented.

Figure 53:
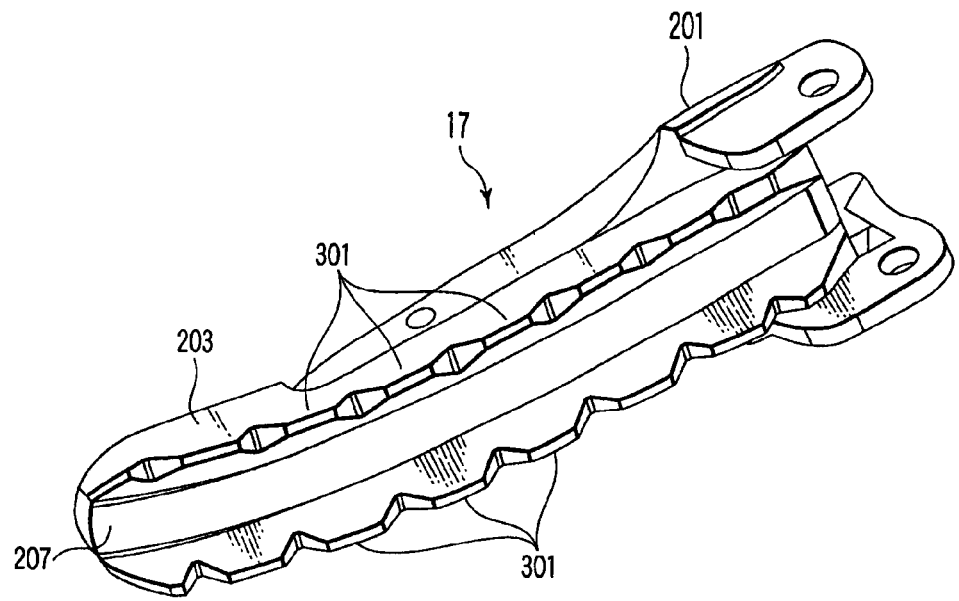
FIG. 53 is a perspective view showing the structure of a jaw of an ultrasonic therapeutic apparatus according to a second embodiment of the present invention.

FIG. 53 shows a second embodiment of the ultrasonic therapeutic apparatus of the present invention. In this embodiment, the structure of the jaw 17 in the first embodiment (see FIG. 1 to FIG. 52) is altered as follows. In the jaw 17 of this embodiment, a plurality of substantially trapezoidal teeth 301 are juxtaposed on both side walls 203*a* of the electrode member 203.

The following advantageous effects can be obtained by the above-described structure. Specifically, in the jaw 17 of the present embodiment, the substantially trapezoidal teeth 301 are provided on the hold surface that comes in contact with a living body tissue. Thus, when the jaw 17 and probe distal end portion 3*a* are engaged, the trapezoidal teeth 301 can be made to bite into a clamped object between the probe distal end portion 3*a* and the jaw 17. Thereby, a slip of the clamped object between the probe distal end portion 3*a* and the jaw 17 can be prevented.

Furthermore, the trapezoidal teeth 301 have obtuse-angled corner portions, and have no acute-angled edge portions. In the case where the electrode member 203 of the jaw 17 has acute-angled edge portions, electricity concentrates at the acute-angled edge portions of the electrode member 203. Consequently, a spark occurs between the edge portion of the jaw 17 and the probe distal end portion 3*a*. Owing to the occurrence of the spark, heat will concentrate and the living body tissue may be burnt. By contrast, in the jaw 17 of this embodiment, since corner portions of the trapezoidal teeth 301 have obtuse-angled shapes, no spark occurs between the jaw 17 and the probe distal end portion 3*a*, and burning of the living body tissue can be prevented.

Figure 54:
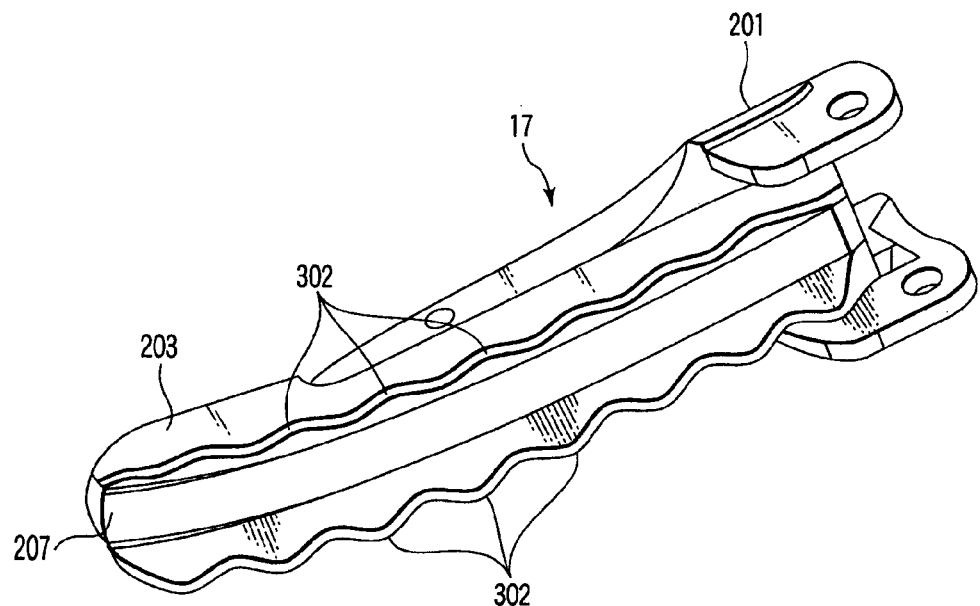
FIG. 54 is a perspective view showing the structure of a jaw of an ultrasonic therapeutic apparatus according to a third embodiment of the present invention.

FIG. 54 shows a third embodiment of the ultrasonic therapeutic apparatus of the present invention. In this embodiment, the structure of the jaw 17 in the first embodiment (see FIG. 1 to FIG. 52) is altered as follows. In the jaw 17 of this embodiment, a plurality of large-wavy-shaped teeth 302 are juxtaposed on both side walls 203*a* of the electrode member 203.

The following advantageous effects can be obtained by the above-described structure. Specifically, in the jaw 17 of the present embodiment, the large-wavy-shaped teeth 302 are provided on the hold surface that comes in contact with a living body tissue. Thus, when the jaw 17 and probe distal end portion 3*a* are engaged, the wavy-shaped teeth 302 can be made to bite into a clamped object between the probe distal end portion 3*a* and the jaw 17. Thereby, a slip of the clamped object between the probe distal end portion 3*a* and the jaw 17 can be prevented.

Furthermore, since the large-wavy-shaped teeth 302 have no corner portions and have gently curved shapes, no acute-angled edge portions are formed. In this embodiment, like the second embodiment (see FIG. 53), no spark occurs between the jaw 17 and the probe distal end portion 3*a*, and burning of the living body tissue can be prevented.

FIG. 55 shows a fourth embodiment of the ultrasonic therapeutic apparatus of the present invention. In this embodiment, the structure of the jaw 17 in the first embodiment (see FIG. 1 to FIG. 52) is altered as follows. In the jaw 17 of this embodiment, a plurality of small-wavy-shaped teeth 303 are juxtaposed on both side walls 203a of the electrode member 203.

The following advantageous effects can be obtained by the above-described structure. Specifically, in the jaw 17 of the present embodiment, the small-wavy-shaped teeth 303 are provided on the hold surface that comes in contact with a living body tissue. Thus, when the jaw 17 and probe distal end portion 3a are engaged, the wavy-shaped teeth 303 can be made to bite into a clamped object between the probe distal end portion 3a and the jaw 17. Thereby, a slip of the clamped object between the probe distal end portion 3a and the jaw 17 can be prevented.

Furthermore, since the small-wavy-shaped teeth 303 have no corner portions and have gently curved shapes, no acute-angled edge portions are formed. In this embodiment, like the second embodiment (see FIG. 53), no spark occurs between the jaw 17 and the probe distal end portion 3a, and burning of the living body tissue can be prevented.

FIG. 56 shows a fifth embodiment of the ultrasonic therapeutic apparatus of the present invention. In this embodiment, the structure of the jaw 17 in the first embodiment (see FIG. 1 to FIG. 52) is altered as follows. In the jaw 17 of this embodiment, planar hold surfaces 304 with no teeth are formed on both side walls 203a of the electrode member 203.

The following advantageous effects can be obtained by the above-described structure. Specifically, in the jaw 17 of the present embodiment, the planar hold surfaces 304 on both side walls 203a of the electrode member 203 are put in contact with a living body tissue. Thus, no spark occurs between the jaw 17 and the probe distal end portion 3a, and burning of the living body tissue can be prevented.

Figure 57:
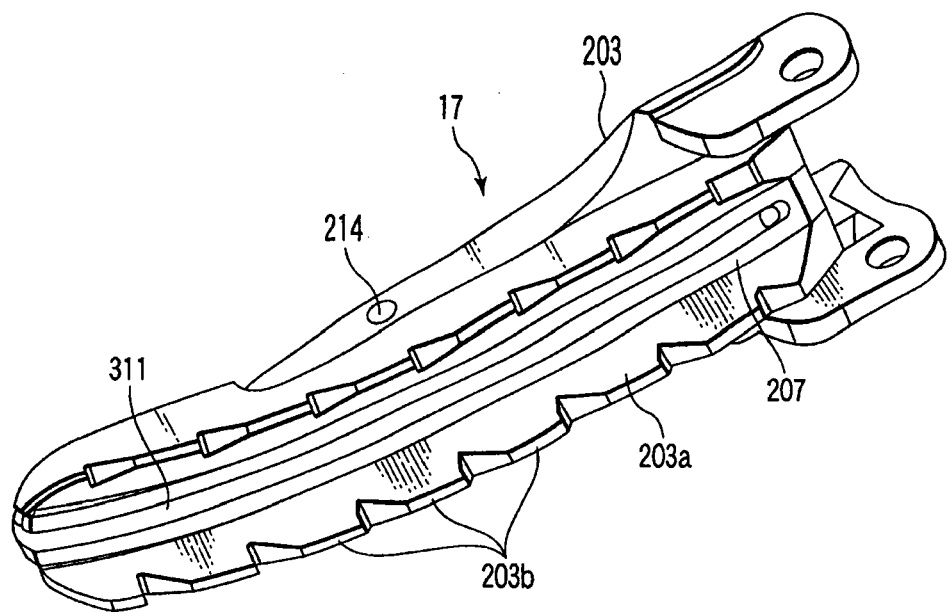
FIG. 57 is a perspective view showing the structure of a jaw of an ultrasonic therapeutic apparatus according to a sixth embodiment of the present invention.
Figure 58:
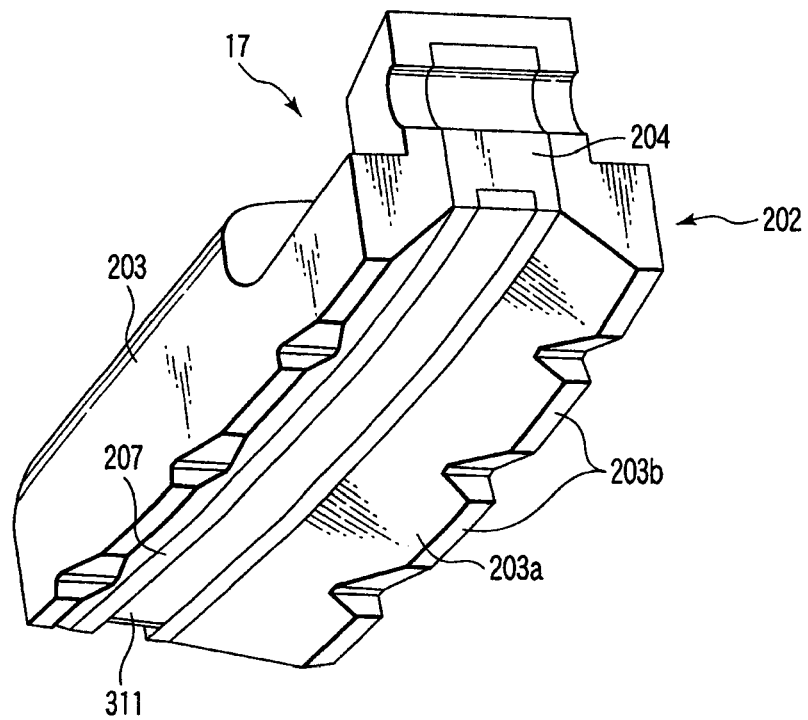
FIG. 58 is a perspective view showing a back side of the jaw of the ultrasonic therapeutic apparatus according to the sixth embodiment.
Figure 62:
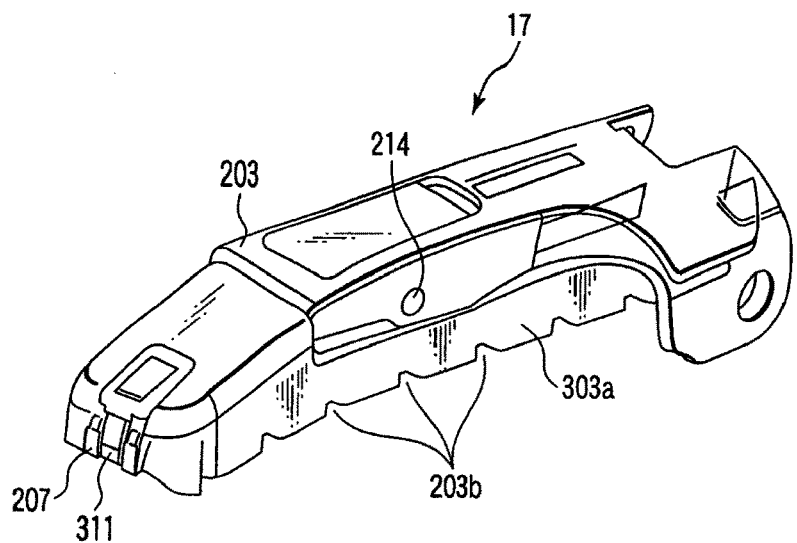
FIG. 62 is a perspective view showing the structure of a jaw of an ultrasonic therapeutic apparatus according to a seventh embodiment of the present invention.

FIGS. 57 to 61 show a sixth embodiment of the present invention. In this embodiment, the structure of the jaw 17 in the first embodiment (see FIG. 1 to FIG. 52) is altered as follows. FIG. 57 shows the external appearance of the jaw 17 of this embodiment. As shown in FIGS. 58 and 59, in the jaw 17 of this embodiment, the pad member 207, which is formed of an insulator, has an outer contact surface that comes in contact with the probe distal end portion 3a, and this contact surface is provided with a wear-prevention portion 311 for preventing wear of the pad member 207.

FIG. 60 shows the external appearance of the pad member 207. A mounting groove 312 for mounting the wear-prevention portion 311 is provided in the outer contact surface of the pad member 207, which comes in contact with the probe distal end portion 3a. Further, a front end fixing portion 313a for fixing a front end of the wear-prevention portion 311 is formed at a front end portion of the pad member 207, and a rear end fixing portion 313b for fixing a rear end of the wear-prevention portion 311 is formed at a rear end portion of the pad member 207.

The wear-prevention portion 311 in this embodiment includes, for example, an elongated plate-shaped metallic pad 314 which is formed of a metallic material. FIG. 61 shows the metallic pad 314. A front end bend portion 315, which is attached to the front end fixing portion 313a of the pad member 207, is formed at a front end portion of the metallic pad 314. Similarly, a rear end bend portion 316, which is attached to the rear end fixing portion 313b of the pad member 207, is formed at a rear end portion of the metallic pad 314.

The front end bend portion 315 of the metallic pad 314 is attached to the front end fixing portion 313a of the pad member 207, and the rear end bend portion 316 of the metallic pad 314 is attached to the rear end fixing portion 313b of the pad member 207. In addition, the metallic pad 314 is inserted in the mounting groove 312 of the pad member 207. In this state, the metallic pad 314 is fixed to the pad member 207. As shown in FIG. 59, the pad member 207 is interposed between the metallic pad 314 and the electrode member 203. Thereby, the metallic pad 314 and the electrode member 203 are electrically insulated.

The following advantageous effect can be obtained by the above-described structure. Specifically, in the jaw 17 of this embodiment, the outer contact surface of the pad member 207, which comes in contact with the probe distal end portion 3a, has the metallic pad 314 for preventing wear of the pad member 207. Thereby, the pad member 207 of the jaw 17 is prevented from coming in direct contact with the probe distal end portion 3a. Therefore, the pad member 207 of the jaw 17 can be prevented from being worn due to contact with the probe distal end portion 3a. As a result, the wear-resistance properties of the part of the jaw 17, which comes in contact with the probe distal end portion 3a, can be improved.

The wear-prevention portion 311 is not necessarily limited to the metallic pad 314 of the metallic material. For instance, the wear-prevention portion 311 may be formed of a ceramic material, a hard resin material, etc.

FIGS. 62 to 68 show a seventh embodiment of the present invention. In this embodiment, the structure of the jaw 17 in the sixth embodiment of the invention (see FIG. 57 to FIG. 61) is altered as follows.

Figure 63:
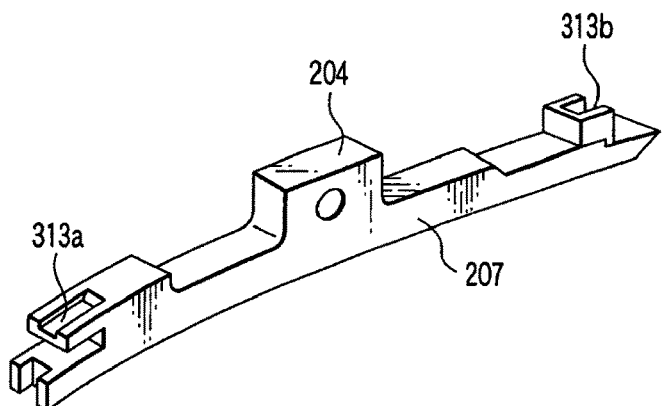
FIG. 63 is a perspective view showing an insulation member of the jaw of the ultrasonic therapeutic apparatus according to the seventh embodiment.
Figure 64:
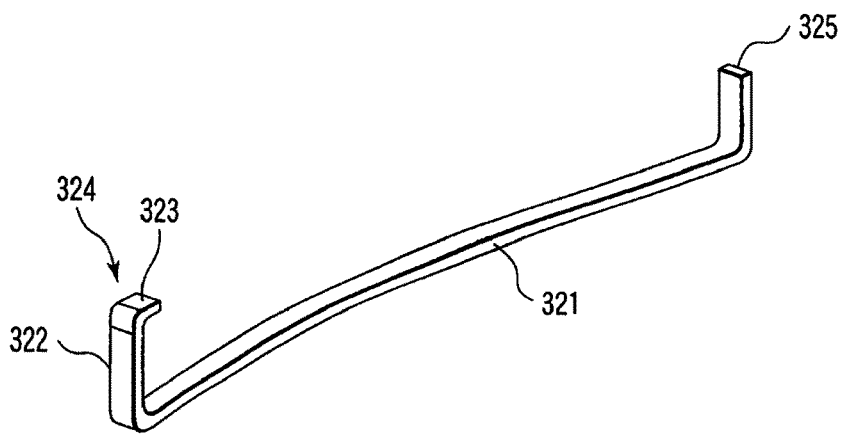
FIG. 64 is a perspective view showing a metallic plate before a metallic pad of the jaw of the ultrasonic therapeutic apparatus according to the seventh embodiment is bent.

Specifically, in this embodiment, a metallic pad 314 is assembled to an insulation member 204 shown in FIG. 63 by bending a metallic plate 321 shown in FIG. 64. A recess-shaped front end fixing portion 313a for fixing a front end of the metallic pad 314 is formed at a front end portion of the insulation member 204, and a recess-shaped rear end fixing portion 313b for fixing a rear end of the metallic pad 314 is formed at a rear end portion of the insulation member 204.

FIG. 64 shows a metallic plate 321 prior to bending of the metallic pad 314 of the jaw 17. A front end bend portion 322, which is bent substantially at right angles, is formed at a front end portion of the metallic plate 321. A small bend portion 323, which is bent at right angles, is further formed at a distal end portion of the front end bend portion 322. A substantially L-shaped bend portion 324 is formed of the front end bend portion 322 and the small bend portion 323. A rear end bend portion 325, which is bent substantially at right angles, is formed at a rear end portion of the metallic plate 321.

FIG. 65 illustrates a first step of assembling the metallic pad 314 to the insulation member 204 of the jaw 17. In this step, the L-shaped bend portion 324 of the metallic plate 321 is engaged and fixed in the front end fixing portion 313a of the insulation member 204.

Figure 66:
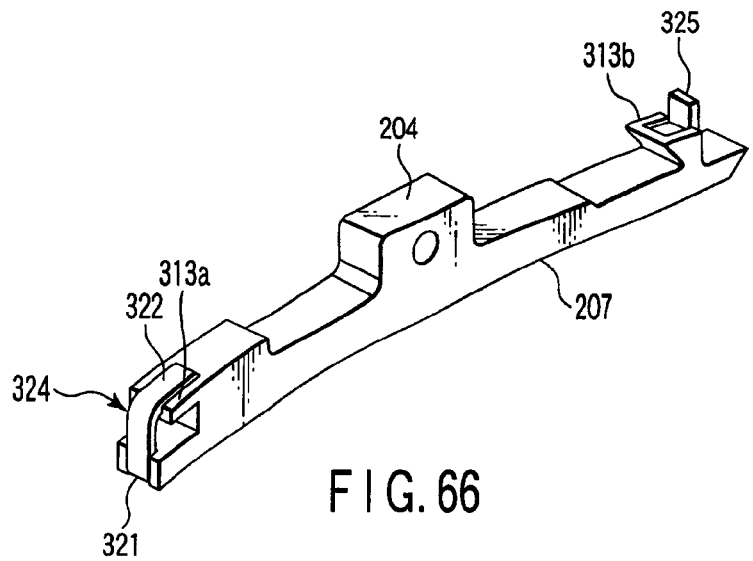
FIG. 66 is a perspective view showing a second step of bending the metallic plate which is assembled to the insulation member of the jaw of ultrasonic therapeutic apparatus according to the seventh embodiment is bent.

FIG. 66 illustrates a second step of assembling the metallic pad 314 to the insulation member 204 of the jaw 17. In this step, the metallic plate 321 shown in FIG. 65 is further bent in the vicinity of the L-shaped bend portion 324 in accordance with the shape of the front end fixing portion 313a of the insulation member 204. The rear end bend portion 325 of the metallic plate 321 is moved to the position of the rear end fixing portion 313b of the insulation member 204.

Figure 67:
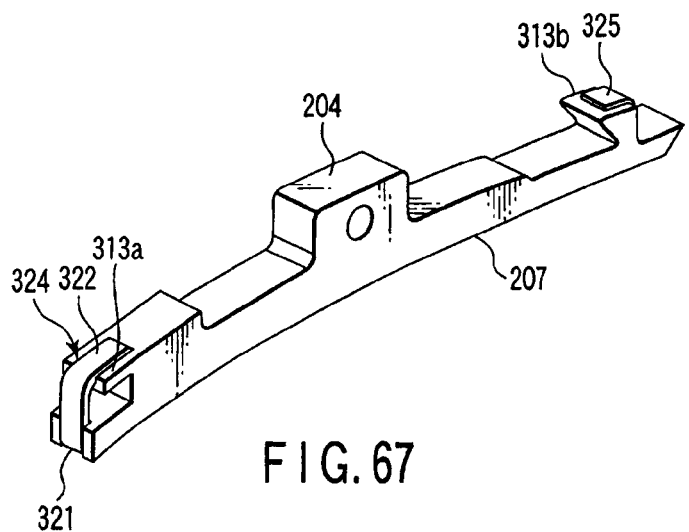
FIG. 67 is a perspective view showing a third step of bending the metallic plate which is assembled to the insulation member of the jaw of ultrasonic therapeutic apparatus according to the seventh embodiment is bent.
Figure 68:
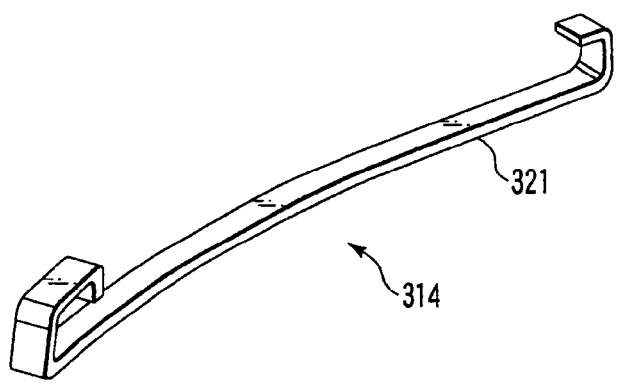
FIG. 68 is a perspective view showing the shape of the bent metallic pad which is assembled to the insulation member of the jaw of ultrasonic therapeutic apparatus according to the seventh embodiment is bent.

FIG. 67 illustrates a third step of assembling the metallic pad 314 to the insulation member 204 of the jaw 17. In this step, the rear end bend portion 325 of the metallic plate 321 shown in FIG. 66 is further bent in accordance with the shape of the rear end fixing portion 313b of the insulation member 204. The rear end bend portion 325 of the metallic plate 321 is engaged and fixed in the rear end fixing portion 313b of the insulation member 204. Thereby, the bending process for assembling the metallic pad 314 to the insulation member 204 of the jaw 17 is completed. FIG. 68 shows the shape of the metallic pad 314 of the jaw 17 after the bending process.

The following advantageous effects can be obtained by the above-described structure. Specifically, in the jaw 17 of the present embodiment, the metallic pad 314 is assembled to the insulation member 204 shown in FIG. 63 by bending the metallic plate 321 shown in FIG. 64. Therefore, the metallic pad 314 can be assembled in the insulation member 204 by a simple work, and the jaw 17 can be manufactured at low cost.

Figure 69:
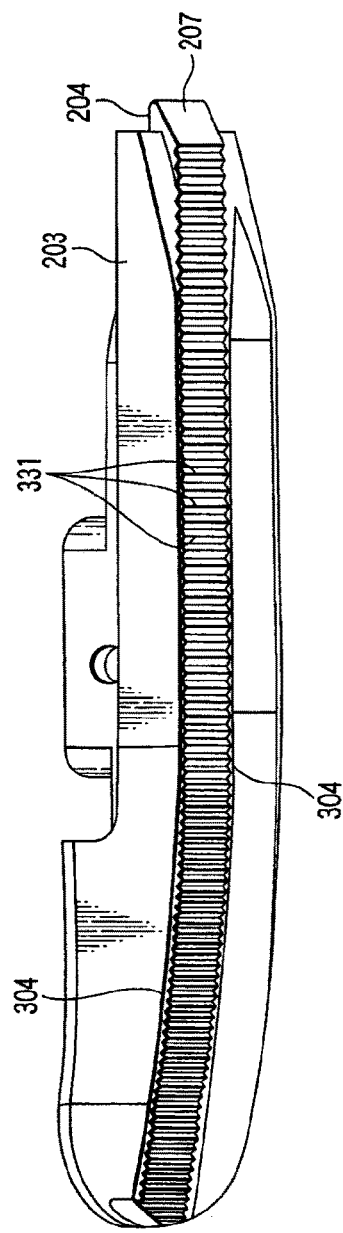
FIG. 69 is a perspective view showing the structure of a jaw of an ultrasonic therapeutic apparatus according to an eighth embodiment of the present invention.
Figure 70:
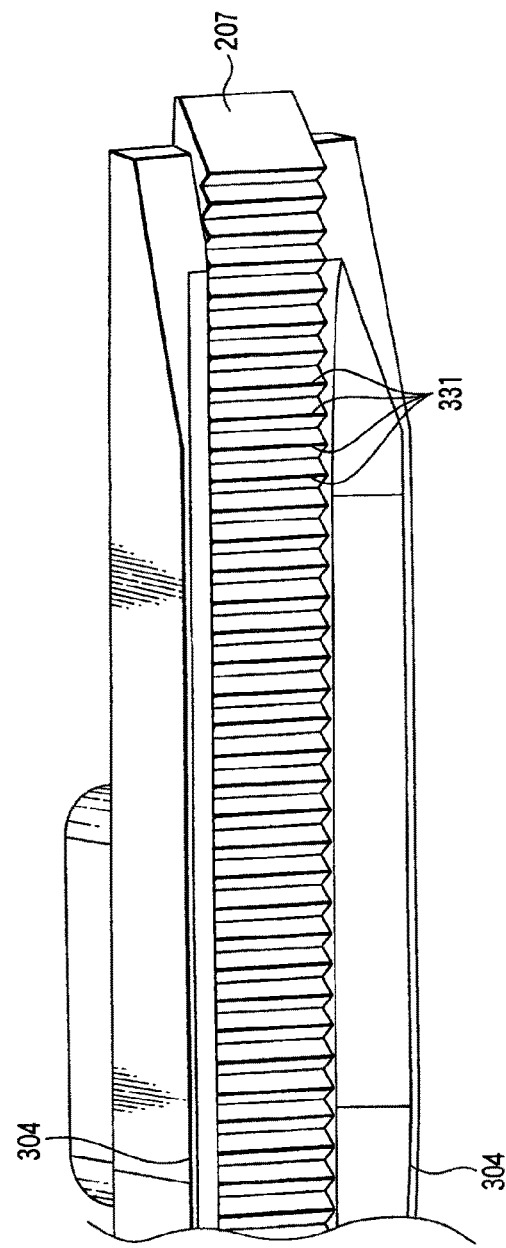
FIG. 70 is a perspective view showing the teeth of the jaw of the ultrasonic therapeutic apparatus according to the eighth embodiment.

FIG. 69 and FIG. 70 show an eighth embodiment of the present invention. In this embodiment, the structure of the jaw 17 in the fifth embodiment of the invention (see FIG. 56) is altered as follows.

Specifically, in the jaw 17 of this embodiment, planar hold surfaces 304 with no teeth are formed on both side walls 203a of the electrode member 203. Further, a plurality of teeth 331 are juxtaposed on the outer contact surface of the pad member 207 of the insulator, which comes in contact with the probe distal end portion 3a.

The following advantageous effects can be obtained by the above-described structure. Specifically, in the jaw 17 of the present embodiment, the planar hold surfaces 304 on both side walls 203a of the electrode member 203 are put in contact with a living body tissue. Thus, no spark occurs between the jaw 17 and the probe distal end portion 3a, and burning of the living body tissue can be prevented.

Moreover, in the present embodiment, the plural teeth 331 are juxtaposed on the outer contact surface of the pad member 207, which comes in contact with the probe distal end portion 3a. Thus, when the jaw 17 and probe distal end portion 3a are engaged, the teeth 331 of the pad member 207 can be made to bite into a clamped object between the probe distal end portion 3a and the jaw 17. Thereby, a slip of the clamped object between the probe distal end portion 3a and the jaw 17 can be prevented.

Figure 71:
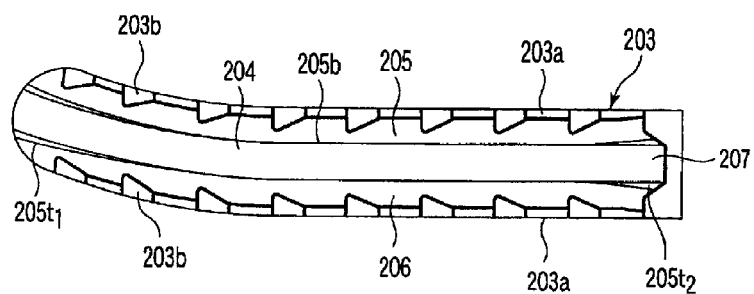
FIG. 71 is a plan view showing the structure of a jaw of an ultrasonic therapeutic apparatus according to a ninth embodiment of the present invention.

FIG. 71 shows a ninth embodiment of the present invention. In this embodiment, the structure of the jaw 17 in the first embodiment (see FIG. 1 to FIG. 52) is altered as follows. Specifically, in this embodiment, the distal end chip 208 at the distal end portion of the jaw 17 is dispensed with. In addition, the distal-end-side groove width varying section 205t1, which is provided at the distal end portion of the groove portion 205 of the electrode member 203 of the jaw 17, is extended to the distal end of the electrode member 203.

In the above-described structure, the electrode member 203 can be extended up to the foremost distal end of the jaw 17. Therefore, when therapeutic treatment by the handpiece 1 is performed, the high-frequency therapeutic treatment can be performed up to the foremost position of the jaw 17, and thus the range of high-frequency therapeutic treatment by the jaw 17 can be increased.

Needless to say, the present invention is not limited to the above-described embodiments, and various modifications may be made without departing from the spirit of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A probe comprising:
    a probe distal end body comprising a first electrode;
    a vibration transmission body removably connected to the probe distal end body,
        wherein the vibration transmission body is configured to transmit ultrasonic vibration generated by an ultrasonic transducer remote from the probe distal end body to the probe distal end body by mechanical vibration transmission, and to transmit current to the first electrode, and
        wherein an interior surface of the probe distal end body and an interior surface of the vibration transmission body define an interior space; and
    a heat dissipation unit,
        wherein at least a portion of the heat dissipation unit is arranged in the interior space defined by the probe distal end body and the vibration transmission body, and
        wherein the heat dissipation unit is configured to dissipate heat, generated remotely from the ultrasonic transducer at the probe distal end body by one or both of the mechanical vibration transmission and the current, along the at least a portion of the heat dissipation unit arranged in the interior space and away from the probe distal end body,
    wherein the interior space extends along a longitudinal axis between a distal end and a proximal end,
    wherein the distal end of the interior space is closed, and
    wherein the distal end of the interior space corresponds with a first node position of the ultrasonic vibration.

2. The probe according to claim 1,
    wherein the heat dissipation unit comprises a heat pipe arranged in the interior space defined by the interior surface of the probe distal end body and the interior surface of the vibration transmission body.

3. The probe according to claim 2,
    wherein a distal end portion of the heat pipe is thermally coupled to the probe distal end body such that the distal end portion is configured to absorb thermal energy generated by the probe distal end body to heat a working fluid of the heat pipe from a fluid phase into a vapor phase, and
    wherein a proximal end portion of the heat pipe is configured to recondense the working fluid from the vapor phase back to the fluid phase to release the thermal energy at a position away from the distal end portion of the heat pipe.

4. The probe according to claim 1,
    wherein the heat dissipation unit comprises a heat dissipating core material arranged in the interior space defined by the interior surface of the probe distal end body and the interior surface of the vibration transmission body.

5. The probe according to claim 4,
    wherein the vibration transmission body comprises a first material having a first thermal conductivity, and
    wherein the heat dissipating core material comprises a second material having a second thermal conductivity that is higher than the first thermal conductivity.

6. The probe according to claim 5,
    wherein the first material is stainless steel and the second material is graphite.

7. The probe according to claim 1,
wherein the heat dissipation unit comprises a closed loop coolant circulation system comprising:
   a coolant tubing comprising an input tubing segment and an output tubing segment arranged within the interior space defined by the probe distal end body and the vibration transmission body, wherein the input tubing segment is in thermal contact with the probe distal end body;
   a coolant pump; and
   a heat exchanger,
   wherein the coolant pump is configured to pump a coolant that is heated by thermal energy from the probe distal end body from the input tubing segment through the output tubing segment to the heat exchanger,
   wherein the heat exchanger is configured to dissipate the thermal energy in the heated coolant, and
   wherein the coolant pump is configured to pump the coolant from the heat exchanger through the input tubing segment toward the probe distal end body.

8. The probe according to claim 7,
wherein the interior space extends through a proximal end of the vibration transmission body, and
wherein the input tubing segment and the output tubing segment extend proximally through the proximal end of the vibration transmission body.

9. The probe according to claim 7,
wherein the vibration transmission body defines a port connecting the interior surface of the vibration transmission body and an external surface of the vibration transmission body, and
wherein the input tubing segment and the output tubing segment extend proximally through the port.

10. The probe according to claim 1,
wherein the vibration transmission body is comprised of stainless steel.

11. The probe according to claim 1,
wherein the first electrode is one of a pair of bipolar electrodes, wherein the first electrode is electrically connected to a first electric path through which the current is transmitted, and
wherein the probe further comprises an end effector configured to move relative to the probe distal end body to change a distance between the end effector and the probe distal end body, wherein the end effector comprises a second electrode that is another of the pair of bipolar electrodes, the second electrode being configured to be electrically connected to a second electric path through which the current is transmitted.

12. The probe according to claim 11,
wherein the heat dissipation unit comprises a heat pipe arranged in the interior space defined by the interior surface of the probe distal end body and the interior surface of the vibration transmission body.

13. The probe according to claim 12,
wherein a distal end portion of the heat pipe is thermally coupled to the probe distal end body such that the distal end portion is configured to absorb thermal energy generated by the probe distal end body to heat a working fluid of the heat pipe from a fluid phase into a vapor phase, and
wherein a proximal end portion of the heat pipe is configured to recondense the working fluid from the vapor phase back to the fluid phase to release the thermal energy at a position away from the distal end portion of the heat pipe.

14. The probe according to claim 11,
wherein the heat dissipation unit comprises a heat dissipating core material arranged in the interior space defined by the interior surface of the probe distal end body and the interior surface of the vibration transmission body.

15. The probe according to claim 14,
wherein the vibration transmission body comprises a first material having a first thermal conductivity, and
wherein the heat dissipating core material comprises a second material having a second thermal conductivity that is higher than the first thermal conductivity.

16. The probe according to claim 15,
wherein the first material is stainless steel and the second material is graphite.

17. The probe according to claim 11,
wherein the heat dissipation unit comprises a closed loop coolant circulation system comprising:
   a coolant tubing comprising an input tubing segment and an output tubing segment arranged within the interior space defined by the probe distal end body and the vibration transmission body, wherein the input tubing segment is in thermal contact with the probe distal end body;
   a coolant pump; and
   a heat exchanger,
   wherein the coolant pump is configured to pump a coolant that is heated by thermal energy from the probe distal end body from the input tubing segment through the output tubing segment to the heat exchanger,
   wherein the heat exchanger is configured to dissipate the thermal energy in the heated coolant, and
   wherein the coolant pump is configured to pump the coolant from the heat exchanger through the input tubing segment toward the probe distal end body.

18. The probe according to claim 11,
wherein the vibration transmission body is comprised of stainless steel.

19. The probe according to claim 11,
wherein the vibration transmission body is configured to transmit ultrasonic vibration generated by the ultrasonic transducer remote from the probe distal end body to the probe distal end body by mechanical vibration transmission while the heat dissipation unit dissipates the heat generated at the probe distal end body along the at least a portion of the heat dissipation unit arranged in the interior space defined by the probe distal end body and the vibration transmission body and away from the probe distal end body.

20. The probe according to claim 1,
wherein the interior space extends through a proximal end of the vibration transmission body.

21. The probe according to claim 20, further comprising:
a horn arranged at the proximal end of the vibration transmission body,
wherein an interior surface of the horn further defines the interior space, and the interior space extends through a proximal end of the horn.

22. The probe according to claim 1,
wherein the vibration transmission body is configured to transmit ultrasonic vibration generated by the ultrasonic transducer remote from the probe distal end body to the probe distal end body by mechanical vibration transmission while the heat dissipation unit dissipates the heat generated at the probe distal end body along the at least a portion of the heat dissipation unit arranged in the interior space defined by the probe distal end body and the vibration transmission body and away from the probe distal end body.

23. The probe according to claim 1, wherein the proximal end of the interior space is closed.

24. The probe according to claim 23, wherein the proximal end of the interior space corresponds with a second node position of the ultrasonic vibration.

25. The probe according to claim 23, wherein the vibration transmission body defines a port connecting the interior surface of the vibration transmission body and an external surface of the vibration transmission body.

26. The probe according to claim 25, wherein the vibration transmission body is configured to provide at least:
    the first node position of the ultrasonic vibration; and
    a second node position of the ultrasonic vibration closer to the proximal end of the interior space than the first node position of the ultrasonic vibration, and
    wherein the port is arranged at the second node position of the ultrasonic vibration.

27. The probe according to claim 1, wherein the vibration transmission body is removably connected to the proximal end of the probe distal end body by a threaded connection.

28. The probe according to claim 27, wherein the vibration transmission body is formed of a first material, and the probe distal end body is formed of a second material different from the first material.

29. The probe according to claim 27, wherein a section of the interior surface of the probe distal end body that defines the interior space has a same diameter as a section of the interior surface of the vibration transmission body that defines the interior space.

30. The probe according to claim 1, wherein the distal end of the interior space that is closed is arranged within the probe distal end body.

31. A probe comprising:
    a probe distal end body comprising a first electrode;
    a vibration transmission body removably connected to the probe distal end body,
        wherein the vibration transmission body is configured to transmit ultrasonic vibration generated by an ultrasonic transducer remote from the probe distal end body to the probe distal end body by mechanical vibration transmission, and to transmit current to the first electrode, and
        wherein an interior surface of the probe distal end body and an interior surface of the vibration transmission body define an interior space; and
    a heat dissipation unit,
        wherein at least a portion of the heat dissipation unit is arranged in the interior space defined by the probe distal end body and the vibration transmission body, and
        wherein the heat dissipation unit is configured to dissipate heat, generated remotely from the ultrasonic transducer at the probe distal end body by one or both of the mechanical vibration transmission and the current, along the at least a portion of the heat dissipation unit arranged in the interior space and away from the probe distal end body,
    wherein the interior space extends along a longitudinal axis between a distal end and a proximal end,
    wherein the proximal end of the interior space is closed, and
    wherein the proximal end of the interior space corresponds with a node position of the ultrasonic vibration.

* * * * *